(12) United States Patent
Scharp et al.

(10) Patent No.: US 10,053,520 B2
(45) Date of Patent: Aug. 21, 2018

(54) COATING FOR CELLS, REAGENTS AND METHODS

(71) Applicants: David W. Scharp, Irvine, CA (US); Alexander Gorkovenko, Mission Viejo, CA (US)

(72) Inventors: David W. Scharp, Irvine, CA (US); Alexander Gorkovenko, Mission Viejo, CA (US)

(*) Notice: Subject to any disclaimer, the term of this patent is extended or adjusted under 35 U.S.C. 154(b) by 0 days.

(21) Appl. No.: 14/638,724

(22) Filed: Mar. 4, 2015

(65) Prior Publication Data

US 2015/0250735 A1 Sep. 10, 2015

Related U.S. Application Data

(60) Provisional application No. 61/949,147, filed on Mar. 6, 2014.

(51) Int. Cl.
| | | |
|---|---|---|
| *A61K 35/28* | (2015.01) | |
| *C08B 37/00* | (2006.01) | |
| *A61K 35/32* | (2015.01) | |
| *A61K 35/39* | (2015.01) | |
| *A61K 9/00* | (2006.01) | |
| *A61K 9/50* | (2006.01) | |
| *C08L 5/00* | (2006.01) | |

(52) U.S. Cl.
CPC ........ *C08B 37/0024* (2013.01); *A61K 9/0024* (2013.01); *A61K 9/5031* (2013.01); *A61K 35/28* (2013.01); *A61K 35/32* (2013.01); *A61K 35/39* (2013.01); *C08L 5/00* (2013.01)

(58) Field of Classification Search
CPC .................................................. A61K 35/28
See application file for complete search history.

(56) References Cited

PUBLICATIONS

Satoh et al (Satohet al. (2011) Hyperbranched Glyco-Conjugated Polymers, in Complex Macromolecular Architectures: Synthesis, Characterization, and Self-Assembly (eds N. Hadjichristidis, A. Hirao, Y. Tezuka and F. Du Prez), John Wiley & Sons (Asia) Pte Ltd, Singapore), pp. 195-227.*

* cited by examiner

*Primary Examiner* — Benjamin Packard
(74) *Attorney, Agent, or Firm* — Kirk Hahn

(57) ABSTRACT

The disclosure provides coated mammalian cells, and related reagents, as well as methods for coating mammalian cells, and methods for implanting the coated cells into a human host.

18 Claims, 35 Drawing Sheets

Figure 1:
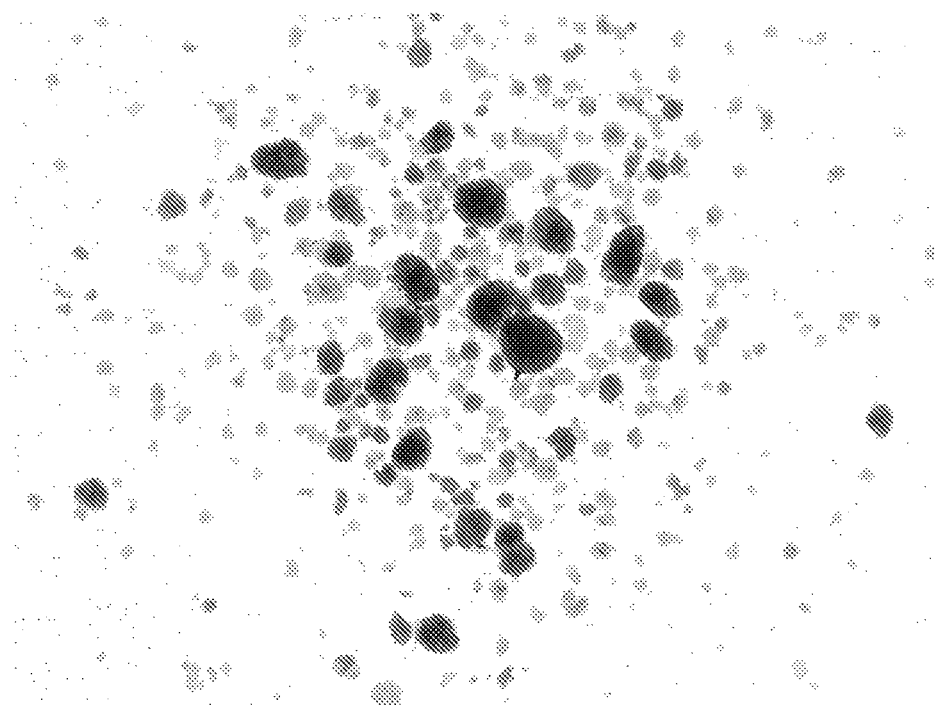

A
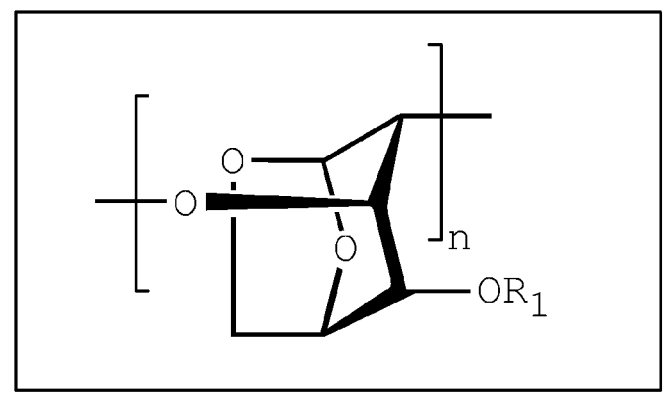
B
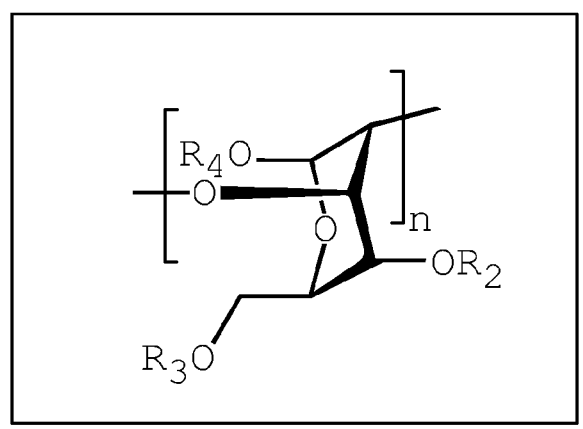
C
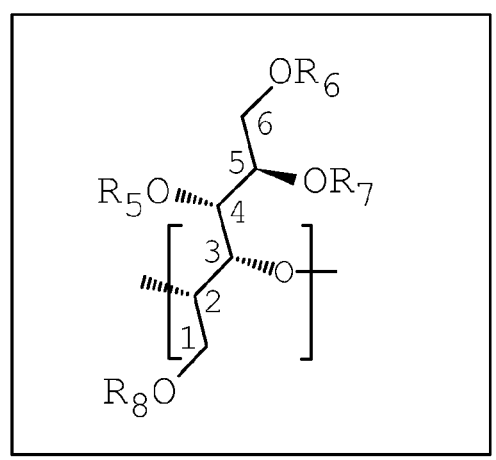
FIG. 34

COATING FOR CELLS, REAGENTS AND METHODS

CROSS-REFERENCE TO RELATED APPLICATIONS

This application claims the benefit of, and priority to, U.S. Provisional Patent Application Ser. No. 61/949,147, filed Mar. 6, 2014, the contents of which are incorporated by reference.

FIELD OF THE DISCLOSURE

The present disclosure relates to compositions of encapsulated mammalian cells, polymers for encapsulation, and methods for coating mammalian cells, implanting coated mammalian cells in a host, and for methods for ensuring expressing gene products by the implanted mammalian cells.

BACKGROUND OF THE DISCLOSURE

A variety of medical disorders result from impaired functions of specific cells. For example, type I diabetes is an autoimmune disorder arising from destruction of insulin-producing beta-cells of the pancreas. The beta-cells are part of the islets of Langerhans ("islets"). The islets contain five types of endocrine cells, including beta-cells. Therapy for type I diabetes typically involves insulin injections, where this therapeutic approach had an origin in the isolation, by Banting and Best, of an "active principle" from whole pancreas (Rosenfeld (2002) Clin. Chem. 48:2270-2288; Best (1945) Can. Med. Assoc. J. 53:204-212). A continuing risk with insulin injections, for example, is the adverse event of hypoglycemia arising from an insulin overdose (Jamiolkowski et al (2012) Yale J. Biol. Med. 85:37-43).

Another approach for treating type I diabetes, as well as other disorders arising from deficiencies in specific cells, is cell transplantation. Cell transplantation can involve autologous transplantation, where the host's own cells are harvested, then cultured or modified ex vivo, and then reintroduced into the host. Cell transplantation can also involve allogeneic transplantation, where cells from another human host, genetically related or genetically non-related, are harvested from the other human host and then implanted into the recipient human host. Yet another approach is xenotransplantation, where cells derived from another species are transplanted into a human.

Allogeneic transplantation and xenogenic transplantation result in the adverse event of the host's immune response against the transplanted cells. To mitigate this adverse event, researchers have encapsulated cells prior to transplanatation. Encapsulation has been with a natural polymer such as alginate, or with synthetic polymers, such as hydroxyethyl methacrylate-methyl methacrylate or polyethylene glycol (PEG). Another approach has been to encapsulate cells in a small device, for example, a device made of polysilicon, alumina, or epoxy-based polymers. The term "implant," in this context, generally refers to mammalian cells that have a coating, or that are contained in a device, and where the coated cells or where the device is implanted in a human host.

Regarding the transplantation of coated cells, problems include the deterioration of the coating over a period of weeks or months, failure of cells to thrive due to inadequate supply of oxygen, growth of fibroblasts over the implant, and the host's immune response against the cells (see, e.g., Vaithilingam and Tuch (2011) Rev. Diabetic Studies. 8:51-67). Some of the above problems result from a pore size that is too large, and that allows the host's antibodies to enter the capsule. Immune response against the cells can be exacerbated by the coating itself, for example, where the coating includes polyornithine. Yet another problem, also related to the nature of the polymers, is where polymers are crosslinked over the cells, and where crosslinking is by way of toxic free radicals. Moreover, another problem with encapsulation technology are attempts to manufacture overly complex capsules, such as those using several different layers (see, e.g., Wang et al (2008) Transplantation. 85:331-337).

SUMMARY OF THE DISCLOSURE

In embodiments, the present disclosure provides coated mammalian cells, and related reagents, as well as methods for coating mammalian cells, and methods for implanting the coated cells into a human host.

In embodiments, the present disclosure provides polymeric capsule that is capable of encapsulating at least one mammalian cell, the polymeric capsule comprising a polymer that comprises a plurality of monomer units, wherein the polymer comprises a C2-C3 linked polyether of a 1,6:2,3-dianhydrohexopyranose, wherein the plurality of monomer units comprises a monomeric unit that is structure A of FIG. 34, a monomeric unit that is structure B of FIG. 34, or a monomeric unit that is structure C of FIG. 34, or any combination of said monomeric units, wherein the capsule exhibits reverse thermal gelation properties in aqueous media.

Also provided is the above polymeric capsule, wherein the polymer comprises one or both of the polymers:

(a) poly (2-3)-1,6-anhydro-4-O-(methyl-co-(2-methoxyethyl)-co-(2-(2-methoxyethoxyethyl))-beta-D-glucopyranose (t-OMD-91); and (b) poly (2-3)-1,6-anhydro-4-O-(methyl-co-(2-methoxyethyl)-co-(2-(2-methoxyethoxyethyl))-b-D-glucopyranose (t-OMD-130).

Also provided is the above polymeric capsule, wherein the capsule is capable of comprising at least one mammalian islet, and wherein the capsule is capable of maintaining the at least one mammalian islet in a centered position in the capsule.

Further provided is the above polymeric capsule, wherein the at least one mammalian cell comprises a pancreatic beta cell, an islet of Langerhans, a stem cell, or a chondrocyte.

Also provided is the above polymeric capsule, that comprises at least one mammalian islet that is in a centered position in the capsule.

Further provided is the above polymeric capsule, that comprises less than 10% alginate by weight.

Moreover, what is provided is the above polymeric capsule, that comprises less than 10% polyethylene glycol by weight.

In population embodiments, what is provided is a population of the above polymeric capsule, wherein at least 90% of the capsules in the population comprise at least one encapsulated mammalian islet, and wherein at least 50% of the capsules that comprise at least one encapsulated mammalian islet comprise at least one encapsulated mammalian islet that is centered in the capsule.

Also provided is the above population of the polymeric capsule, wherein at least 90% of the capsules in the population comprise at least one encapsulated mammalian islet, and wherein at least 80% of the capsules that comprise at least one encapsulated mammalian islet comprise at least one encapsulated mammalian islet that is centered in the capsule.

Also provided is the above population of the polymeric capsule, wherein at least 90% of the capsules in the population comprise at least one encapsulated mammalian islet, and wherein at least at least 50%, at least 60%, at least 70%, at least 75%, at least 80%, at least 85%, at least 90%, or at least 95% of the capsules that comprise the at least one encapsulated mammalian islet are capable of excluding a globular protein of a molecular weight of at least 200 kilodaltons.

Also provided is the above population of the polymeric capsule, wherein at least 90% of the capsules in the population comprise at least one encapsulated mammalian islet, and wherein at least 50%, at least 60%, at least 70%, at least 75%, at least 80%, at least 85%, at least 90%, at least 95%, of the capsules that comprise the at least one encapsulated mammalian islet are capable of excluding a globular protein of a molecular weight of at least 100 kilodaltons.

Further embraced is the above population of polymeric capsule, wherein at least 50%, at least 60%, at least 70%, at least 80%, at least 90%, at least 95%, of the capsules in the population comprise at least one encapsulated mammalian islet (encapsulated islets), and wherein the encapsulated islets are capable of responding to glucose that is administered to the encapsulated islets, wherein said capable of responding to glucose comprises increased expression of insulin.

Also contemplated, is the above population of polymeric capsule, wherein the increased expression of insulin is characterized by a Stimulation Index-1 (SI-1) that is at least 10%, at least 15%, at least 20%, at least 25%, at least 30%, greater than a SI-1 of naked islets.

Also provided is the above population of the polymeric capsule, wherein the increased expression of insulin is characterized by a Stimulation Index-2 (SI-2) that is at least 10%, at least 15%, at least 20%, at least 25%, at least 30%, greater than a SI-2 of naked islets.

Also provided is the above population of the polymeric capsule, wherein the increased expression of insulin is characterized by a Stimulation Index-3 (SI-3) that is at least 10%, at least 15%, at least 20%, at least 25%, at least 30%, greater than a SI-3 of naked islets.

In a produce by process embodiment, what is provided is a population of capsules comprising encapsulated mammalian cells that are encapsulated by a polymeric capsule, wherein the population of capsules comprising encapsulated cells is made by a method that comprises the steps of:

(a) Preparing a suspension, slurry, or pellet of mammalian cells;

(b) Providing an available (existing) polymer that comprises a plurality of monomer units that are a C2-C3 linked polyether of a 1,6:2,3-dianhydrohexopyranose, wherein the plurality of monomer units comprises a monomeric unit that is structure A of FIG. 34, a monomeric unit that is structure B of FIG. 34, or a monomeric unit that is structure C of FIG. 34, or any combination of said monomeric units;

(c) Combining the suspension, slurry, or pellet of mammalian cells with the available polymer to produce an aqueous suspension of mammalian cells in said polymer, optionally with also combining an additional aqueous solution that does not comprise mammalian cells in order to ensure enough aqueous solution to provide an aqueous suspension of mammalian cells;

(d) Combining the aqueous suspension of mammalian cells in said polymer with an oil, to produce a combination, wherein the combination is at a first temperature that is a relatively low temperature, and stirring or agitating the combination to produce an emulsion; and (e) Raising the temperature of the emulsion to a second temperature that is a relatively high temperature, wherein the relatively high temperature is capable of supporting encapsulation of the mammalian cells, wherein a plurality of encapsulated mammalian cells is formed, and wherein the first relatively low temperature is a temperature that is not capable of supporting encapsulation of the mammalian cells.

Regarding the above process, preparing can take the form of, e.g., placing the suspension, slurry, or pellet, on a laboratory bench. Preparing can take the form of, e.g., transferring the suspension, slurry, pellet, from a vial to a test tube. Preparing can take the form of removing the suspension, slurry, or pellet, from a refrigerator. These examples do not impose any limitation on what is "preparing." Providing can take the form of, e.g., placing the available or existing polymer in a test tube, in a beaker, in a vial, in a flask, and so on. Providing can take the form of, e.g., removing the available or existing polymer from a storage area, such as a refrigerator, a freezer, a dessicator, and so on. These examples of "providing" do not impose any limitation on what is "providing."

Also provided is the above population of capsules, wherein the method further comprises the step of separating the encapsulated mammalian cells from the emulsion.

Also provided is the above population of capsules, wherein the polymer comprises one or both of the polymers:

(a) poly (2-3)-1,6-anhydro-4-O-(methyl-co-(2-methoxyethyl)-co-(2-(2-methoxyethoxyethyl))-beta-D-glucopyranose(t-OMD-91); and (b) poly (2-3)-1,6-anhydro-4-O-(methyl-co-(2-methoxyethyl)-co-(2-(2-methoxyethoxyethyl))-b-D-glucopyranose (t-OMD-130).

Also provided is the above population of capsules, wherein the mammalian cells comprise at least one pancreatic beta-cell.

Also provided is the above population of capsules, wherein the population of mammalian cells comprises at least one islet of Langerhans.

Also provided is the above population of capsules, wherein the mammalian cells do not comprise any pancreatic beta-cells.

Also provided is the above population of capsules comprising said encapsulated mammalian cells, that comprises at least one empty capsule.

Also provided is a population of capsules comprising the above encapsulated mammalian cells, that further comprises empty capsules, wherein the ratio of (capsules comprising encapsulated mammalian cells)/(capsules that are empty capsules) is greater than (80)/(20). Also encompassed, is a population of capsules where the ratio is greater than 30/70, greater than 40/60, greater than 50/50, greater than 60/40, greater than 70/30, greater than 80/20, greater than 90/10, greater than 95/5, and so on.

In methods of synthesis embodiments, what is provided is a method for synthesizing a population of capsules comprising encapsulated mammalian cells, wherein the method comprises the steps of:

(a) Preparing a suspension, slurry, or pellet of mammalian cells;

(b) Preparing an available (existing) polymer that comprises a plurality of monomer units that are a C2-C3 linked polyether of a 1,6:2,3-dianhydrohexopyranose, wherein the plurality of monomer units comprises a monomeric unit that is structure A of FIG. 34, a monomeric unit that is structure B of FIG. 34, or a monomeric unit that is structure C of FIG. 34, or any combination of said monomeric units;

(c) Combining the suspension, slurry, or pellet of mammalian cells with the available polymer to produce an aqueous suspension of mammalian islets in the available polymer, optionally with also combining an additional aqueous solution that does not comprise mammalian cells in order to ensure enough aqueous solution to provide an aqueous suspension of mammalian cells;

(d) Combining the aqueous suspension of mammalian cells in said polymer with an oil, to produce a combination, wherein the combination is at a first temperature that is a relatively low temperature, and stirring or agitating the combination to produce an emulsion;

(e) Raising the temperature of the emulsion to a second temperature that is a relatively high temperature, wherein the relatively high temperature is capable of supporting encapsulation of the mammalian cells, wherein a plurality of encapsulated mammalian cells is formed, and wherein the first relatively low temperature is defined as one that is not capable of supporting encapsulation of the mammalian cells; and (f) Reducing the temperature to a third temperature that is not capable of supporting further encapsulation of mammalian cells.

Regarding the above process, preparing can take the form of, e.g., placing the suspension, slurry, or pellet, on a laboratory bench. Preparing can take the form of, e.g., transferring the suspension, slurry, pellet, from a vial to a test tube. Preparing can take the form of removing the suspension, slurry, or pellet, from a refrigerator. These examples do not impose any limitation on what is "preparing." Providing can take the form of, e.g., placing the available or existing polymer in a test tube, in a beaker, in a vial, in a flask, and so on. Providing can take the form of, e.g., removing the available or existing polymer from a storage area, such as a refrigerator, a freezer, a dessicator, and so on. These examples of "providing" do not impose any limitation on what is "providing."

Also provided is the above method or process, wherein the polymer comprises one or both of the polymers:

(a) poly (2-3)-1,6-anhydro-4-O-(methyl-co-(2-methoxyethyl)-co-(2-(2-methoxyethoxyethyl))-beta-D-glucopyranose(t-OMD-91); and (b) poly (2-3)-1,6-anhydro-4-O-(methyl-co-(2-methoxyethyl)-co-(2-(2-methoxyethoxyethyl))-b-D-glucopyranose (t-OMD-130).

Methods of administration are also provided. Also provided is the above method or process for administering the population of capsules comprising the above encapsulated mammalian cells to a mammalian subject, the method comprising:

(a) Storing the population of capsules in a medical device that is capable of mediating transfer of the population of capsules to a location in the mammalian subject that is inside the body of the mammalian subject; and (b) Transferring the population of capsules with the medical device into said location in the mammalian subject.

Also provided is the above method, wherein the mammalian cells comprise at least one pancreatic beta-cell.

Also provided is the above method, wherein the population of mammalian cells comprises at least one islet of Langerhans.

Also provided is the above method, wherein the mammalian cells do not comprise any pancreatic beta-cells.

Also provided is the above method, wherein the location is subcutaneous.

The present disclosure encompasses any combination of each independent claim with one, two, three, four, five, six, seven, eight, nine, or more, or all of the dependent claims. For example, where independent Claim 1 has three dependent claims (Claim 2, Claim 3, and Claim 4), the present disclosure encompasses, without implying any limitation, the combination of Claim 1+Claim 2; the combination of Claim 1+Claim 3, the combination of Claim 1+Claim 4, the combination of Claims 1, 2, and 3; the combination of Claims 1, 2, and 4; the combination of Claims 1, 2, and 4; the combination of Claims 1, 3, and 4; and the combination of Claims 1, 2, 3, and 4.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

Throughout the present disclosure, certain abbreviations are used. The following list defines various abbreviations used herein: AIBN (azobisisobutryonitrile); DI water (de-ionized water); DNA (deoxyribonucleic acid); DTZ (dithazone); ELISPOT assay (enzyme linked immunospot assay); FDA (fluorescein diacetate); hMSC (human mesenchymal stem cells); IBMX (3-isobutyl-1-methylxanthine); IEQ (islet equivalent); LCST (lower critical solution temperature); MVC (minimal volume capsules); OPF (oligo(poly(ethylene glycol)fumarate)); PD (polydispersity); PEG (polyethylene glycol); PEO (poly(ethylene oxide)); PBS (phosphate buffered saline); PPF (poly(propylene fumarate)); PPO (poly(propylene oxide); Prodo® (Prodo Laboratories, Inc., Irvine, Calif.); PVA (poly(vinyl) alcohol); RPM (revolutions per minute); RTG (reverse thermal gelation); SFCA (surfactant free cellulose filter); THF (tetrahydrofuran); TRGel® (commercial name for gels from TRGel, Inc., Irvine, Calif.); UV light (ultraviolet light); VEGF (vascular endothelial growth factor).

BRIEF DESCRIPTIONS OF THE FIGURES

Figure 2:
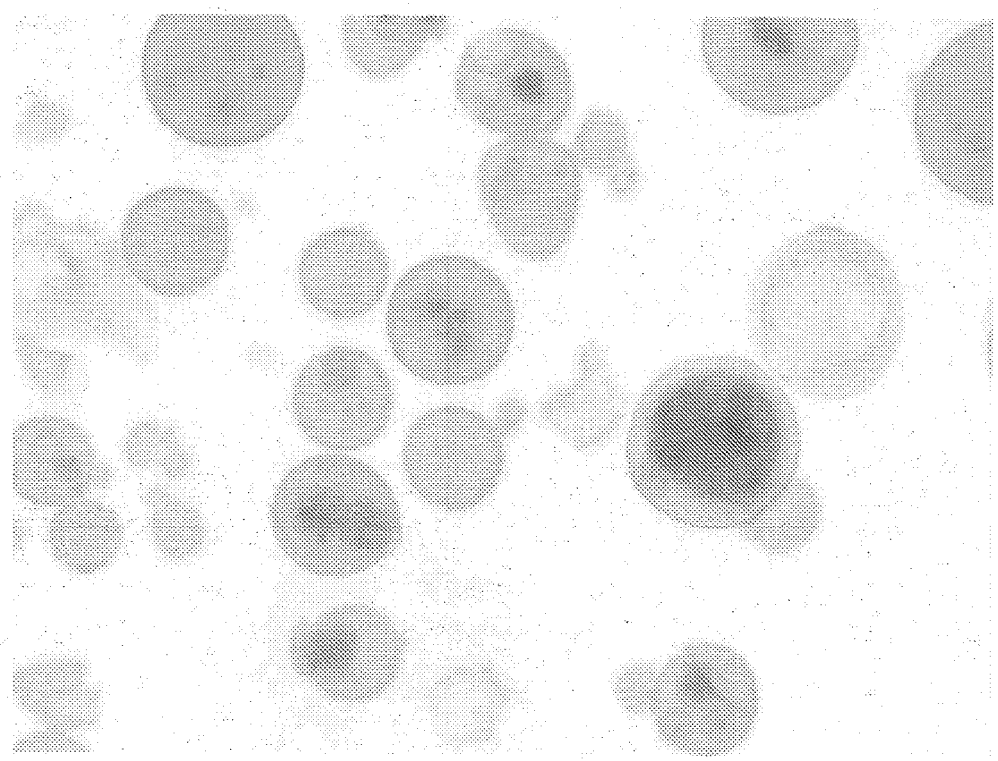
Figure 3:
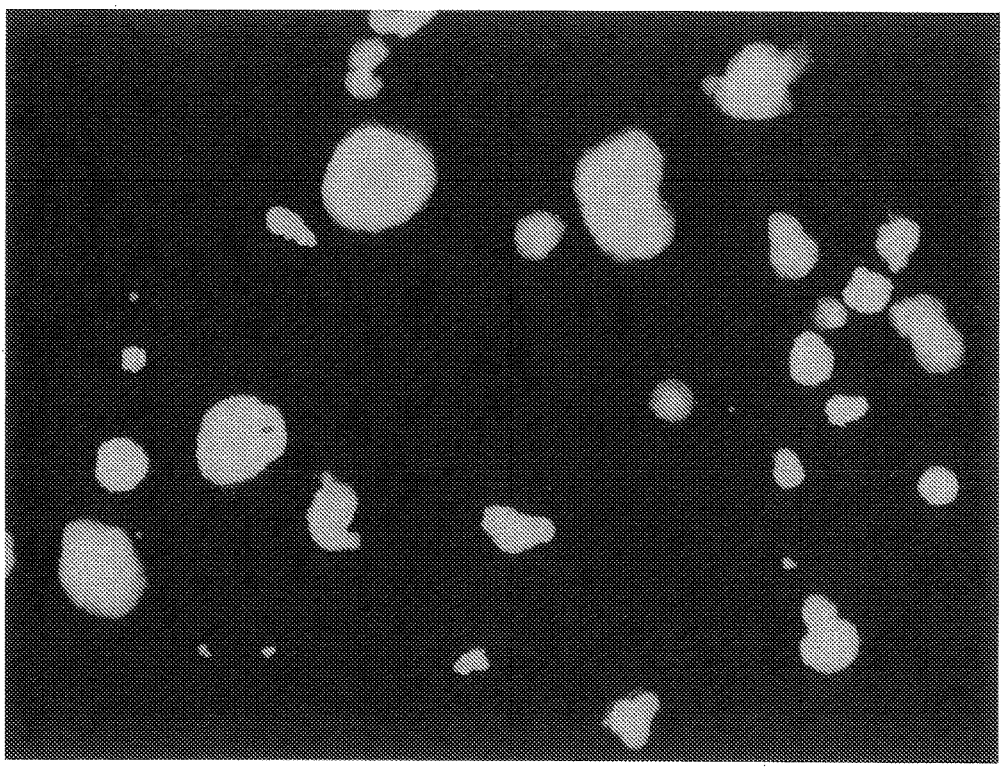
Figure 4:
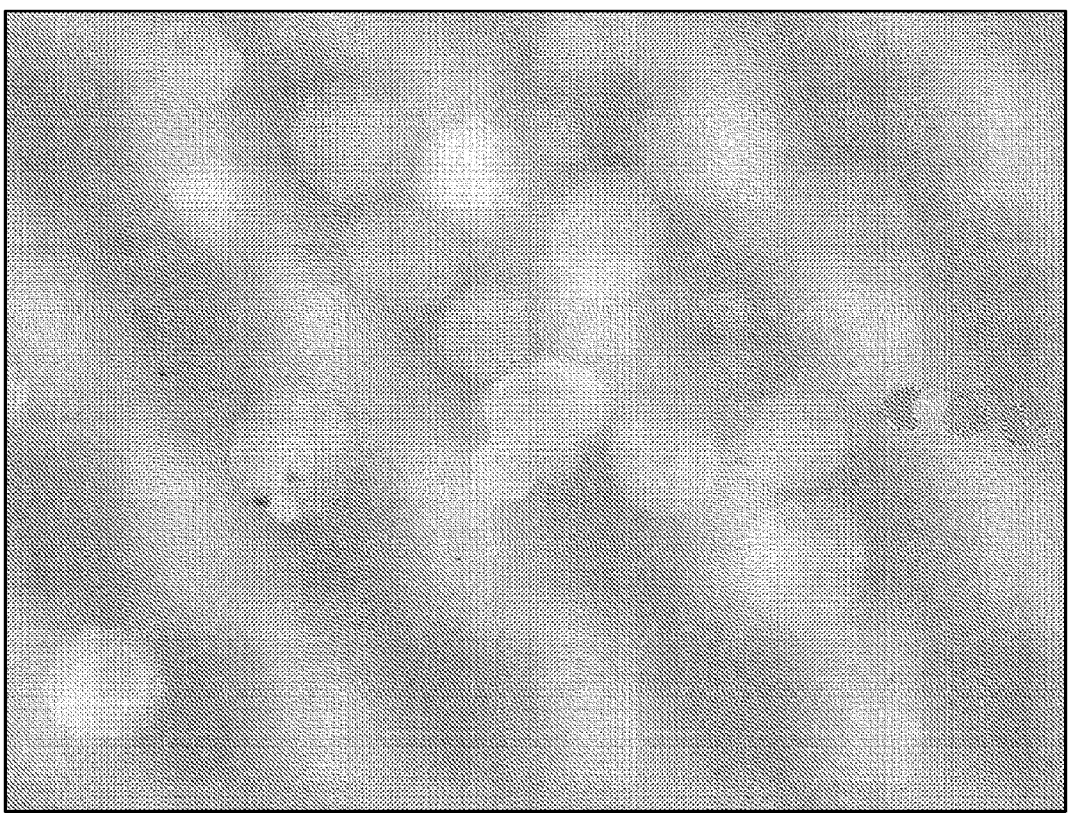
Figure 5:
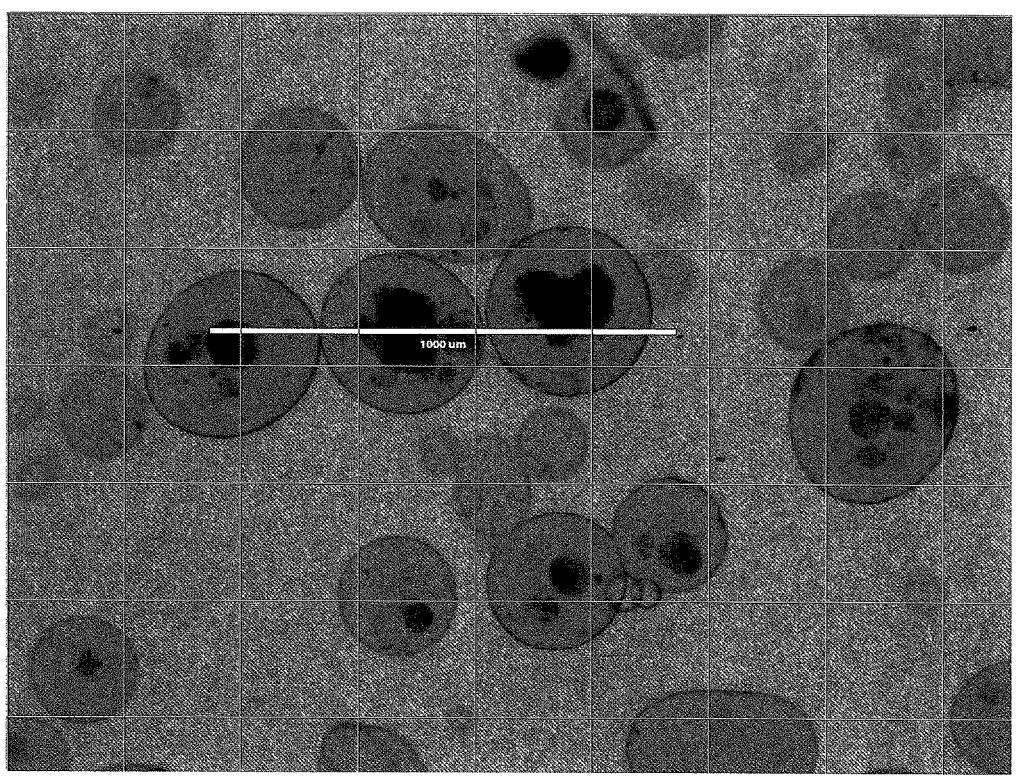
Figure 6:
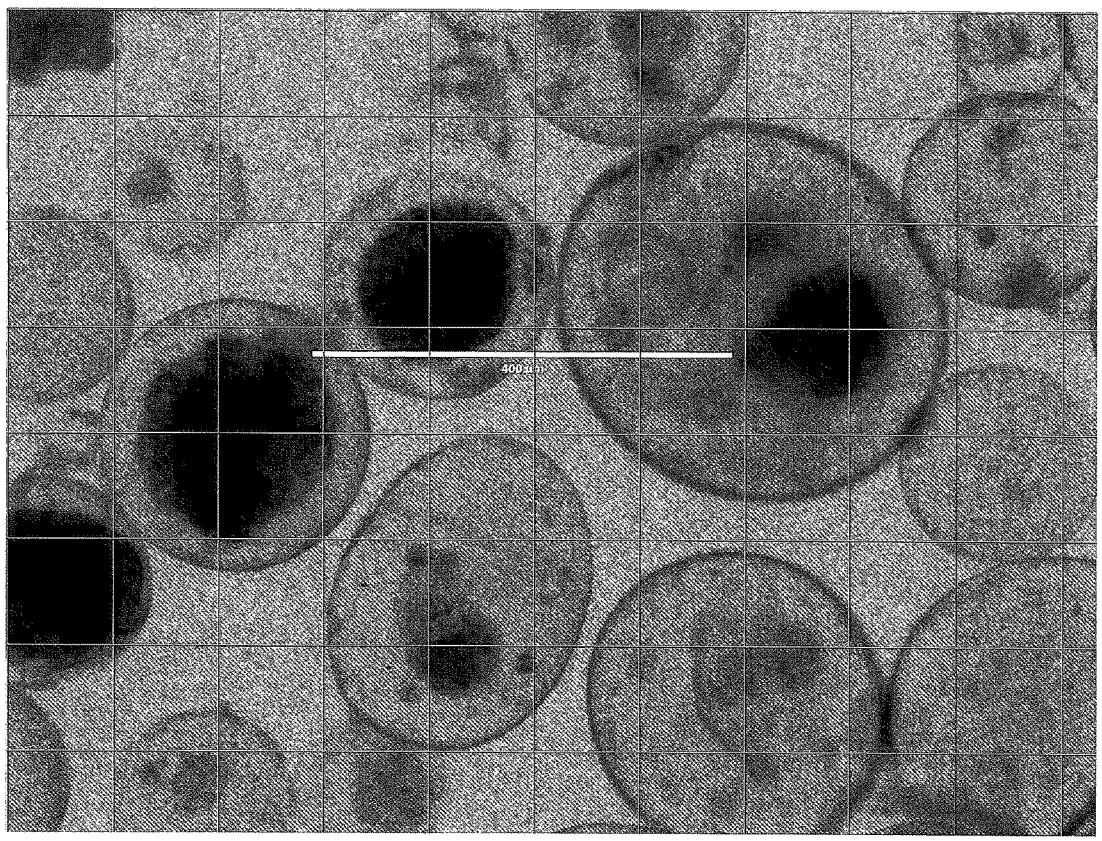
Figure 7:
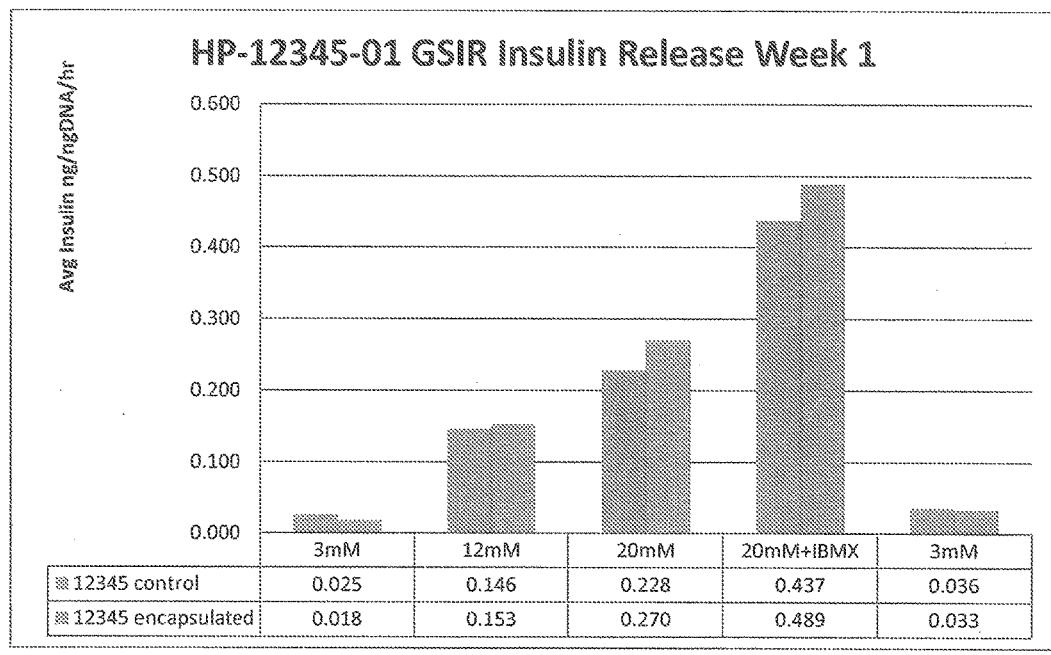
Figure 8:
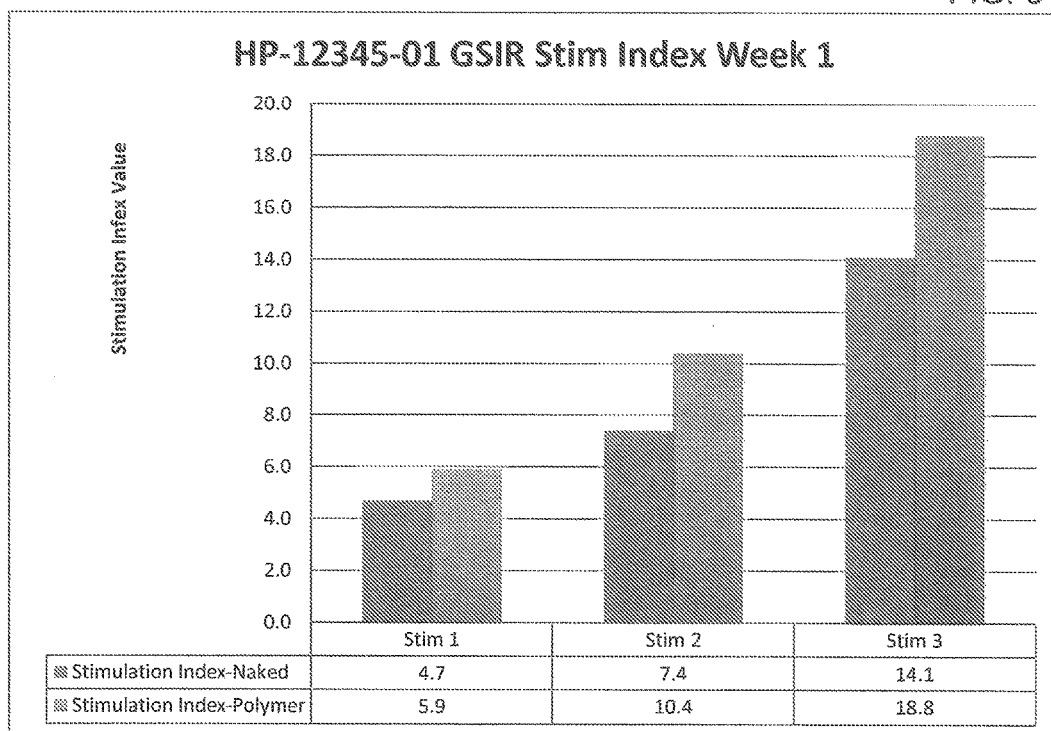
Figure 9:
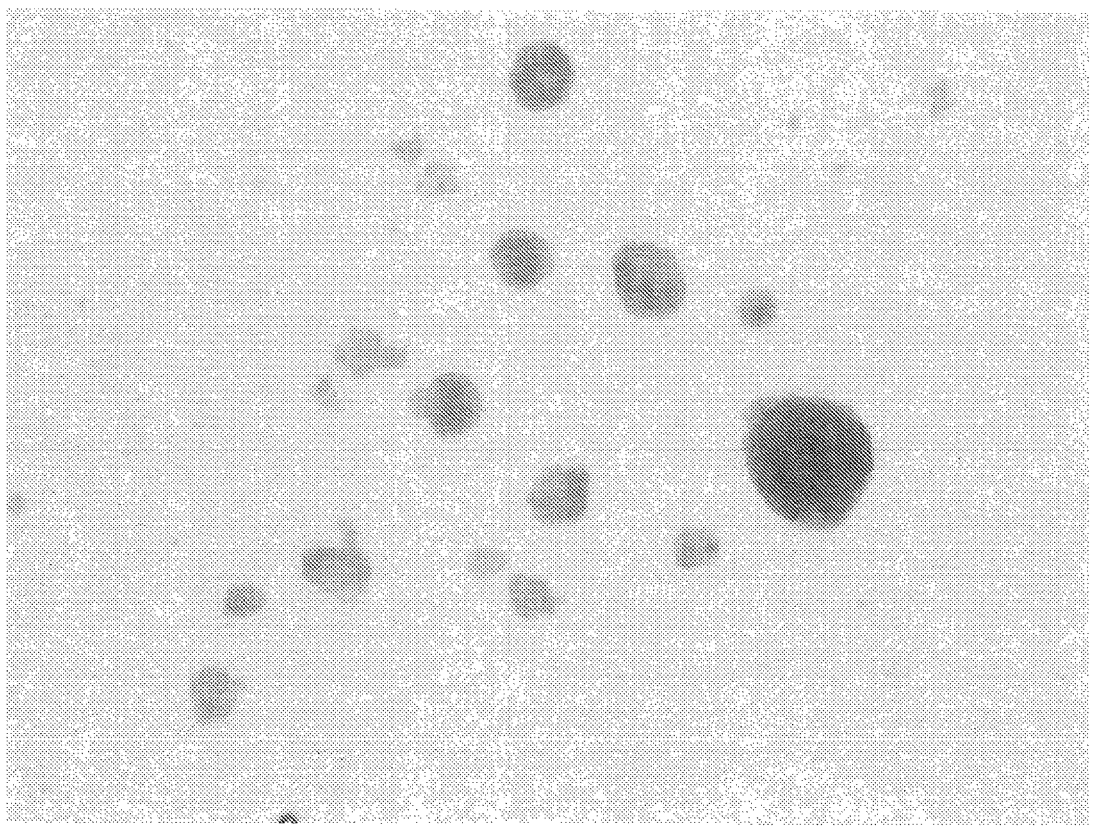
Figure 10:
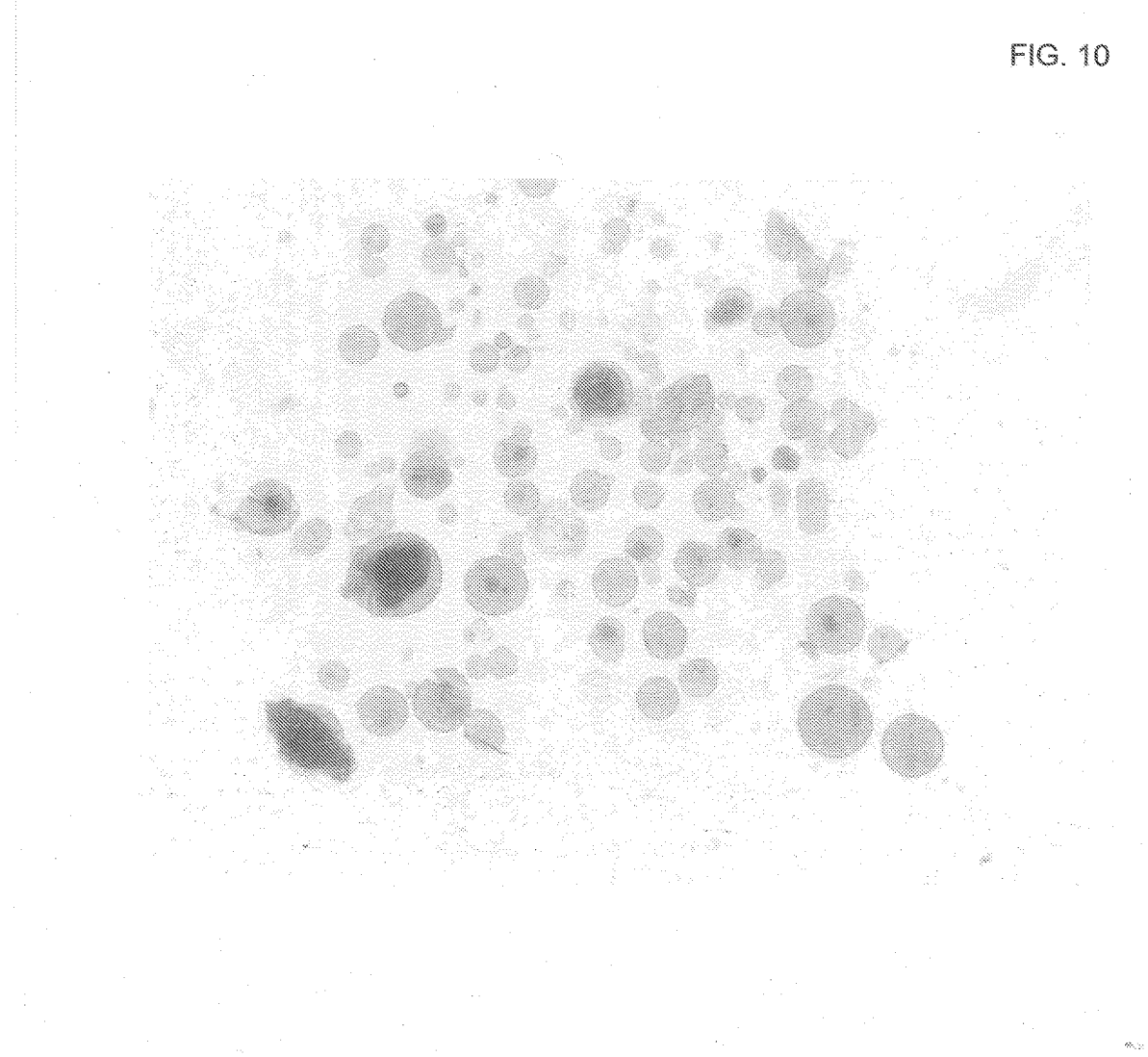
Figure 11:
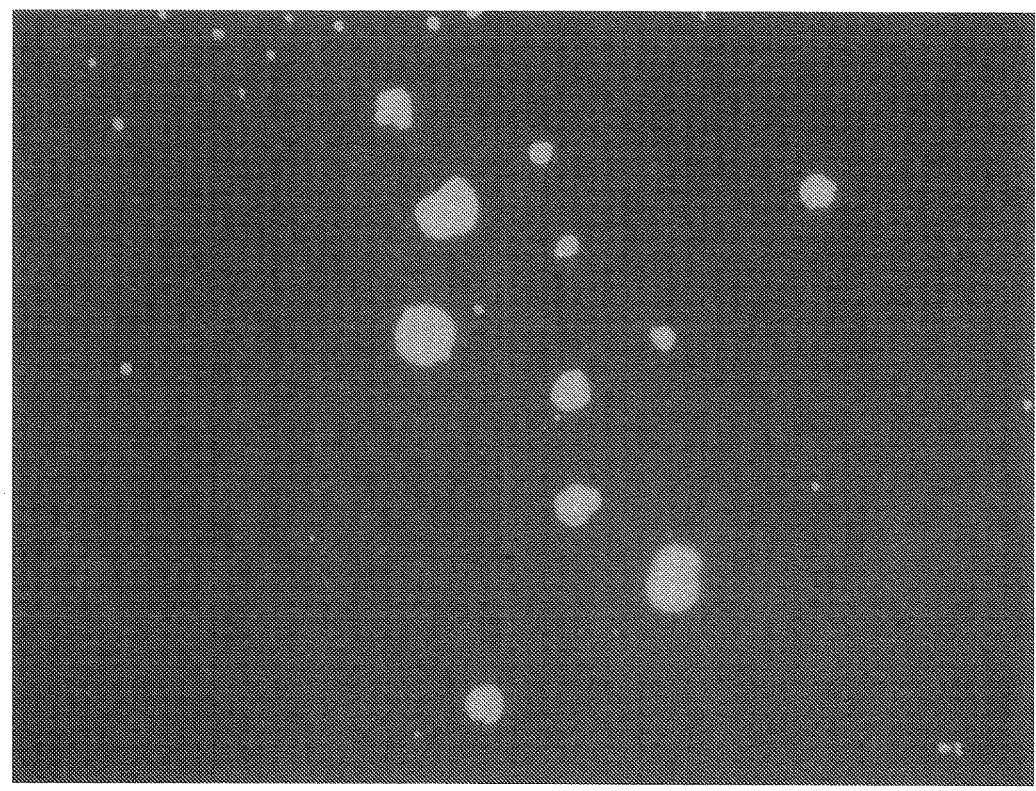
Figure 12:
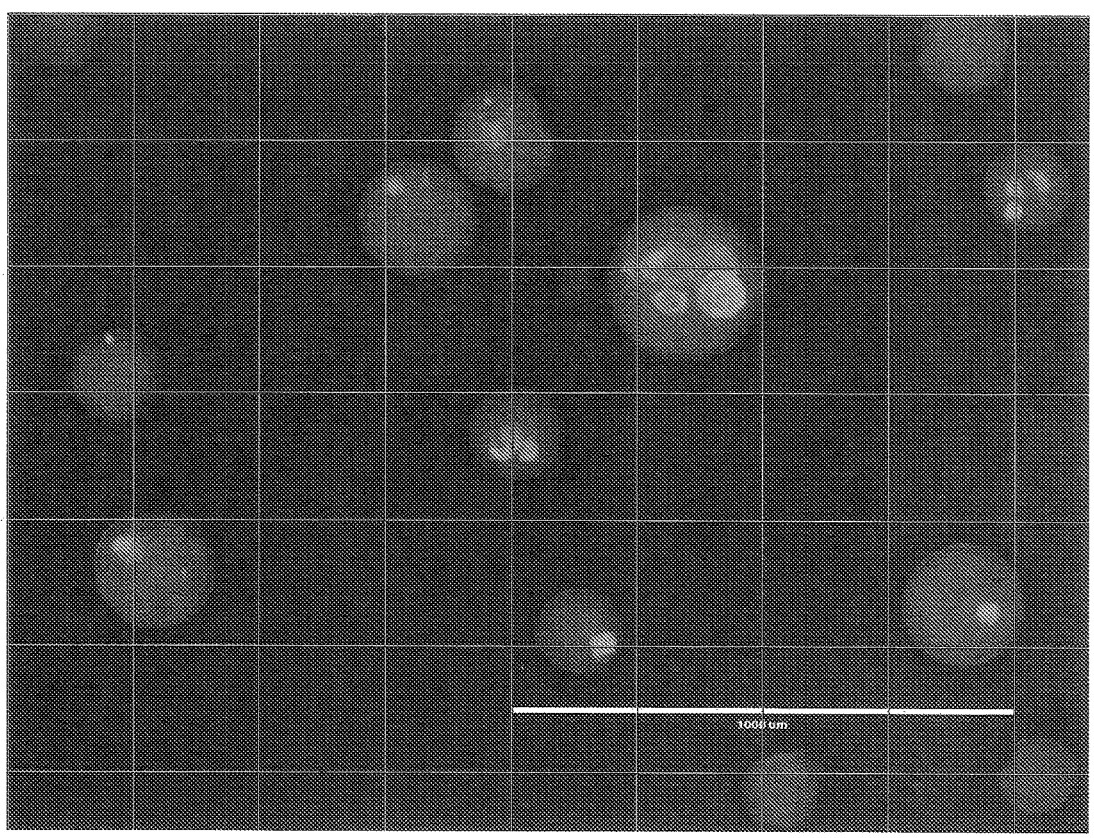
Figure 13:
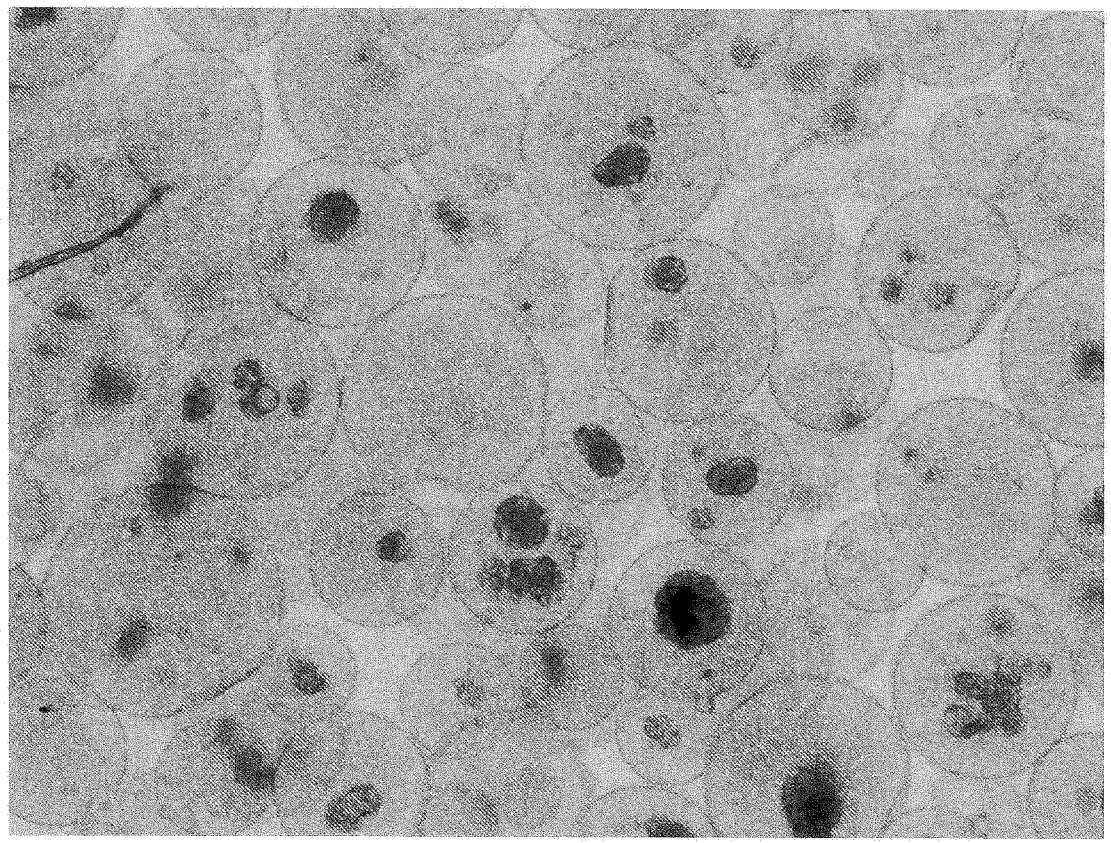
Figure 14:
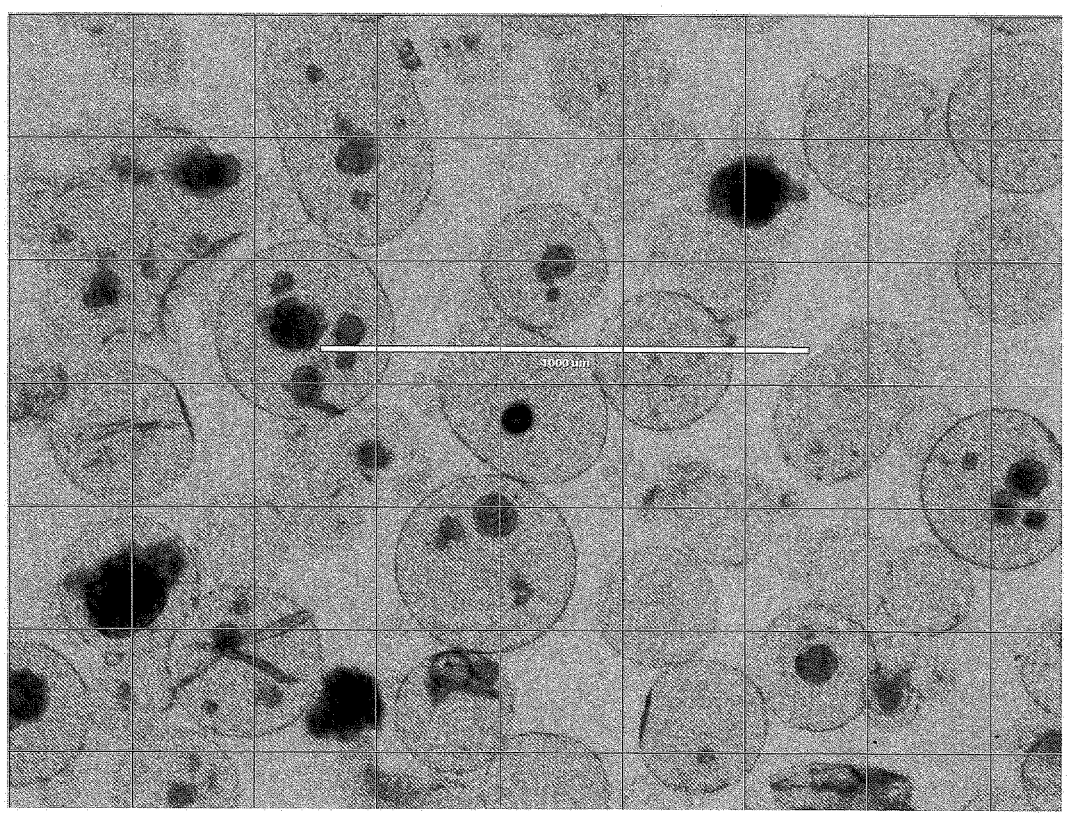
Figure 15:
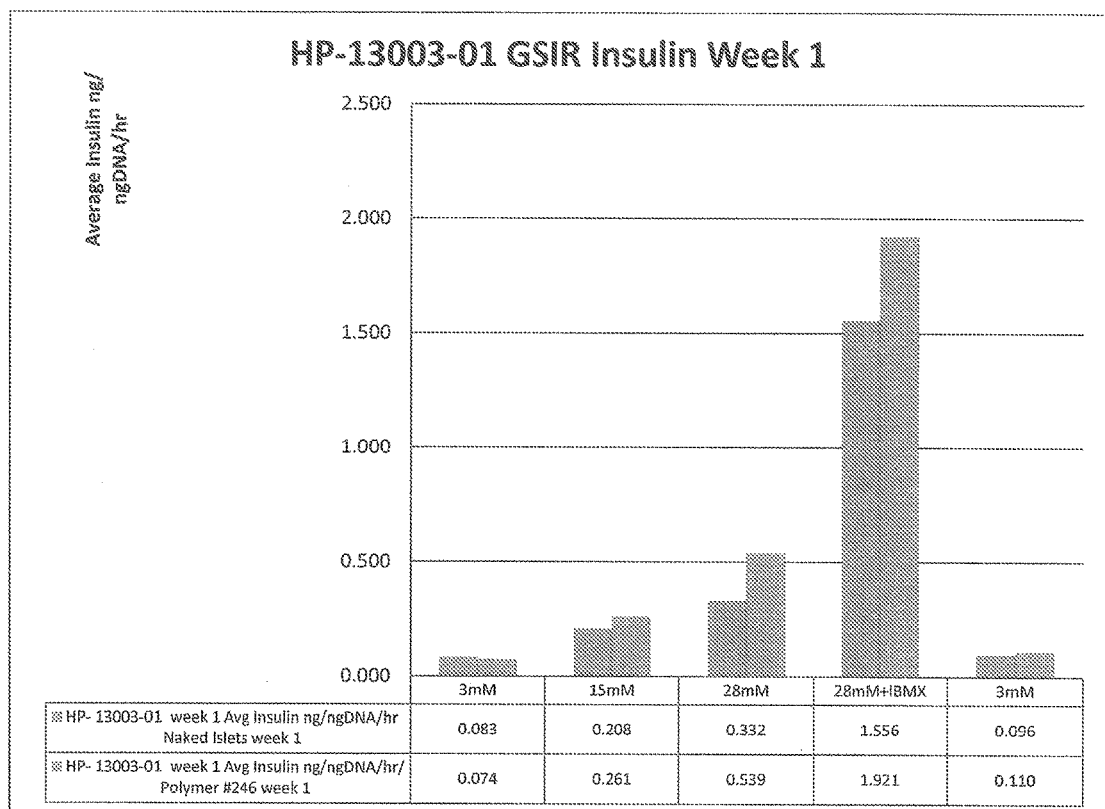
Figure 16:
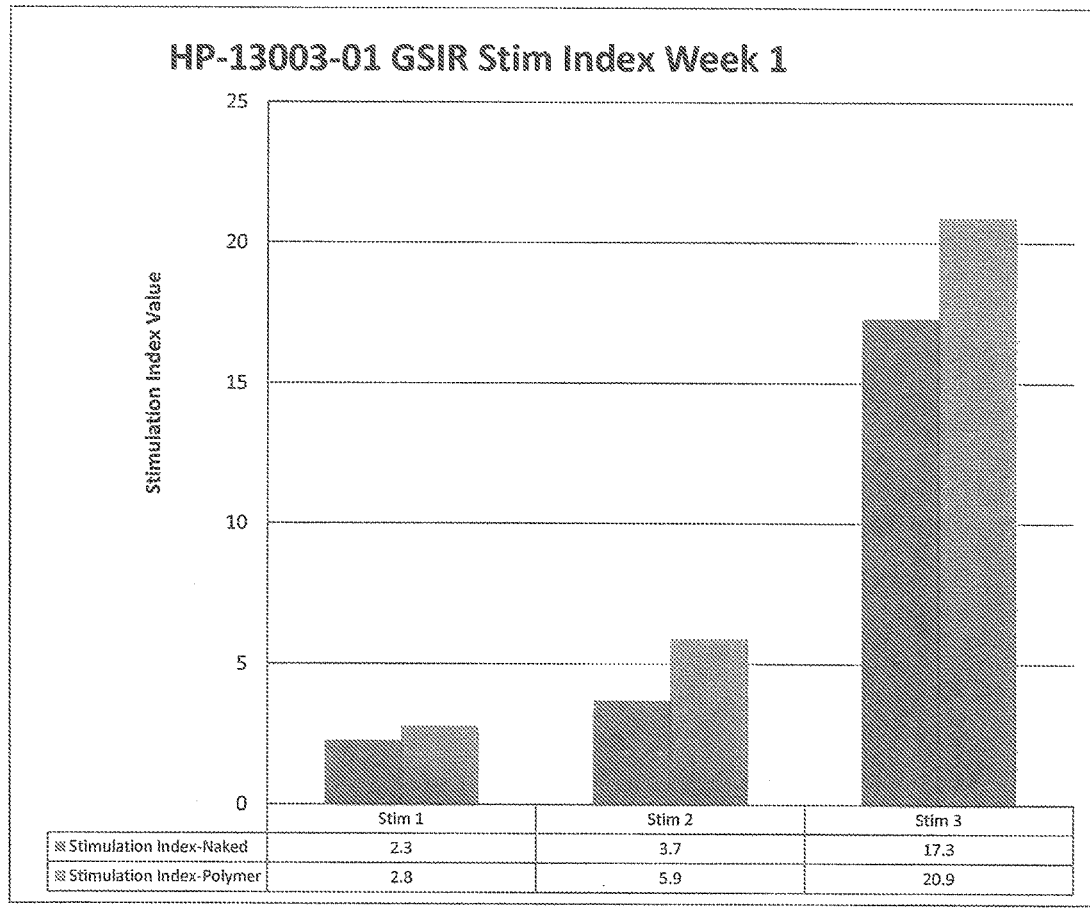

FIG. 1. Dithazone staining of naked islets.
FIG. 2. Dithazone staining of encapsulated islets.
FIG. 3. Viability staining of naked islets.
FIG. 4. Viability staining of encapsulated islets.
FIG. 5. Encapulsated islets with bar showing 1000 micrometer (1000 μm).
FIG. 6. Encapulsated islets with bar showing 400 micrometer (400 μm).
FIG. 7. Glucose Stimulate Insulin Release (GSIR) for week 1.
FIG. 8. Glucose Stimulate Insulin Release (GSIR) for week 1.
FIG. 9. Dithazone staining of naked islets.
FIG. 10. Dithazone staining of encapsulated islets.
FIG. 11. Viability staining of naked islets.
FIG. 12. Viability staining of encapsulated islets, with bar showing 1000 micrometers (1000 μm).
FIG. 13. Encapsulated islets.
FIG. 14. Encapsulated islets, with bar showing 1000 micrometers (1000 μm).
FIG. 15. Glucose Stimulate Insulin Release (GSIR) for week 1.
FIG. 16. Glucose Stimulate Insulin Release (GSIR) for week 1.

Figure 17:
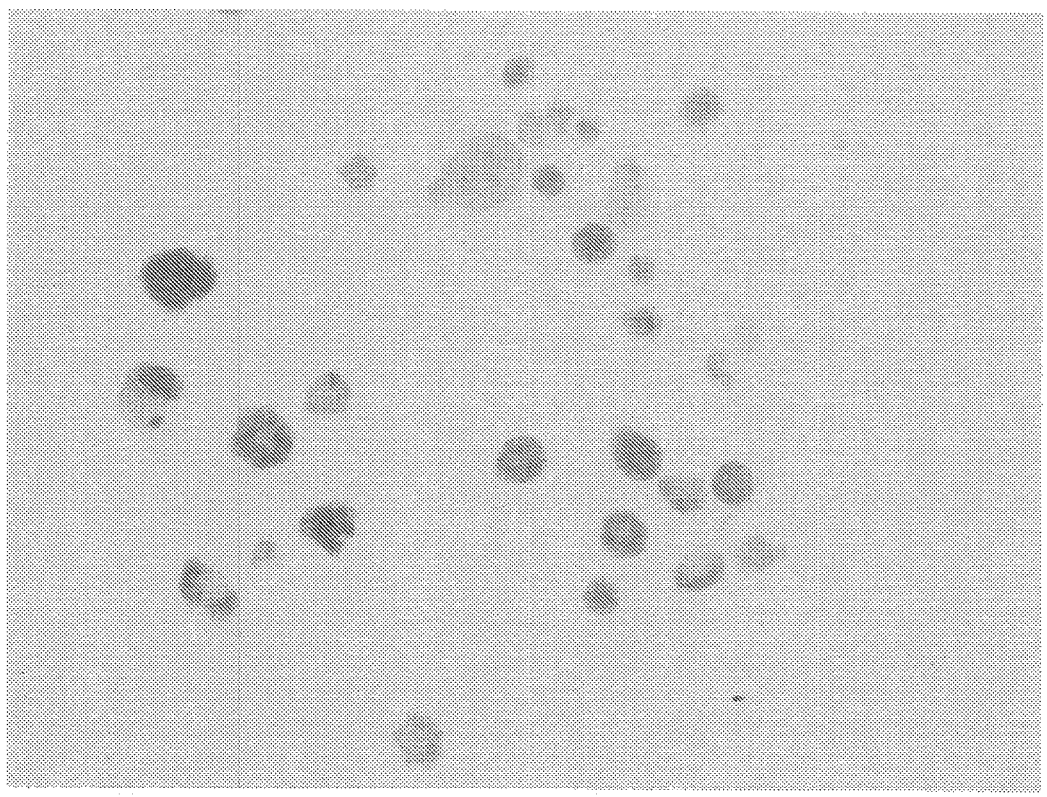
Figure 18:
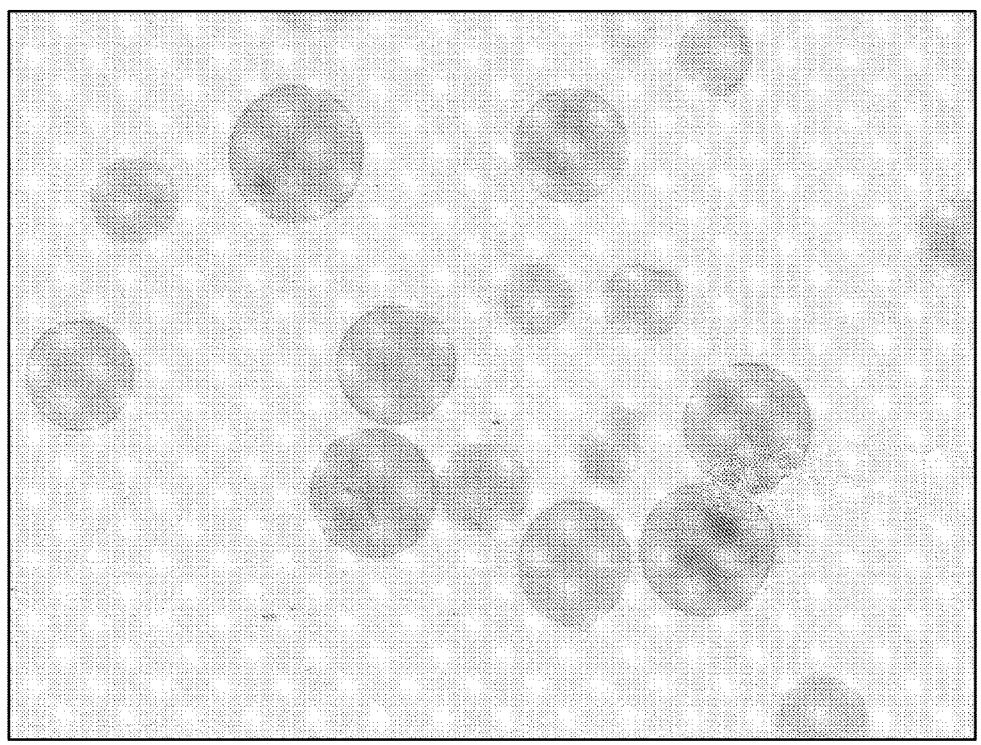
Figure 19:
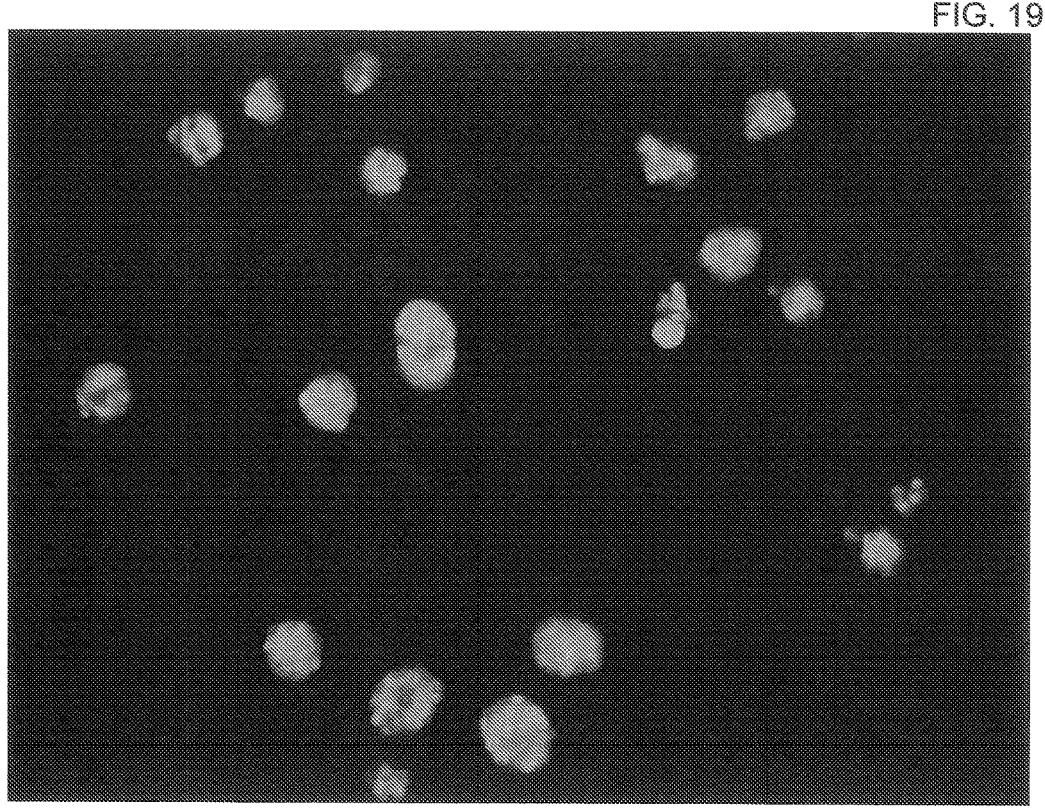
Figure 20:
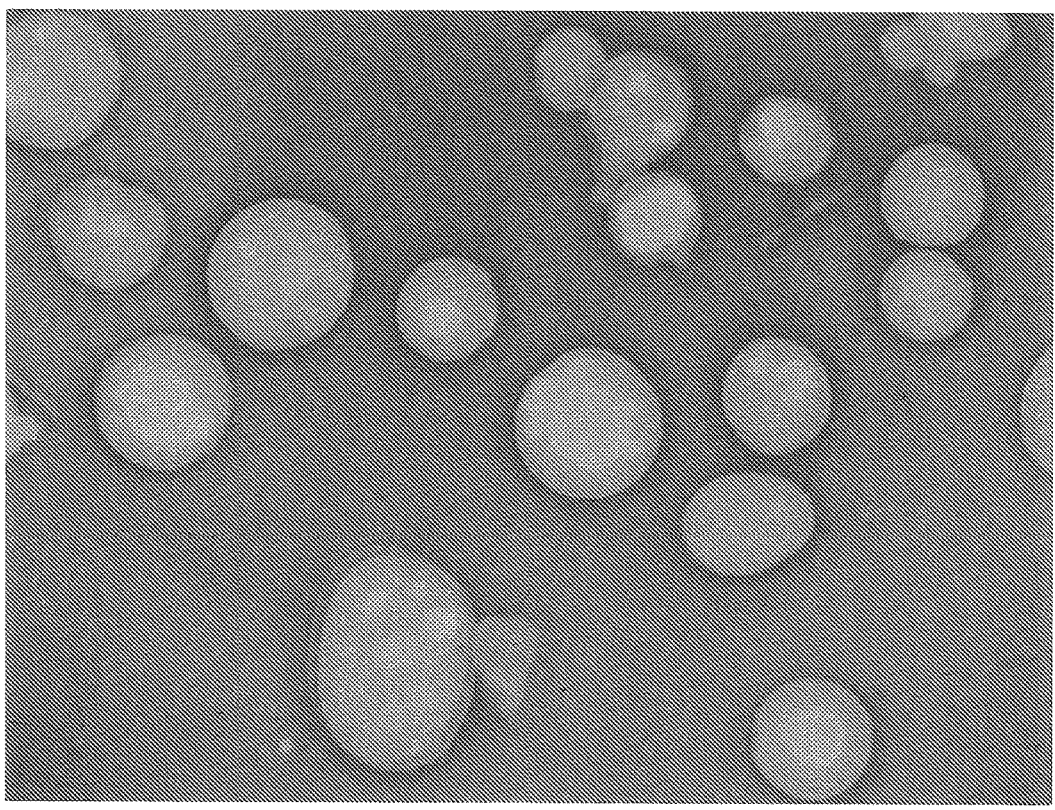
Figure 21:
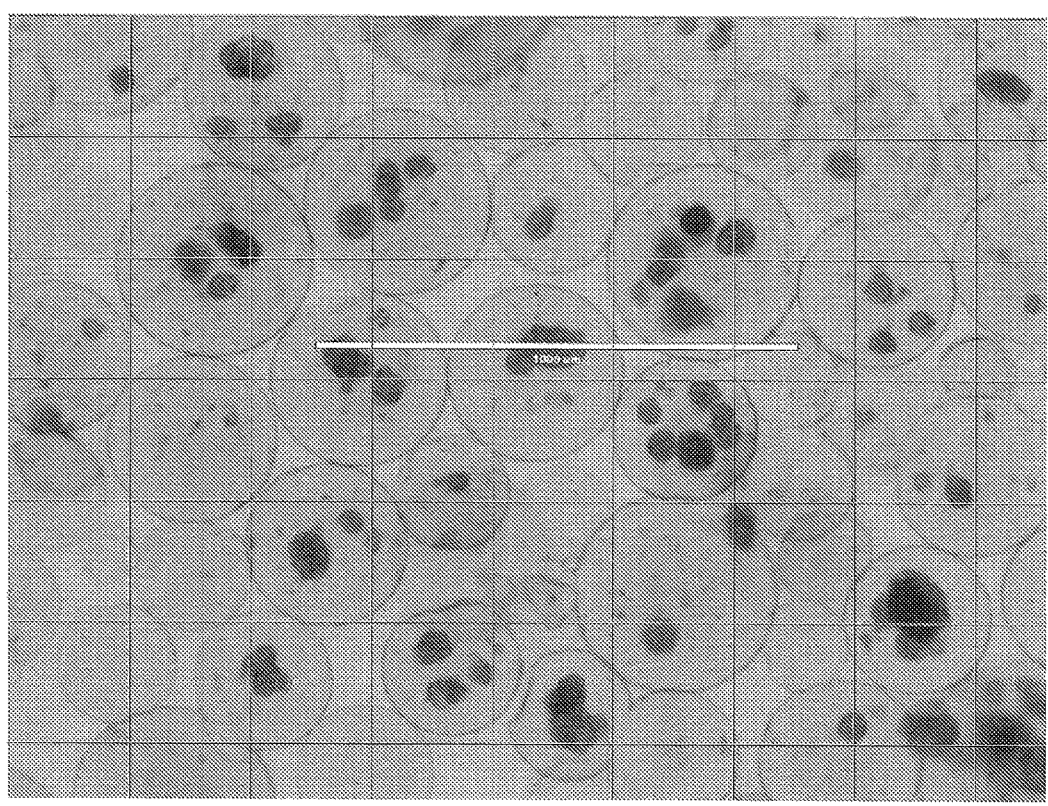
Figure 22:
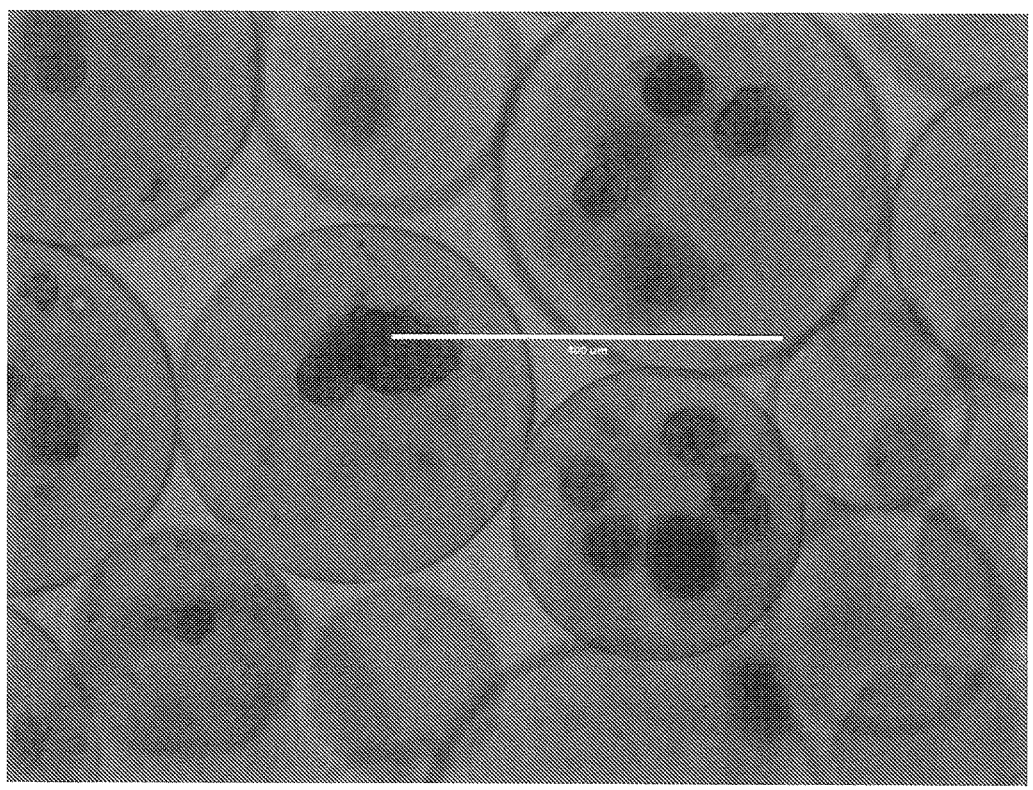
Figure 23:
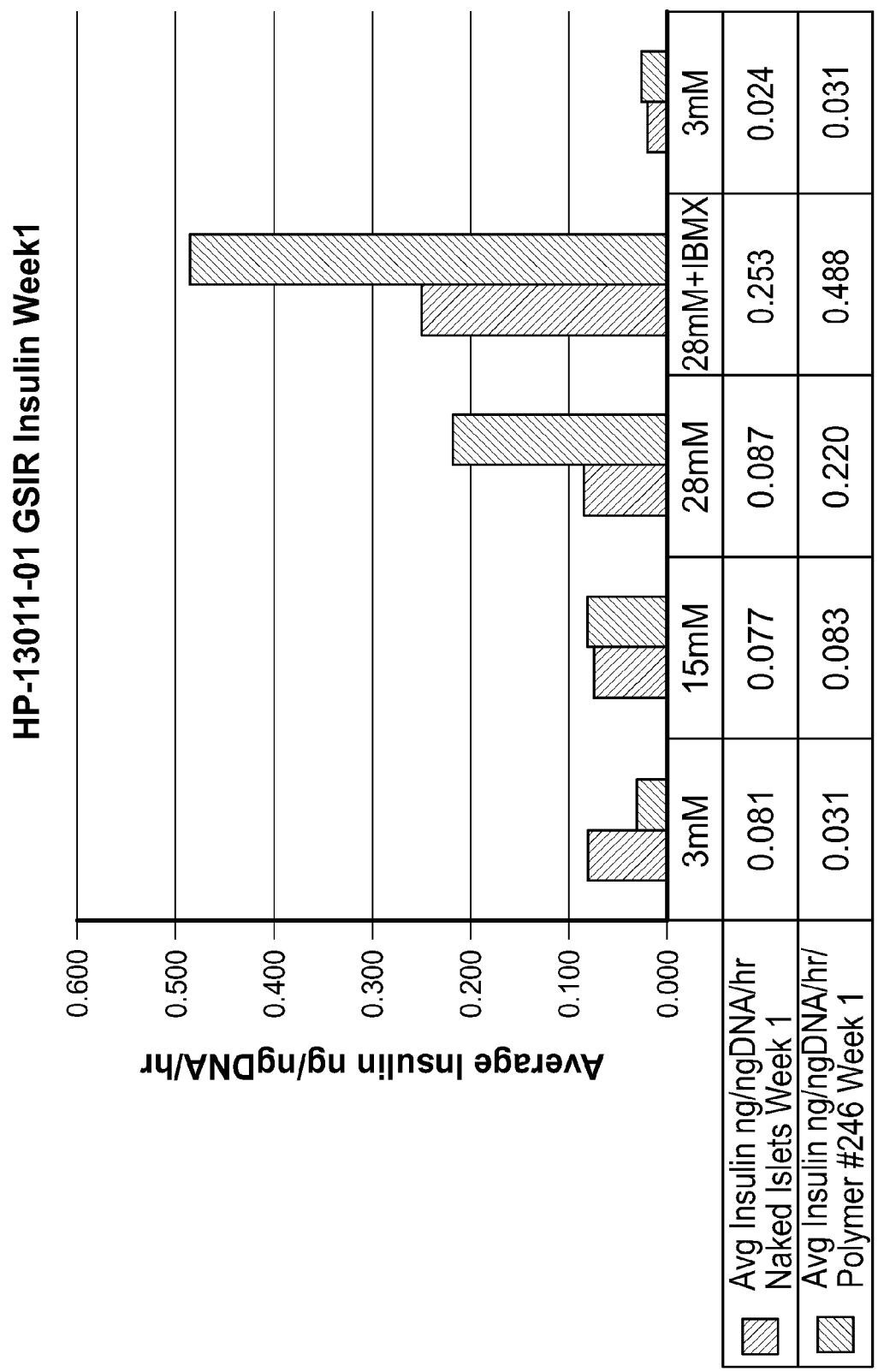
Figure 24:
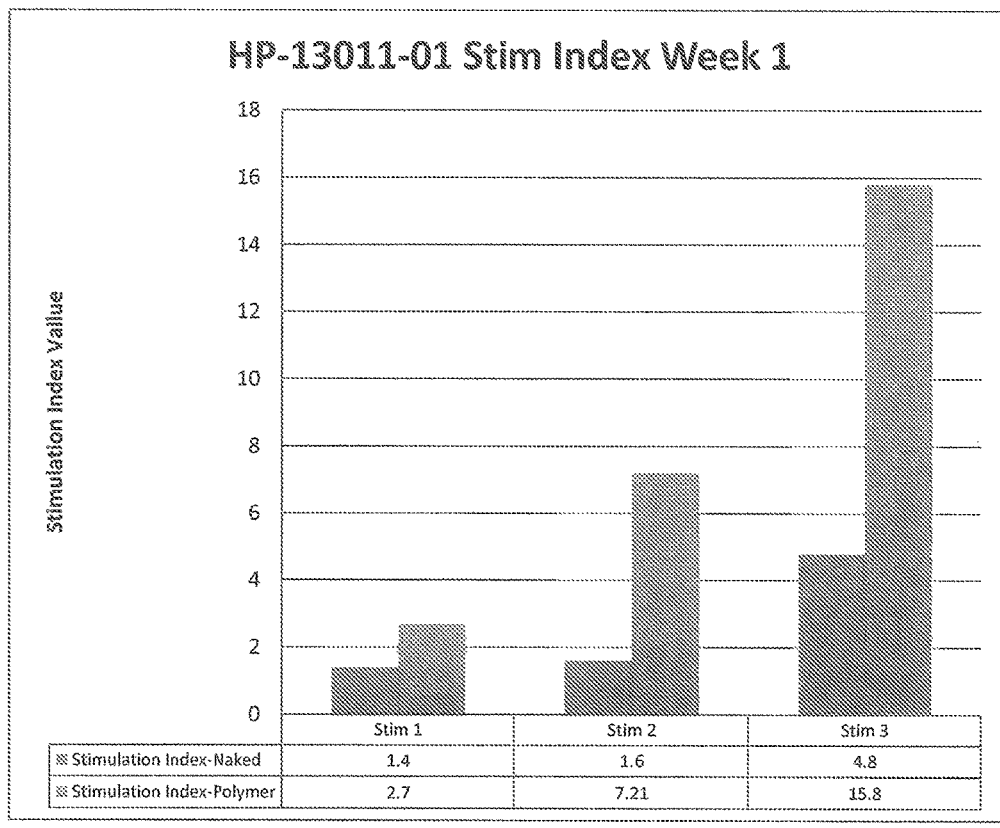
Figure 25:
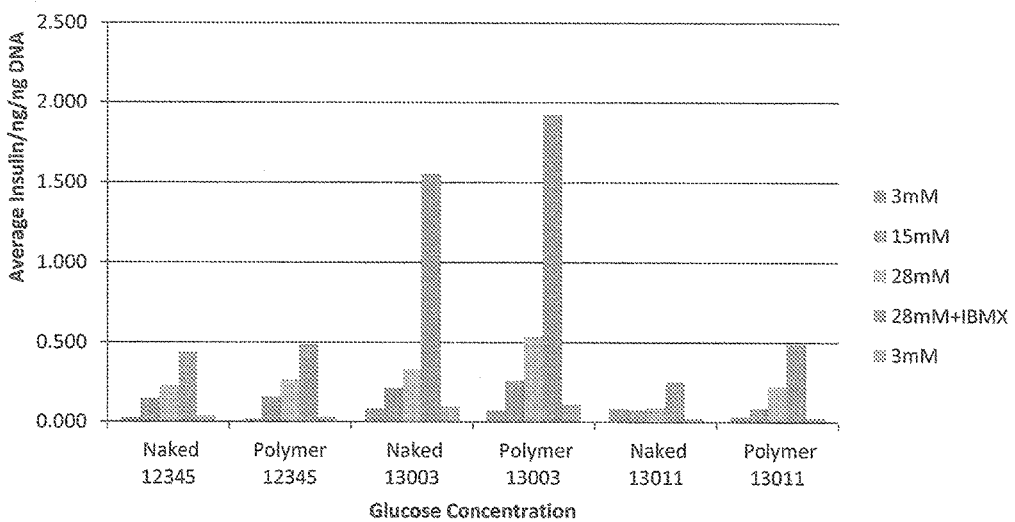
Figure 26:
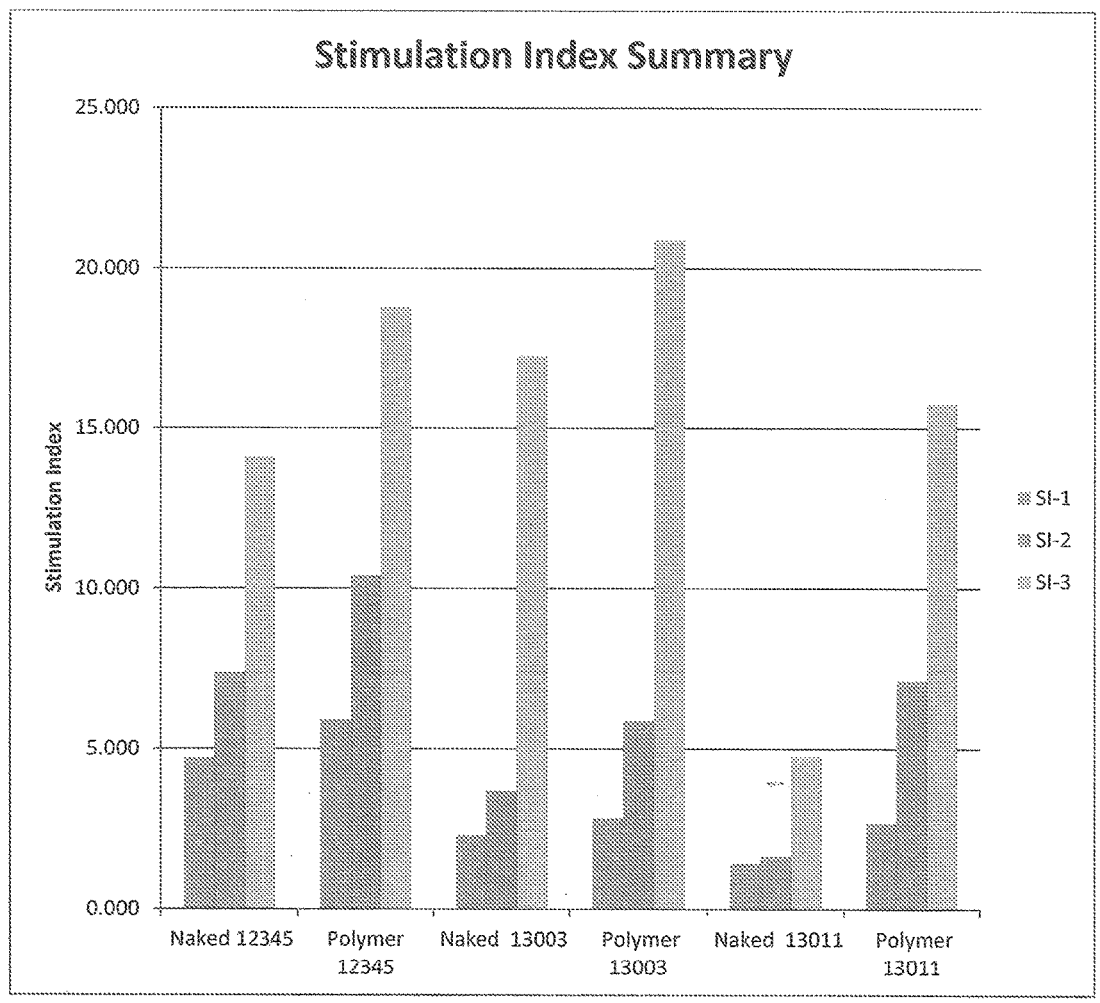
Figure 27:
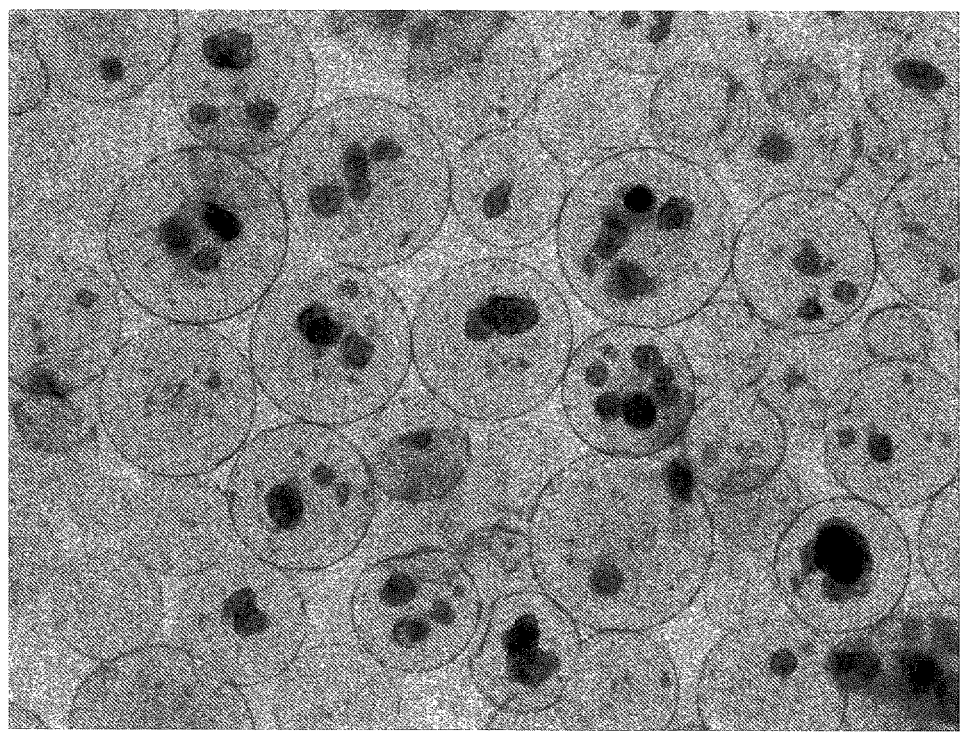
Figure 28:
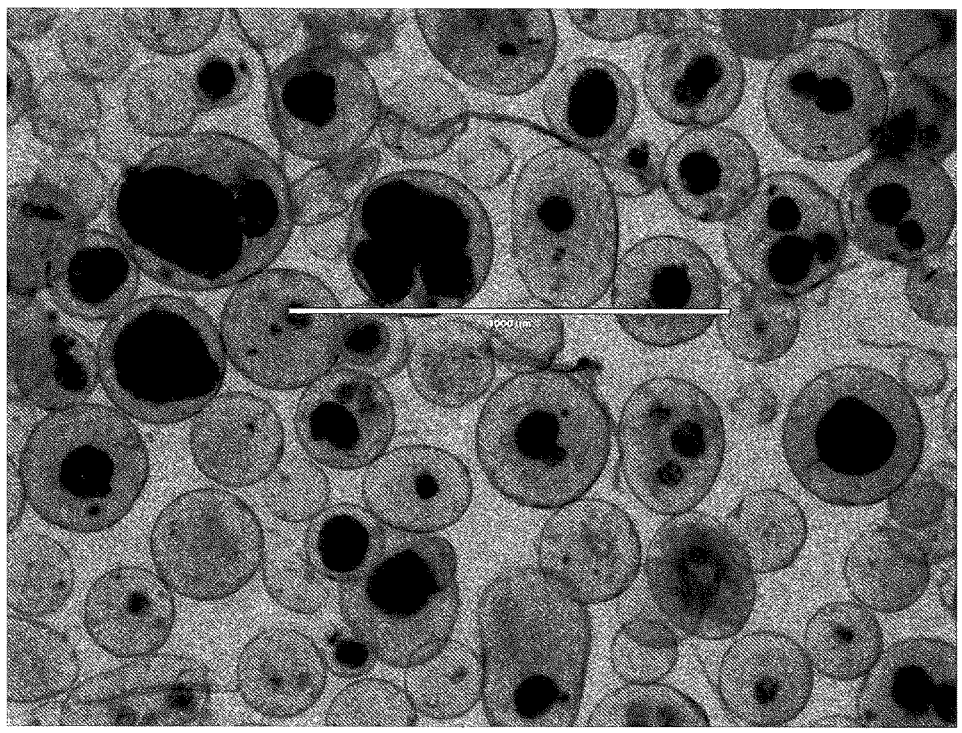
Figure 29:
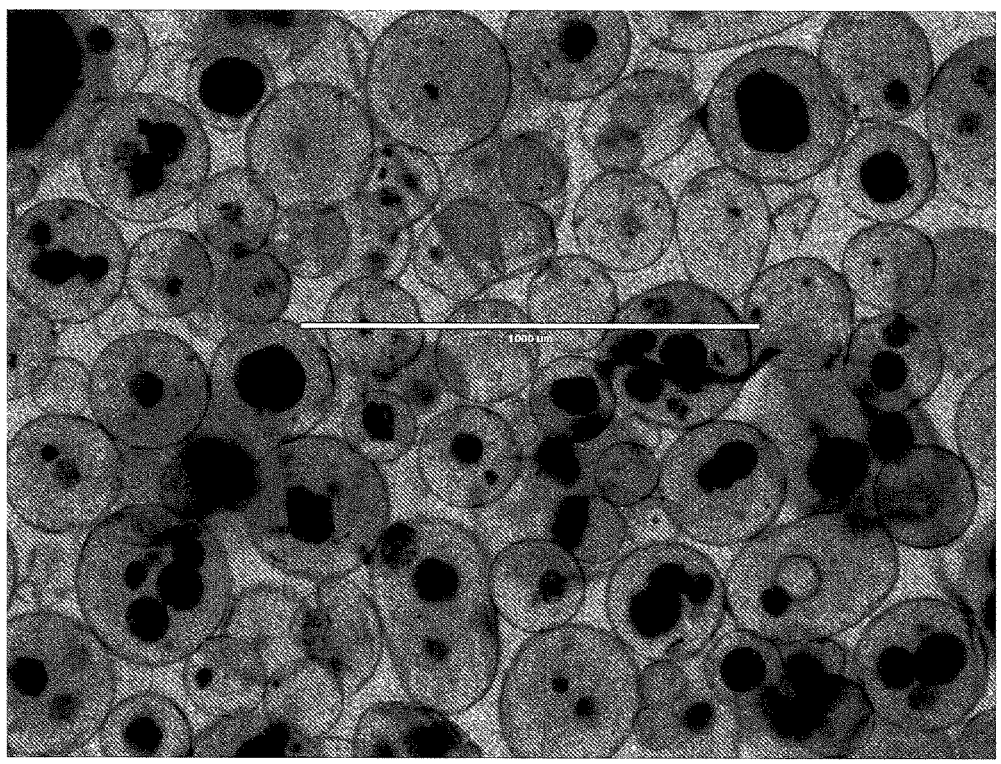
Figure 30:
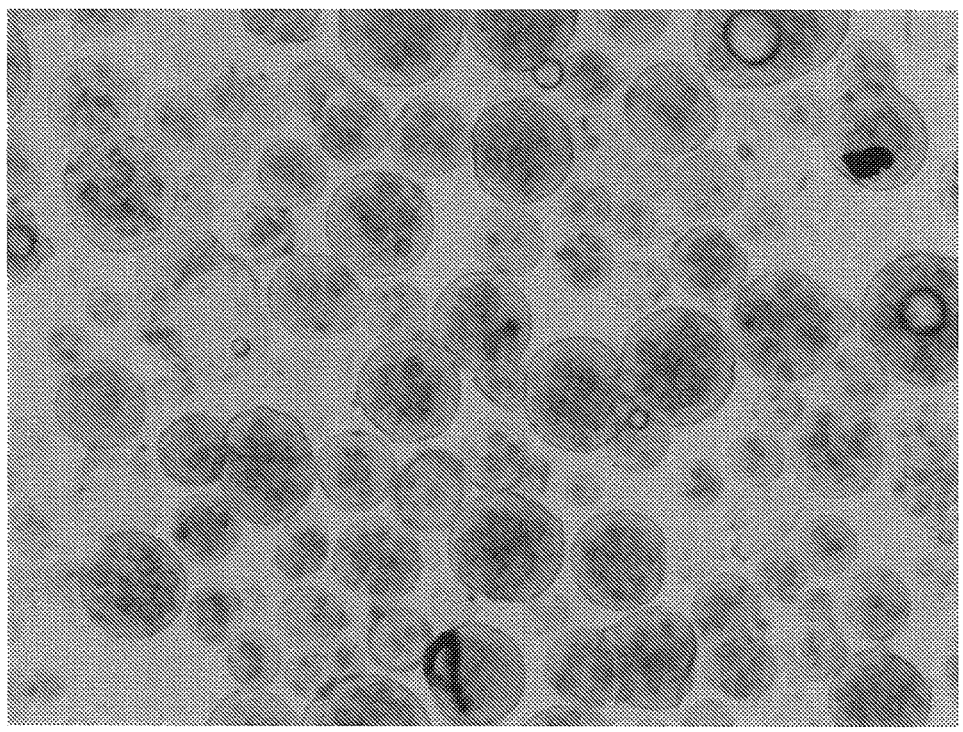
Figure 31:
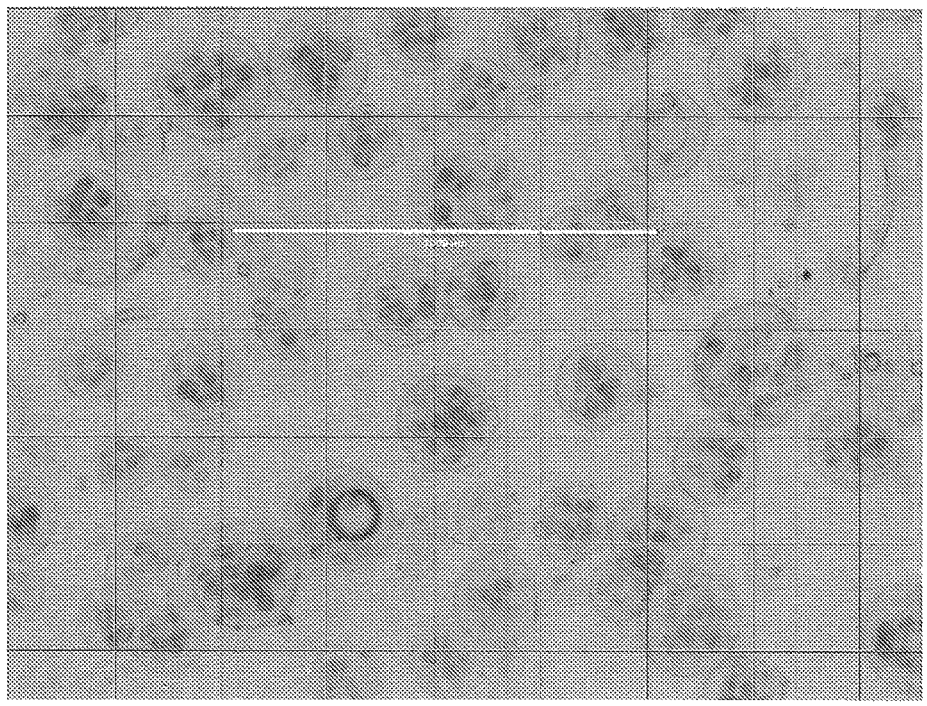
Figure 32:
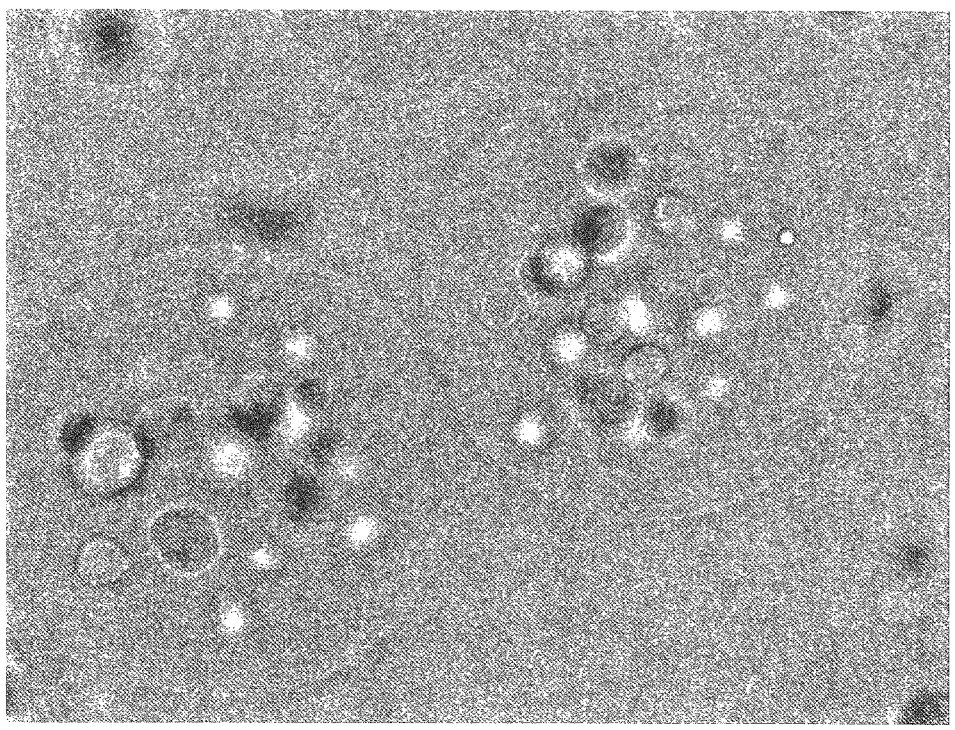
Figure 33:
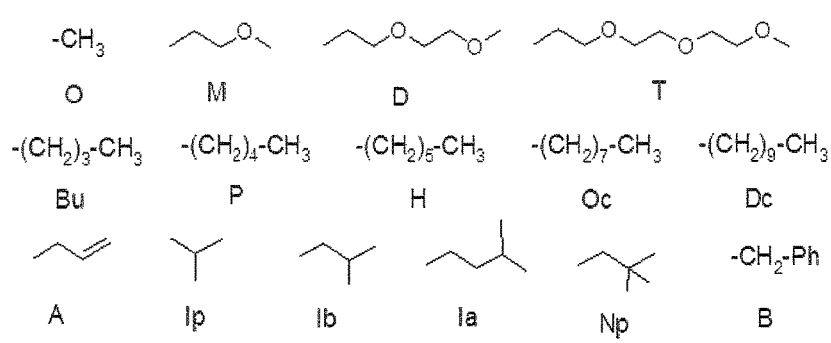
Figure 35:
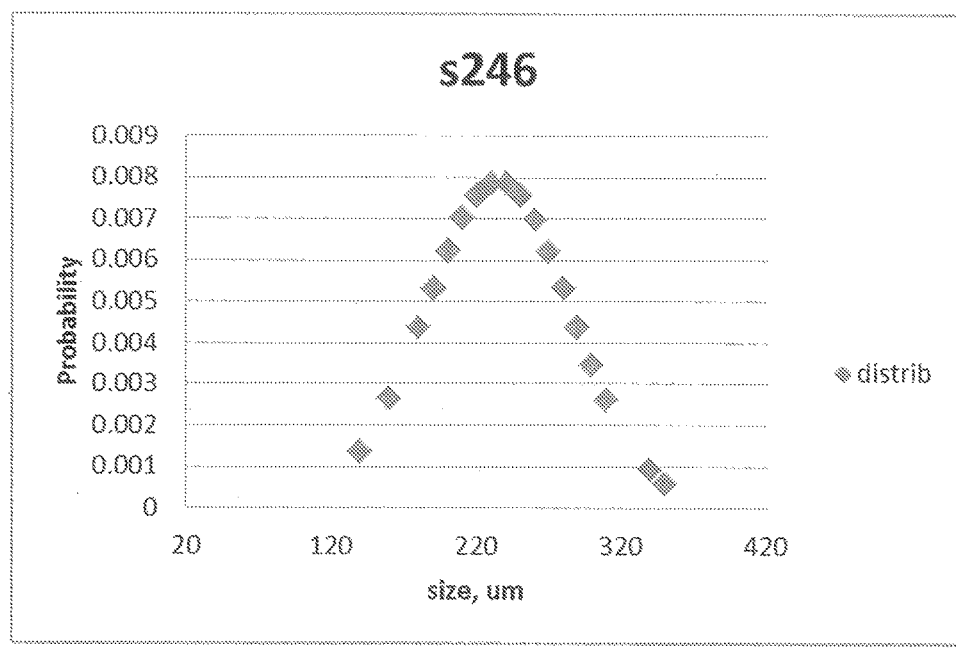

FIG. 17. Dithazone staining of naked islets.
FIG. 18. Dithazone staining of encapsulated islets.
FIG. 19. Viability staining of naked islets.
FIG. 20. Viability staining of encapsulated islets.
FIG. 21. Encapsulated islets, with bar showing 1000 micrometers (1000 μm).
FIG. 22. Encapsulated islets, with bar showing 4000 micrometers (4000 μm).
FIG. 23. Glucose Stimulate Insulin Release (GSIR) for week 1.
FIG. 24. Glucose Stimulate Insulin Release (GSIR) for week 1.
FIG. 25. Glucose Stimulate Insulin Release (GSIR) naked islet/polymer summary.
FIG. 26. Stimulation Index summary.
FIG. 27. Islet encapsulation.
FIG. 28. Islet fraction II.
FIG. 29. Islet fraction II.
FIG. 30. Encapsulation of human mesenchymal stem cells (hMSC).
FIG. 31. Encapsulation of human mesenchymal stem cells (hMSC).
FIG. 32. Encapsulation of human mesenchymal stem cells (hMSC).
FIG. 33. R groups of polymers of the present disclosure.
FIG. 34. Structures of exemplary monomers.
FIG. 35. Size distribution of capsules.

POLYMERS AND GELS

A hydrogel is a network of hydrophilic polymers that can swell in water and hold a large amount of water, while maintaining the structure of a 3-dimensional network. Where the polymer gels are not cross-linked, and if the polymer takes the form of a free-flowing liquid at room temperature, the polymer can be loaded with drug at ambient temperature, and then converted to a hydrogel by raising the temperature up to body temperature. Then, the hydrogel can be injected, where subsequent release of the drug occurs by mass action (diffusion out of the gel). In the absence of cross-linking, that is, where the polymer chains of the hydrogel are not cross-linked, changing environmental conditions can result in sol-gel transitions.

Where the polymer chains in the hydrogel are cross-linked, changing environmental conditions can result in swelling or in shrinking of the hydrogel. Where the pH of the environment can control the swelling or shrinking of a hydrogel, a hydrogel that contains a drug can be swallowed by a patient, where the hydrogel is shrunken at neutral pH. When the hydrogel enters the stomach and encounters acid, the acid provokes swelling, with the consequent release of the drug. See, e.g., Qiu and Park (2001) Adv. Drug Delivery Reviews. 53:321-339; Bromberg and Ron (1998) Adv. Drug Delivery Reviews. 31:197-221; Wei et al (2009) Biomaterials. 30:2606-2613.

A variety of polymers have been used for making capsules, and for encapsulating mammalian cells. These include polymers that are naturally occurring or that are derived from naturally-occurring polymers, such as, collagen, gelatin, chitosan, hyaluronic acid, alginate, agarose, and so on. Polymers that have been used for making capsules also include synthetic polymers, such as PEG/PEO, PVA, PPF/OPF, and others. See, e.g., Tan and Marra (2010) Materials. 3:1746-1767.

Some polymers form a gel with cooling, where gel formation can be reversed by warming, for example, warming to the original temperature. Other polymers form a gel with heating, where gel formation can be reversed by cooling, for example, cooling to the original lower temperature. Reversal of gel formation can be complete, or it can be partial. Gels exhibiting the above property are called thermoreversible gels. For example, carrageenan forms a random coil at elevated temperatures, but form a continuous network at cooler temperatures. In contrast, some types of cellulose derivatives form liquids at lower temperatures, but form gels at higher temperatures. The property of "sol-gel transitions" can be used for trapping reagents, such as mammalian cells, where the trap takes the form of the gel. In other words, cells can be encapsulated by mixing a soluble polymer with the cells, and then incubating at a reduced (or elevated) temperature, to stimulate gel formation and consequent encapsulation of the cells within the gel. In the case of alginate gels, for example, a reagent can be mixed with alginate at 20 degrees C., followed by incubation at 37 degrees C., where the elevated temperature resulted in encapsulation of the reagent (see, e.g., Westhaus and Messersmith (2001) Biomaterials. 22:453-462). To give another example, the polymer PEO-PPO-PEO occurs in soluble state at 4 degrees C., but when incubated at 37 degrees C., the result is formation of a gel. Depending on the concentration of the polymer used in the reaction mixture, maximal gel formation occurs within a few hours, or within a few days (see, e.g., Sosnik and Cohn (2004) Biomaterials. 25:2851-2858).

The present disclosure provides reagents, methods, and compositions such as encapsulated cells, and the like, involving thermal gelation. But the disclosure is not limited to thermal gelation. In addition, or as an alternative, the present disclosure provides reagents, methods, and compositions, where a gel or capsule is make using ionic gelation, physical self-assembly, photopolymerization, chemical crosslinking, or any combination of the above (see, e.g., Tan and Marra (2010) Materials. 3:1746-1767, which is hereby incorporated in its entirety). Ionic gelation has been used for crosslinking alginate and similar hydrogels, such as chitosan. Methods and instruments are available for measuring reversible gelation, and for measuring sol-gel transition temperatures (see, e.g., Kim et al (2009) Biomacromolecules. 10:2476-2481, which is hereby incorporated herein in its entirety).

The present disclosure provides a polymer, at least one polymer, mixtures of more than one polymer, and compositions thereof, including compositions that are encapsulated cells, where gelation is performed at a temperature that is conducted at 18° C., at 19° C., at 20° C., at 21° C., at 22° C., at 23° C., at 24° C., at 25° C., at 26° C., at 27° C., at 29° C., at 30° C., at 31° C., at 32° C., at 33° C., at 34° C., at 35° C., at 36° C., at 37° C., at 38° C., at 39° C., at 40° C., and the like, where transition from a lower temperature to the indicated temperature results in polymerization, gel formation, and if cells are present, in encapsulation of the cells. In range embodiments, the present disclosure provides a method gelation, and compositions formed therewith, performed in a temperature range that is 17-18° C., 18-19° C., 19-20° C., 20-21° C., 21-22° C., 22-23° C., 23-24° C., 24-25° C., 25-26° C., 26-27° C., 27-28° C., 29-30° C., 31-32° C., 33-34° C., 34-35° C., 36-37° C., 38-39° C., 39-40° C., and the like, or any combination of the above ranges, such as the range of 22-27° C. A preferred temperature for gel formation, is where the gel formation temperature is below body temperature (37° C.), in order to ensure that net loss of the gel does not occur in the body, that is, in the body after implantation. In a preferred embodiment, the Critical Solution Temperature of the polymer is lower than body temperature (37° C.) in order to ensure that the gel protects the encapsulated cells from the immune system, that is, after implantation.

Moreover, what is also encompassed is stepwise temperature procedure for gelation, for example, incubation at 20-21° C. for a period of three hours, followed by incubation at 29-30° C. for three hours.

Incubation times can be, for example, 10 minutes, 20 min, 30 min, 60 min (1 h), 90 min, 2 h, 3 h, 4 h, 5 h, 6 h, 8 h, 10 h, 12 h, 15 h, 18 h, 21 h, 24 h, or ranges, such as 20-30 min, 60-70 min, 90-120 min, 1-2 h, 2-3 h, 4-5 h, 5-6 h, 7-8 h, 9-10 h, 10-12 h, 15-16 h, 20-22 h, 22-24 h, 24-26 h, 26-28 h, 28-30 h, and so on, or any combination of the above, without implying any limitation.

Pore Size

The present disclosure provides a population of encapsulated cells, where at least 50% of the capsules are characterized as follows. The capsule has pores, where less than 80% of the pores allow for passage of a 400 kilodalton (kD) globular protein, where less than 70% of the pores allow for passage of a 400 kD globular protein, where less than 60% of the pores allow for passage of a 400 kD globular protein, where less than 50% of the pores allow for passage of a 400 kD globular protein, where less than 40% of the pores allow for passage of a 400 kD globular protein, where less than 30% of the pores allow for passage of a 400 kD globular protein, where less than 20% of the pores allow for passage of a 400 kD globular protein, where less than 10% of the pores allow for passage of a 400 kD globular protein, where less than 5% of the pores allow for passage of a 400 kD globular protein, and the like. Also, the present disclosure provides a population of encapsulated cells, where at least 60%, at least 70%, at least 80%, at least 90%, at least 95%, or at least 99%, of the capsules are characterized by one of the above parameters.

Pore size can be determined for a single empty capsule, for a population of empty capsules, for a single capsule that encapsulates at least one mammalian cell, for a population of capsules where at least 99% of the population of capsules encapsulates at least one mammalian cell, and so on. Pore size can be determined, for example, with globular proteins that are used as molecular weight markers, such as bovine serum albumin, ovalbumin, casein, RNase B, myoglobin, carbonic anhydrase. Antibodies, from one of the IgG, IgA, IgM, IgD, or IgE classes can be used for assessing pore size, and for assessing exclusionary properties of a capsule or population of capsules. In embodiments, a population of empty capsules, or a population of occupied capsules (occupied by at least one mammalian cell) can be defined in terms of the ratio of (test protein)/(control protein) that enters the capsule, where the unit is in terms of number of proteins entering. The control protein can small, e.g., 5,000 kd, so that free passage is expected limited only by diffusion rate, or the control protein can be extremely large, e.g., 1,000,000 kd, so that essentially zero proteins have detectably entered the capsule over a given time period, such as one hour.

For a given matrix that contains pores, it is conventional for the skilled artisan to use standard molecular weight markers, when determining the molecular weight of an unknown protein. Conventionally, the skilled artisan can use standard molecular weight markers for characterizing a matrix that contains pores. Methods using molecular weight markers can measure Stokes radius, which is sensitive to water of hydration that is associated with the matrix, and also to water of hydration that is associated with the protein. Standard molecular weight markers include ceruloplasmin, transferrin, bovine serum albumin, ovalbumin, carbonic anhydrase, trypsin inhibitor (see, e.g., Morris et al (1971) Biochem. J. 124:517-528; Le Maire et al (1987) Biochem. J. 43:399-404; Harlan et al (1995) Analyt. Biochem. 224:557-563). Pore size, as expressed in terms of molecular weight of standard proteins, has been used to characterize matrixes made of dextran polymers, and seaweed polymers, such as those used for making Sepharose® and Agarose®. Thus, the skilled artisan understands that molecular weight markers are the most direct way to determine pore size, where pores are hydrated and where proteins (or other macromolecules that may pass through the pores) are hydrated.

In some embodiments, the temperature used for gel formation is the same as the transition temperature for the polymer that is used. In other embodiments, the temperature used for gel formation is greater than that of the transition temperature, while in other embodiments, the temperature used for gel formation is lesser than the transition temperature.

The present disclosure provides a population of encapsulated cells, where at least 50% of the capsules are characterized as follows. The capsule has pores, where less than 80% of the pores allow for passage of a 200 kilodalton (kD) globular protein, where less than 70% of the pores allow for passage of a 200 kD globular protein, where less than 60% of the pores allow for passage of a 200 kD globular protein, where less than 50% of the pores allow for passage of a 200 kD globular protein, where less than 40% of the pores allow for passage of a 200 kD globular protein, where less than 30% of the pores allow for passage of a 200 kD globular protein, where less than 20% of the pores allow for passage of a 200 kD globular protein, where less than 10% of the pores allow for passage of a 200 kD globular protein, where less than 5% of the pores allow for passage of a 200 kD globular protein, and the like. Also, the present disclosure provides a population of encapsulated cells, where at least 60%, at least 70%, at least 80%, at least 90%, at least 95%, or at least 99%, of the capsules are characterized by one of the above parameters.

The present disclosure provides a population of encapsulated cells, where at least 50% of the capsules are characterized as follows. The capsule has pores, where less than 80% of the pores allow for passage of a 100 kilodalton (kD) globular protein, where less than 70% of the pores allow for passage of a 100 kD globular protein, where less than 60% of the pores allow for passage of a 100 kD globular protein, where less than 50% of the pores allow for passage of a 100 kD globular protein, where less than 40% of the pores allow for passage of a 100 kD globular protein, where less than 30% of the pores allow for passage of a 100 kD globular protein, where less than 20% of the pores allow for passage of a 100 kD globular protein, where less than 10% of the pores allow for passage of a 100 kD globular protein, where less than 5% of the pores allow for passage of a 100 kD globular protein, and the like. Also, the present disclosure provides a population of encapsulated cells, where at least 60%, at least 70%, at least 80%, at least 90%, at least 95%, or at least 99%, of the capsules are characterized by one of the above parameters.

The present disclosure provides a population of encapsulated cells, where at least 50% of the capsules are characterized as follows. The capsule has pores, where less than 80% of the pores allow for passage of a 70 kilodalton (kD) globular protein, where less than 70% of the pores allow for passage of a 70 kD globular protein, where less than 60% of the pores allow for passage of a 70 kD globular protein, where less than 50% of the pores allow for passage of a 70 kD globular protein, where less than 40% of the pores allow for passage of a 70 kD globular protein, where less than 30% of the pores allow for passage of a 70 kD globular protein, where less than 20% of the pores allow for passage of a 70 kD globular protein, where less than 10% of the pores allow for passage of a 70 kD globular protein, where less than 5% of the pores allow for passage of a 70 kD globular protein, and the like. Also, the present disclosure provides a population of encapsulated cells, where at least 60%, at least 70%, at least 80%, at least 90%, at least 95%, or at least 99%, of the capsules are characterized by one of the above parameters.

The present disclosure provides a population of encapsulated cells, where at least 50% of the capsules are characterized as follows. The capsule has pores, where less than 80% of the pores allow for passage of a 35 kilodalton (kD) globular protein, where less than 70% of the pores allow for passage of a 35 kD globular protein, where less than 60% of the pores allow for passage of a 35 kD globular protein, where less than 50% of the pores allow for passage of a 35 kD globular protein, where less than 40% of the pores allow for passage of a 35 kD globular protein, where less than 30% of the pores allow for passage of a 35 kD globular protein, where less than 20% of the pores allow for passage of a 35 kD globular protein, where less than 10% of the pores allow for passage of a 35 kD globular protein, where less than 5% of the pores allow for passage of a 35 kD globular protein, and the like. Also, the present disclosure provides a population of encapsulated cells, where at least 60%, at least 70%, at least 80%, at least 90%, at least 95%, or at least 99%, of the capsules are characterized by one of the above parameters.

Also provided, are the above exclusionary embodiments, where the molecular weight cutoff is 400 kD, 300 kD, 200 kD, 100 kD, 90 kD, 80 kD, 75 kD, 70 kD, 60 kD, 50 kD, 40 kD, 35 kD, 30 kD, 25 kD, 20 kD, 15 kD, 10 kD, and the like, or where the molecular weight cutoff is somewhat indistinct, and can be best expressed as a range such as, 400-420 kD, 380-400 kD, 360-380 kD, 340-360 kD, 320-340 kD, 300-320 kD, 280-300 kD, 260-280 kD, 240-260 kD, 220-240 kD, 200-220 kD, 180-200 kD, 160-180 kD, 140-160 kD, 120-140 kD, 100-120 kD, 80-100 kD, 60-80 kD, 50-60 kD, 40-50 kD, 30-40 kD, 20-30 kD, 15-20 kD, 10-15 kD, or any combination of the above ranges, for example, 20-40 kD.

The present disclosure provides reagents and methods, which can include Vascular Endothelial Growth Factor (VEGF), one or more VEGF analogues, or any reagent or drug that can stimulate vascularization. Also provided are exclusionary embodiments, where the reagents or methods do not include any VEGF, do not include any VEGF analogues, or do not include any reagent or drug that can stimulate vascularization. See, e.g, US 2007/0184023 of Birk et al, US 2007/0128197 of Andrew et al, and Fuh et al (1998) J. Biol. Chem. 273:11197-11204, each of which is hereby incorporated herein by reference in its entirety.

Regarding xenografts, the present disclosure provides one or more xenograft embodiments that comprise islets from one or more of non-human primate, monkey, ape, chimpanzee, baboon, prosimian, bovine, horse, sheep, goat, pig, dog, and the like. In exclusionary embodiments, the present disclosure can exclude one or more, or all, of the above xenograft embodiments. The xenograft can also be with pancreatic beta cells.

Identifying and Counting Cells

Techniques and equipment for measuring expression of biomarkers, and for identifying cells, include flow cytometry, histology, gene arrays, and reagents such as antibodies, enzyme-linked antibodies, fluorescent antibodies, poly- merase chain reaction (PCR), and the like. Guidance on flow cytometry is available (see, e.g., BD Biosciences, San Jose, Calif. (December 2007) BD FACSAria II User's Guide, part no. 643245, Rev. A (344 pages)). Cells can be identified, quantitated, and their states of activation, maturation, and differentiation, can be measured by flow cytometry, e.g., with FACS Caliber (BD Biosciences, San Jose, Calif.). Blood cells can be counted and identified, e.g., by a light microscope, hematology analyzer (e.g., Coulter LH500 Hematology Analyzer, Beckman Coulter), or by flow cytometry.

Cells to Encapsulate

The present disclosure provides reagents, encapsulated cells, and methods for preparing encapsulated cells and for administering the encapsulated cells, where the cell can be, for example a pancreatic beta cell, an islet of Langerhans, a stem cell, a lineage committed progenitor cells such as a unipotent cell, a bipotent cell, a tripotent cell, a multipotent cell, or a lineage-uncommitted pluripotent stem cell, such as pluripotent mesodermal stem cells (PPMSC), or $CD10^+$, $CD66e^+$ cells (see, Young and Black (2004) Anatomical Record Part A. 276A:75-192).

What is also encompassed are subcategories for pluripotent stem cells, such as, epiblastic-like stem cells, ectodermal stem cells, surface ectodermal stem cells, neuroectodermal stem cells, neural tube stem cells, neural crest stem cells, mesodermal (mesenchymal) stem cells, paraxial mesodermal stem cells, intermediate mesodermal stem cells, lateral plate mesodermal stem cells, and endodermal stem cells. Biomarker expression profiles for multipotent mesenchymal stomal cells (MSCs) are provided by, e.g., Dominici et al (2000) Cytotherapy. 8:315-117. DiGirolamo et al (1999) Brit. J. Haemotol. 107:275-281, describes various terms that have been used to refer to MSCs. Vodyanik et al (2010) Cell Stem Cell. 7:718-729, defines relation between mesodermal cells and mesenchymal stem cells. The present disclosure also encompasses Very Small Embryonic-Like (VSELs) stem cells (see, e.g., Kassmer and Krause (April 2013) Molecular Reproduction and Development; Zuba-Surma et al (2009) Cytometry A. 75:4-13; Ratajczak et al (2011) Exp. Hematol. 39:225-237).

Also provided are encapsulated bone marrow stromal cells, encapsulated hepatocytes, encapsulated neural stem cells, encapsulated mesenchymal stem cells (MSC), encapsulated neural stem cells (NSC), encapsulated umbilical cord derived stem cells, encapsulated adipose derived stem cells (ASC), encapsulated myoblasts, encapsulated chondrocytes, encapsulated immune cells (e.g., T cells, NK cells, dendritic cells, B cells), encapsulated cells that express and secrete hormones, antibodies, growth factors, and so on, encapsulated recombinant cells, encapsulated cells that are used to treat genetic disorders, such as enzyme deficiency diseases (e.g., phenylketonuria), encapsulated cancer cells, and so on.

Inflammation

The present disclosure provides reagents, polymers, encapsulated cells, capsules, and related method that result in reduced inflammation. Reduced inflammation can be assessed, for example, by comparing with inflammation induced by an implant that comprises alginate, carrageenan, polyornithine, and so on. Compositions, reagents, and methods of the present disclosure, provide an inflammation that is below the level of detection, or that is less than 80%, less than 70%, less than 60%, less than 50%, less than 40%, less than 30%, less than 20%, less than 10%, less than 5%, less than 2%, less than 1%, of a comparator composition, reagent, or method. The comparator composition can be that used in a historic control. Historic controls are described (Brody, T. (2012) *Clinical Trials (Study Design, Endpoints and Biomarkers, Drug Safety, and FDA and ICH Guidelines)*, Elsevier/Academic Press, 650 pages, pages 20, 109, 131).

Inflammation can be assessed over a time period, beginning with the date of implantation to the time of assessment. For example, inflammation can be assessed over a time period that is day zero to 2 days (0-2 days), 0-4 days, 0-8 days, 0-20 days, 0-30 days, 0-40 days, 0-50 days, 0-60 days, 0-120 days, 0-365 days, and so on. The term "inflammation" refers to pathological accumulation in the number of one or more types of immune cells, or the pathological activation of one or more types of immune cells. Cells of the immune system include $CD8^+$ T cells, $CD4^+$ T cells, myeloid dendritic cells (DCs), plasmacytoid DCs, B cells, NK cells, and NK T cells. Immune cells are described, e.g., in US 2007/0207170 of Dubensky et al, which is incorporated herein by reference in its entirety.

Methods are available for detecting formation of a fibrous capsule in response to an implant. Fibrous capsules can include inflammatory cells, such as macrophages, lymphocytes, and plasma cells (Katzin et al (1996) Clin. Diagnostic Lab. Immunol. 3:156-161). Inflammatory cells can be identified by histological methods, by flow cytometry, and by assays such as ELISPOT assays and tetramer staining for T cells, and chromium release assays for NK cell. Methods are available for assessing implant-induced inflammation by mast cells, monocytes, macrophages, neutrophils, granuloma cells, fibroblasts, fibroblast-like cells, and fibrocytes (see, e.g., Tang et al (1998) Proc. Natl. Acad. Sci. USA. 95:8841-8846; Thevenot et al (2011) Biomaterials. 32:8394-8403; Bonney et al (1978) J. Exp. Med. 148:261-275). Fibrosis can be assessed with Masson Trichrome and Picrosirius Red staining.

Definitions and Methods

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition. "Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. See, e.g., U.S. Pat. No. 5,888,530 issued to Netti, et al, which is incorporated herein by reference.

"Expression" in an "effective amount" encompasses, but is not limited to, a level of expression of a biochemical that is sufficient to result in a detectable increase in the level of the biochemical in the bloodstream, or that is sufficient to stimulate the biochemical's receptor (in the event that the biochemical has a receptor), or that is sufficient to synergize with an existing level of the biochemical in the bloodstream to stimulate the biochemical's receptor. Without implying any limitation, the biochemical can be insulin.

"Expression" can refer, without implying any limitation, to the biosynthesis of a nucleic acid such as mRNA, or to the biosynthesis of a polypeptide. Expression can refer to the absolute amount of a nucleic acid or polypeptide. Also, expression can refer to the absolute amount of a nucleic acid or polypeptide, with reference to a comparator expression. A comparator expression can be that under a different metabolic condition, under a different nutritional condition, under a different genetic background, under a different pharmaceutical condition, and so on. Expression can also refer to the rate of expression, for example, number of molecules of mRNA biosynthesized per minute, or number of molecules of mRNA that accumulates per minute, or milligrams of polypeptide synthesized per minute, or milligrams of polypeptide that accumulates per minute. Expression also can refer to the transfer of an existing polypeptide from the interior of a cell to the cell's surface, as in protein secretion, or as in the insertion of proteins into the plasma membrane. Expression can also refer to rate of transfer, or in terms of absolute transfer, of a substance from inside a cell to the bloodstream or other extracellular fluid, or from inside an organ to the bloodstream or other extracellular fluid. Techniques for measuring expression are available, for example, TaqMan® assays for mRNA expression, real time PCR, and Western blots for polypeptide expression (see, e.g., Maurin (2012) Expert Rev. Mol. Diag. 12:731-754; Naour (2001) Proteomics. 1:1295-1302; Naour (2002) Technol. Cancer Res. Treat. 1:257-262; Devonshire (2013) Methods. 59:89-100; Jensen (2012) Anatomical Record. 295:1-3).

"Islet Equivalents" (IEQ) is defined as follows. Islets have a wide variety of sizes. When one documents the numbers of islets from a process by counting them, the counts are made specifically for different sizes, that is, 50-100 microns, 100-200 microns, 200-300 microns, 300-400 microns, and >400 microns. Then the formula for a sphere is used to multiply the actual count for each size. For example, the number of islets 50-100 microns is ×0.125, the number from 100-200 microns is ×1.0. The number from 200-300 microns is ×4.63. The number from 300-400 microns is ×12.7. The number from greater than 400 microns is 20.8. These counts are then added and calculated for the volume they are in. The final IEQ count represents the numbers of islets there would be if all of the islets were 150 microns in diameter.

"Metabolism" of a cell, tissue, organ, animal, human subject, and the like, can be assessed by a number of techniques. Metabolism can be assessed by measuring electron transport, by measuring a particular redox reaction, by measuring the transport of an amino acid, cation, or anion, by measuring activity of ion channels, by measuring nucleic acid metabolism, by measuring uptake of oxygen or generation of carbon dioxide, and so on. Weaver et al (1998) J. Biol. Chem. 273:1647-1653, discloses methods to measure amino acid uptake by islets. Pedraza et al (2012) Proc. Natl. Acad. Sci. 109:4245-4250 describes methods to redox activity of islets using tetrazolium dyes. Larsson et al (1996) J. Biol. Chem. 271:10623-10626 and Martin et al (1999) Diabetes. 48:1954-1961 discloses methods for measuring insulin secretion by islets. Martin et al, supra, discloses methods for assaying ion channels. "Metabolically active" can be characterized by a cut-off point where metabolism of a population of islets is at least 20%, at least 30%, at least 40%, at least 50%, at least 60%, at least 70%, at least 80%, at least 90%, at least 95%, as active as with a comparator population of islet cells. For example, the comparator population may be an isolated population of non-encapsulated islets freshly prepared from a biopsy.

"Naked islets" refers to islets that do not have a non-natural coating. "Non-natural" coating refers to coatings of naturally occurring polymers, such as alginate, and also to coatings of synthetic polymers, such as polyethylene glycol. Alginate, when used as a coating for islets, is non-natural, because mammals having islets with an alginate coating do not occur naturally. For the present disclosure, "coating" is not limited to coatings that are polymers.

Methods and reagents for preparing islets are available, e.g., islets from human, primate, dog, pig, bovine, hamster, or rat. See, e.g., Marchetti et al (1991) Transplantation. 52:209-213; Ricordi et al (1988) Diabetes. 37:413-420; Rouiller et al (1990) Exp. Cell Res. 191:305-312; Halberstadt et al (2013) Methods Mol. Biol. 1001:227-259; Lacy et al (1982) Diabetes. 31:109-111; Rosenberg et al (1988) J. Surgical Res. 44:229-234; Korbutt et al (1996) J. Clin. Invest. 97:2119-2129; Gaur (2004) ILAR J. 45:324-333.

"Stimulation Index" refers to the ratio of (stimulated release of insulin)/(basal release of insulin). Stimulation can be assessed in tests where the stimulant is, for example, glucose, an amino acid, a synthetic reagent, and the like, and combinations thereof (see, e.g., Floyd et al (1996) J. Clin. Inv. 45:1487-1502). The "basal" condition can optionally be defined in terms of a basal level of glucose. Unless specified otherwise, the Stimulation Index is determined by in vitro experiments, such as with isolated islets in a medium. For example, Stimulation Index can be calculated by ratio of (insulin release with 12 mM glucose)/(insulin release at 3 mm glucose). Alternatively, Stimulation Index can be calculated by ratio of (insulin release with 20 mM glucose)/(insulin release at 3 mm glucose). Also, Stimulation Index can be calculated by ratio of (insulin release with 20 mM glucose+IBMX)/(insulin release at 3 mm glucose).

Use of a defined concentration of glucose as the "basal" level, where this concentration is somewhat elevated beyond the expected or actual basal level, can provide data that is more consistent and more likely to result in meaningful interpretations.

The present disclosure provides encapsulated islets, where insulin expression is characterized by a Stimulation Index that is at least 20% greater than a Stimulation Index of naked islets, and where the Stimulation Index is calculated by the ratio of (insulin stimulation with 20 mM glucose)/(insulin stimulation with 3.0 mM glucose). Also, the present disclosure provides encapsulated islets, where insulin expression is characterized by a Stimulation Index that is at least 25% greater, or at least 30% greater, or at least 35% greater, or at least 40% greater, or at least 45% greater, or at least 50% greater, or at least 55% greater, or at least 60% greater, or at least 65% greater, or at least 70% greater, or at least 75% greater, and the like, than a Stimulation Index of naked islets, and where the Stimulation Index is calculated by the ratio of (insulin stimulation with 20 mM glucose)/(insulin stimulation with 3.0 mM glucose).

An "extracellular fluid" can encompass, e.g., serum, plasma, blood, interstitial fluid, cerebrospinal fluid, secretions, milk, chyme, lymph, bile, sweat, and urine. An "extracellular fluid" can comprise a fluid-like colloid or a fluid-like suspension, e.g., whole blood, non-coagulated plasma, or plasma with an effective anti-coagulant.

A composition that is "labeled" is detectable, by spectroscopic, photochemical, biochemical, immunochemical, isotopic, or chemical methods. For example, labels include radioactive isotopes of phosphorous, iodine, sulfur, carbon, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

The present disclosure encompasses storing a population of capsules in a medical device that is capable of mediating transfer of the population of capsules to a location in the mammalian subject that is inside the body of the mammalian subject. The storing can be for a few seconds, for a minute or so, for several minutes, or for an hour or longer. The medical device can comprise a syringe, a catheter, a needle, a valve, a surgical blade, and so on.

Centered Embodiments

An encapsulated cell, an encapsulated group of cells, or one or more encapsulated pancreatic islets, can be considered to be centered if one or more of the following criteria are met, without implying any limitation. The following uses the non-limiting example of a pancreatic islet. A photograph is taken of the encapsulated islet. The photograph reveals a cross-section of the islet, where the cross-section occurs at the circumference of greatest diameter. The photograph also reveals the luminal surface of the capsule, that is, the inner surface of the capsule. Also, the photograph reveals a distance between the inner surface and the border of the islet. In one embodiment, a centered islet is where at least 50% of the outside surface of the islet is at least 1 micrometer (um) away from the luminal surface. (This value of 50% need not be continuous. It may be segmented.) In another embodiment, at least 60%, at least 70%, at least 80%, at least 90%, at least 95%, at least 99%, or 100%, of the outside surface of the islet is at least 1 micrometer away from the luminal surface. In alternative embodiments, the distance is at least 0.25 um, at least 0.5 um, at least 2 um, at least 4 um, at least 6 um, at least 8 um, at least 10 um, at least 15 um, at least 20 um, at least 25 um, at least 30 um, at least 40 um, at least 50 um, at least 60 um, at least 70 um, at least 80 um, at least 90 um, at least 100 um, at least 200 um, and so on.

In other alternative embodiments, the distance is 0.25-1.0 micrometers (um), 0.25-2.0 um, 0.25-5.0 um, 0.25-10 um, 0.25-20 um, 0.5-2.0 micrometers (um), 0.5-5.0 um, 0.5-10 um, 0.5-20 um, 0.5-50 um, 0.5-100 um, 0.5-200 um, 1.0-2.0 um, 1.0-5.0 um, 1.0-10 um, 1.0-20 um, 1.0-50 um, 1.0-100 um, 2.0-5.0 um, 2.0-10 um, 2.0-15 um, 2.0-20 um, 2.0-50 um, 2.0-100 um, 5-10 um, 5-15 um, 5-20 um, 5-50 um, 5-100 um, 10-20 um, 10-50 um, 10-100 um, 10-200 um, as well as the ranges of 20-40 um, 20-50 um, 20-100 um, 20-150 um, 20-200 um, and so on.

The present disclosure encompasses a population of polymeric capsules, where at least 30%, at least 40%, at least 50%, at least 60%, at least 70%, at least 80%, at least 90%, or at least 95%, and the like, of the capsules in the population comprise at least one encapsulated mammalian islet, and wherein at least 50% of the capsules that comprise at least one encapsulated mammalian islet comprise at least one encapsulated mammalian islet that is centered in the capsule.

The present disclosure encompasses a population of polymeric capsules, where at least 30%, at least 40%, at least 50%, at least 60%, at least 70%, at least 80%, at least 90%, or at least 95%, and the like, of the capsules in the population comprise at least one encapsulated mammalian islet, and wherein at least 60% of the capsules that comprise at least one encapsulated mammalian islet comprise at least one encapsulated mammalian islet that is centered in the capsule.

The present disclosure encompasses a population of polymeric capsules, where at least 30%, at least 40%, at least 50%, at least 60%, at least 70%, at least 80%, at least 90%, or at least 95%, and the like, of the capsules in the population comprise at least one encapsulated mammalian islet, and wherein at least 70% of the capsules that comprise at least one encapsulated mammalian islet comprise at least one encapsulated mammalian islet that is centered in the capsule.

The present disclosure encompasses a population of polymeric capsules, where at least 30%, at least 40%, at least 50%, at least 60%, at least 70%, at least 80%, at least 90%, or at least 95%, and the like, of the capsules in the population comprise at least one encapsulated mammalian islet, and wherein at least 80% of the capsules that comprise at least one encapsulated mammalian islet comprise at least one encapsulated mammalian islet that is centered in the capsule.

The present disclosure encompasses a population of polymeric capsules, where at least 30%, at least 40%, at least 50%, at least 60%, at least 70%, at least 80%, at least 90%, or at least 95%, and the like, of the capsules in the population comprise at least one encapsulated mammalian islet, and wherein at least 90% of the capsules that comprise at least one encapsulated mammalian islet comprise at least one encapsulated mammalian islet that is centered in the capsule.

Molecular Weight Exclusion Embodiments

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 30% of the capsules that comprise the at least one encapsulated mammalian islet are capable of excluding a globular protein of a molecular weight of at least 50 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 50% of the capsules that comprise the at least one encapsulated mammalian islet are capable of excluding a globular protein of a molecular weight of at least 50 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 60% of the capsules that comprise the at least one encapsulated mammalian islet are capable of excluding a globular protein of a molecular weight of at least 50 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 70% of the capsules that comprise the at least one encapsulated mammalian islet are capable of excluding a globular protein of a molecular weight of at least 50 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 80% of the capsules that comprise the at least one encapsulated mammalian islet are capable of excluding a globular protein of a molecular weight of at least 50 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 30% of the capsules that comprise the at least one encapsulated mammalian islet are capable of excluding a globular protein of a molecular weight of at least 100 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 50% of the capsules that comprise the at least one encapsulated mammalian islet are capable of excluding a globular protein of a molecular weight of at least 100 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 60% of the capsules that comprise the at least one encapsulated mammalian islet are capable of excluding a globular protein of a molecular weight of at least 100 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 70% of the capsules that comprise the at least one encapsulated mammalian islet are capable of excluding a globular protein of a molecular weight of at least 100 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 80% of the capsules that comprise the at least one encapsulated mammalian islet are capable of excluding a globular protein of a molecular weight of at least 100 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 30% of the capsules that comprise the at least one encapsulated mammalian islet are capable of excluding a globular protein of a molecular weight of at least 150 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 50% of the capsules that comprise the at least one encapsulated mammalian islet are capable of excluding a globular protein of a molecular weight of at least 150 kilodaltons.

The present disclosure provides population of a polymeric capsule, where at least 30%, at least 40%, at least 50%, at least 60%, at least 70%, at least 80%, at least 90%, or at least 95%, of the capsule The present disclosure encompasses population of the above polymeric capsule, wherein the increased expression of insulin is characterized by a Stimulation Index that is at least 20% greater than a Stimulation Index of naked islets, and wherein the Stimulation Index is calculated by the ratio of (insulin stimulation with 20 mM glucose)/(insulin stimulation with 3.0 mM glucose). The present disclosure also encompasses the above population of polymeric capsule, wherein the increased expression of insulin is characterized by a Stimulation Index that is at least 40% greater than a Stimulation Index of naked islets, and wherein the Stimulation Index can be calculated by the ratio of (insulin stimulation with 20 mM glucose)/(insulin stimulation with 3.0 mM glucose). What is provided, is a population of encapsulated islets that comprises at least one encapsulated mammalian islet, and wherein at least 60% of the capsules that comprise the at least one encapsulated mammalian islet are capable of excluding a globular protein of a molecular weight of at least 150 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 70% of the capsules that comprise the at least one encapsulated mammalian islet are capable of excluding a globular protein of a molecular weight of at least 150 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 80% of the capsules that comprise the at least one encapsulated mammalian islet are capable of excluding a globular protein of a molecular weight of at least 150 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 30% of the capsules that comprise the at least one encapsulated mammalian islet are capable of excluding a globular protein of a molecular weight of at least 200 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 50% of the capsules that comprise the at least one encapsulated mammalian islet are capable of excluding a globular protein of a molecular weight of at least 200 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 60% of the capsules that comprise the at least one encapsulated mammalian islet are capable of excluding a globular protein of a molecular weight of at least 200 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 70% of the capsules that comprise the at least one encapsulated mammalian islet are capable of excluding a globular protein of a molecular weight of at least 200 kilodaltons.

The present disclosure provides population of a polymeric capsule, where at least 30%, at least 40%, at least 50%, at least 60%, at least 70%, at least 80%, at least 90%, or at least 95%, of the capsules in the population comprise at least one encapsulated mammalian islet, and wherein at least 80% of the capsules that comprise the at least one encapsulated mammalian islet are capable of excluding a globular protein of a molecular weight of at least 200 kilodaltons.

In addition to the above cutoff points, other useful exclusionary cutoff points include, for example, 5 kD, 10 kD, 20 kD, 30 kD, 40 kD, 60 kD, 70 kD, 80 kD, 90 kD, 125 kD, 175 kD, 225 kD, 250 kD, 275 kD, 300 kD, and so on.

Stimulation Index Embodiments

In non-limiting embodiments, the present disclosure provides a population of polymeric capsules, wherein the increased expression of insulin is characterized by a Stimulation Index that is at least 10% greater, at least 20% greater, at least 30% greater, at least 40% greater, at least 50% greater, at least 60% greater, at least 70% greater, at least 80% greater, at least 90% greater, at least 100% greater (2-fold greater), at least 125% by the ratio of (insulin stimulation with 20 mM glucose)/(insulin stimulation with 0.5 mM glucose); greater, at least 150% greater, at least 200% greater (3-fold greater), and the like, than a Stimulation Index of naked islets, and wherein the Stimulation Index can be calculated by the ratio of (insulin stimulation with 20 mM glucose)/(insulin stimulation with 3.0 mM glucose).

In alternative experiments, Stimulation Index can be calculated by the ratio of (insulin stimulation with 20 mM glucose)/(insulin stimulation with 0.0 mM glucose); by the ratio of (insulin stimulation with 20 mM glucose)/(insulin stimulation with 0.5 mM glucose); by the ratio of (insulin stimulation with 20 mM glucose)/(insulin stimulation with 1.0 mM glucose); by the ratio of (insulin stimulation with 20 mM glucose)/(insulin stimulation with 2.0 mM glucose); by the ratio of (insulin stimulation with 20 mM glucose)/(insulin stimulation with 3.0 mM glucose); by the ratio of (insulin stimulation with 20 mM glucose)/(insulin stimulation with 4.0 mM glucose); by the ratio of (insulin stimulation with 20 mM glucose)/(insulin stimulation with 5.0 mM glucose); and so on. The concentrations for glucose refer to the concentration added by the researcher, and do not take into account endogenous glucose that are present in any cells or associated fluids.

In alternative experiments, Stimulation Index can be calculated by the ratio of (insulin stimulation with 10 mM glucose)/(insulin stimulation with 0.0 mM glucose); by the ratio of (insulin stimulation with 10 mM glucose)/(insulin stimulation with 0.5 mM glucose); by the ratio of (insulin stimulation with 10 mM glucose)/(insulin stimulation with 1.0 mM glucose); by the ratio of (insulin stimulation with 10 mM glucose)/(insulin stimulation with 2.0 mM glucose); by the ratio of (insulin stimulation with 10 mM glucose)/(insulin stimulation with 3.0 mM glucose); by the ratio of (insulin stimulation with 10 mM glucose)/(insulin stimulation with 4.0 mM glucose); by the ratio of (insulin stimulation with 10 mM glucose)/(insulin stimulation with 5.0 mM glucose); and so on. The concentrations for glucose refer to the concentration added by the researcher, and do not take into account endogenous glucose that are present in any cells or associated fluids.

Instead of using 20 mM glucose or 10 mM glucose, as outlined above, Stimulation Index can also be calculated using, for example, the numerator concentration of glucose is greater than the denominator concentration of glucose by, for example, 1.0 mM, 2.0 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, and so on. Stimulation Index can also be defined in terms of experiments that involve amino acids, that is, where two different sets of islets are incubated in parallel with two different concentrations of a particular amino acid (see, e.g., Floyd et al (1966) J. Clin. Inv. 45:1487-1502).

Detailed Description

Guidance for inducing diabetes in experimental animals, implanting encapsulated islets in experimental animals or in human subjects, measuring insulin response, e.g., expression of C-peptide and glucose tolerance tests, measuring glycated hemoglobin for assessing long-term blood glucose levels, and methods for determining permeability of capsules, are disclosed in U.S. Pat. No. 7,427,415 of Scharp, which is incorporated herein by reference in its entirety. Salts, buffers, silicone oil, mineral oil, and other reagents, can be acquired from, for example, Sigma Aldrich (St. Louis, Mo.), Fischer Scientific (Hanover Park, Ill.), Life Technologies (Carlsbad, Calif.). Silicone oils, such as cyclomethicone, is available from, e.g., Dow Corning, Corning N.Y.; Lubrizol, Cleveland, Ohio; Clearco Products, Bensalem, Pa. Cyclomethicone contains decamethylcyclopentasiloxane.

Filters, such as Surfactant-Free Cellulose Filters (SFCA), IKA RW 20 Digital Mixers, and other mixers, freezers, temperature probes, pumps, rheometers (viscometers), pH meters, osmometers, and such, are available, for example from Cole-Parmer, Vernon Hills, Ill.; Corning Inc., Corning, N.Y.; Fischer Scientific, Hanover Park, Ill.; Whirlpool Corp., Benton Harbor, Mich.; Brookfield Engineering Laboratories, Middleboro, Mass.; Beckman Coulter, Brea, Calif.; Advanced Instruments, Norwood, Calif. Wettability of films, including crosslinked films and non-crosslinked films, can be measured by contact angle measurement (VCA Optima, AST Products, Inc., Billerica, Mass.) as applied, for example, by Hillberg et al (2012) J. Biomed. Mater. Res. Part B. 101B:258-268. Compressive strength of capsules can be measured, for example, by a surface texture analyzer, yielding the burst force (g) per capsule (see, Hillberg et al, supra).

Gel-sol Transition Temperatures

The gel/sol transition temperature of preferred hydrogel embodiments, occur at transition temperatures of 24, 28 or 32° C. Gel polymer with 24-26° C. transition temperature can be measured as a 15% solution in phosphate buffered saline (PBS). Other hydrogen embodiments that are contemplated have a transition temperature, for example, at 18° C., 19° C., 20° C., 21° C., 22° C., 23° C., 25° C., 26° C., 27° C., 29° C., 30° C., 31° C., 33° C., 34° C., 35° C., and the like, without implying any limitation.

Opening Capsules

Capsules can be opened by chilling at 4° C., and incubating at 4° C. for at least 6 hours, at least 12 hours, at least 18 hours, at least 24 hours, at least 30 hours, at least 36 hours, and so on. Empty capsules can be opened. Capsules that take the form of encapsulated cells can also be opened as above, facilitating analysis of the activation state, histology, and physiology, of the formerly encapsulated cells.

Emulsifiers

An emulsifier can stabilize initial emulsion, before heat-induced crosslinking and gelling. An emulsifier can also lower the droplet size at the same impeller speed. Polyvinyl alcohol (0.1-1.0%) is a suitable emulsion stabilizer, without implying any limitation.

Lower Critical Solution Temperature

Lower Critical Solution Temperature (LCST) can be considered equivalent to Tgel (gel point) as the polymer is insoluble (but is hydrated) above this point. Methods for measuring LCST are available (See, Tan et al (2009) Biomaterials. 30:6844-6853).

Polydispersibility index

A suitable Polydispersity Index is in the range of 1.05-1.15 range with 1.06 average, without implying any preference. A Polydispersibility Index of less than 1.5 can provide a more reproducible and defined product, potentially important in FDA filings. The minimal possible Polydispersibility Index is 1.0. Formulas for Polydispersiblity Index (PI) are as follows.

PI=(weight average molecular weight of polymers)/(number average molecular weight of polymers)

PI=ΣwiMi=(total weight)/(number of polymers)

In the above summation formula, wi is fraction by weight of each species, and Mi is molecular weight of that species.

Functionalization of Polymers

Functional groups can be added at polymer terminus, using epichlorohydrin, as described (see, e.g., para. 0067 of US 2012/0046435). Another way to introduce functionalization is polymerization with 1,6:2,3-dianhydro-4-O-allyl-b-D-mannopyranose. The introduced allyl side group functionality can be used for crosslinking directly, or converted to thiol, amine, etc. reactive groups.

In a preferred embodiment, encapsulated islets are separated, by way of a distance, from inner wall of the capsule. Islets can have a diameter of about 50 micrometers (μm) to 300 μm (Bosco et al (2010) Diabetes. 59:1202-1210). The present disclosure provides a distance of at least 5 μm, at least 10 μm, at least 15 μm, at least 20 μm, at least 25 μm, at least 30 μm, least 30 μm, at least 50 μm, at least 60 μm, least 70 μm, at least 80 μm, at least 100 μm, at least 125 μm, at least 150 μm, at least 200 μm, at least 250 μm, 300 μm, at least 400 μm, at least 400 μm, and the like.

Measurements of Average of Three Shortest Distances along X-axis, Y-axis, and Z-axis The distance between external surface of an islet, and the internal surface of the capsule, can measured in radial directions. Where the islet is not exactly centered inside the capsule, the above-defined distance can be the average of the three shortest distances found in the X-axis, Y-axis, and Z-axis (all three dimensions). What is also provided is a population of islets, where at least 20%, at least 30%, at least 40%, at least 50%, at least 60%, at least 70%, at least 80%, at least 90%, at least 95%, of the encapsulated islets, can be characterized as having a distance of at least 20 μm, at least 50 μm, at least 100 μm, at least 200 μm, and so on. Methods for using microscopy to assess dimensions, shapes, and sizes of cells, are available, for example from U.S. Pat. No. 8,213,081 of Lippert, and U.S. Pat. No. 8,228,499 of Lippert, which are incorporated herein by reference in their entirety.

In exclusionary embodiments, the present disclosure can exclude any preparation of encapsulated islets, or any population of encapsulated islets, where at least 10% of the encapsulated islets has a distance that is less than 5 μm, less than 10 μm, less than 20 μm, less than 30 μm, less than 50 μm, less than 100 μm, less than 150 μm, less than 200 μm, and so on.

The present disclosure provides implants that are one or more of subcutaneous (sc), sub-renal capsule, intrahepatic, intravenous, intra-arterial, intramuscular (im), implantation into the wall of the stomach, small intestines, or large intestines, implantation into bone marrow or spleen, implantation into any visceral tissue or organ, and the like.

Indications

Polymers of the present disclosure that exhibit reversible gel/liquid transitions are also useful encapsulation of mammalian cells such as islets, and are also useful as drug delivery device system components, for example to formulate injectable drugs preferred polymers. The present disclosure provides hydrogels that are capable of temperature-induced dissolution, where an injected or implanted hydrogel (containing a drug) can be heated by way of applying heat to the skin, where the applied heat provokes gel dissolution with the consequent controlled release of the drug.

Polymer compositions of the present disclosure that exhibit reversible gel/liquid transitions are useful as injectable for sub-dermal maxiofacial applications such as wrinkle fill, lip augmentation, reduction of folds, removal of scars and the like similar to the manner in which hyaluronic acid and collagen are used in cosmetics procedures.

Polymer compositions of the present invention that exhibit reversible gel/liquid transitions are useful to augment of the body tissue in surgical procedures such as organ restoration, breast volume enhancement, eye surgery, knee restoration, ulcer treatment and the like. As well as use in eye surgery, e.g. corneal transplantation, cataract surgery, glaucoma surgery and surgery to repair retinal detachment. Such polymers are also useful as physiologic lubricants and as non-inflammatory vitreous substitutes to prevent scrapping of the endothelial cells as well as injectable agents for the treatment of arthritis particularly osteoarthritis of the knee.

Polymer compositions of the present invention that exhibit reversible gel/liquid transitions are useful in the synthesis of biological scaffolds for wound healing applications. Such scaffolds typically utilize proteins such as fibronectin attached to the hyaluronan to facilitate cell migration into the wound treatment for ankle and shoulder osteoarthritis pain. The DM polymers of the present invention are useful as tissue engineering products such as scaffolding and the like. Certain polymers of the present invention that exhibit reversible gel/liquid transitions are useful in combination with sodium bicarbonate or other agents to treat acid reflux and diarrhea.

Exclusionary Embodiments

The present disclosure provides polymers, capsules, encapsulated cells, methods of manufacture, methods of medical use, and the like, that can exclude the following. What can be excluded is a polymer where the lower critical solution temperature (LCST) is greater than 37° C. (body temperature). What can be excluded is any polymer, any gel, any capsule, and the like, where relatively lower temperatures result in increase in viscosity, and where relatively higher temperatures result in decrease in viscosity (for example, what can be excluded is a particular polymer that increases in viscosity at 20° C. and decreases in viscosity at 37° C.). What can also be excluded are capsules that contain, by weight, over 1%, over 2%, over 5%, over 10%, over 20%, over 50%, cellulose, chitosan, amylose, alginate, agarose, polysaccharide, amino acid polymers, polymethylene-co-guanidine, polymer with triacrylate monomers, polymer with vinylpyrrolidone monomers, or polysiloxane, polyethylene glycol, and so on. What can be excluded is a polymer that is toxic to cells, or a polymer that is degraded in vivo to provide breakdown products that are toxic to cells. What can be excluded is any polymer that is capable of forming a capsule, or any capsule, where pore size is large enough to allow passage of a globular protein of molecular weight of 150 kD or greater, of 200 kD or greater, of 250 kD or greater, of 300 kD or greater, and the like. What can also be excluded is any capsule or other structure formed with a plurality of polymer molecules, that can be degraded in the mammalian body over the course of time, where greater than 1% degradation, greater than 2%, greater than 5%, greater than 10%, greater than 20%, greater than 50% degradation occurs as measured at a time point such as 1 month after implantation, at 4 months after implantation, at 12 months after implantation, and so on. In exclusionary embodiments, the present disclosure can exclude any method, reagent, or compositions prepared by the method, that involves ionic gelation, physical self-assembly, free radical-induced gelation, photopolymerization, chemical crosslinking, or any combination of the above. Also, what can be excluded is any capsule, or any polymer that forms a capsule, where the capsule is of non-uniform wall thickness. A capsule with non-uniform wall thickness can be a capsule where thickness measurements taken at 1,000 random positions over one particular capsule (or taken over 1,000 random positions from many capsules) have an average thickness, and where the average of the difference from the average thickness is greater than 5% from the average thickness, greater than 10%, greater than 15%, greater than 20%, greater than 50%, greater than 100%, greater than 200%, greater than 500% (5-fold), greater than 10-fold, and so on.

What can be excluded is any capsule, any capsule that encapsulates mammalian cells, or any polymer, that contains more than 5% alginate by weight (dry weight), more than 10%, more than 15%, more than 20%, more than 25%, more than 30%, more than 40%, more than 50%, more than 60%, more than 70%, and the like, of alginate by weight (dry weight).

What can also be excluded is any capsule, any capsule that encapsulates mammalian cells, or any polymer, that contains more than 5% polyethylene glycol (PEG) by weight (dry weight), more than 10%, more than 15%, more than 20%, more than 25%, more than 30%, more than 40%, more than 50%, more than 60%, more than 70%, and the like, of polyethylene glycol by weight (dry weight).

In other exclusionary embodiment, the present disclosure can exclude any other polymer by the indicated exclusionary parameters.

Capsules that do not contain mammalian cells are disclosed by the following exclusionary embodiments. The present disclosure includes A population of the polymeric capsule, wherein none of the capsules in the population comprise a mammalian cell, and wherein at least 50% the capsules (or at least 60%, at least 70%, at least 80%, at least 85%, at least 90%, at least 95%, or at least 98%) are capable of excluding a globular protein of a molecular weight of at least 50 kilodaltons, at least 100 kD, at least 150 kD, at least 200 kD, at least 250 kD, at least 300 kD, and so on.

EXAMPLES

Three separate lots of human islets were encapsulated using Transient Emulsion Encapsulation method, using polymer S-246. The three lots were numbered as follows: HP-12345-01; HP-13003-01; HP-13011-01.

Example 1

First Human Islet Preparation

FIG. 1 shows dithazone staining before encapsulation, and FIG. 2 shows dithazone staining after encapsulation. FIG. 3 and FIG. 4 reveal viability staining before and after encapsulation, respectfully. FIG. 5 and FIG. 6 show light microscopy of encapsulated with a bar showing lengths of 1000 μm (FIGS. 5) and 400 μm (FIG. 6). The polymer coating picks up a light red stain, while the islets that are viable stain green. The islets that are not viable stain a bright red. Encapsulated islets, prior to culture, show distinctive centralization of the islet mass within the central portion of the capsules with smaller capsules noted in the 100 μm range to the 300-400 μm range, for most of the encapsulated islets. For these smaller encapsulated islets the islet mass is centered within the capsule with a rather even thickness of the surrounding coating.

FIG. 7 shows Glucose Stimulated Insulin Release (GSIR). GSIR results show greater insulin release with encapsulated islets, and lower insulin release with naked islets. In other words, encapsulation resulted in a stimulation of values for Stimulation Index Value. The stimulating glucose concentrations going forward were 3 mM-12 mM-20 mM-20 mM plus IBMX 3 mM. IBMX is 3-isobutyl-1-methylxanthine. IBMX is a phosphodiesterase inhibitor that raises islet cAMP levels and causes insulin release at nonstimulatory glucose concentrations (Siegel et al (1980) J. Clin. Invest. 65:233-241).

Prodo islet media can be used in the procedure for encapsulating islets. As an alternative to Prodo islet media, what can be used is, for example, CMRL-1066 medium, CMRL-1415 medium, or CMRL-1969 medium (see, e.g., Healy and Parker (1966) J. Cell Biol. 30:531-538; Healy et al (1971) Appl. Microbiol. 21:1-5; Healy and Parker (1966) J. Cell Biol. 30:539-553).

Formulas that can be Used for Calculating Stimulation Index
Stimulation 1 is (12 mM Glucose Stimulated Insulin Release)/(3 mM Glucose Insulin Release).
Stimulation 2 is (20 mM Glucose Stimulated Insulin Release)/(3 mM Glucose Insulin Release).
Stimulation 3 is (20 mM+IBMX Glucose Stimulated Insulin Release)/(3 mM Glucose Insulin Release).

FIG. 7 shows GSIR insulin release at week 1, in terms of average insulin ng/ngDNA/hour. FIG. 8 shows GSIR Stimulation Index Value, at week 1.

Example 2

Second Human Islet Preparation

Results from the second human islet preparation encapsulated by Transient Emulsion Technique are quite similar to those from the first human islet preparation, in terms if islet viability results, and GSIR results. Regarding the second donor, islet responsiveness was somewhat slow at lower doses, but gave excellent results at higher doses. At all times in the assay, the results from the encapsulated islets were better than those from naked islets. The stimulating glucose concentrations going forward were 3 mM-15 mM-28 mM-28 mM plus IBMX 3 mM (FIGS. 9-16).

FIGS. 9 and 10 show dithazone staining for naked islets and for encapsulated islets, respectfully. FIG. 11 shows viability staining for naked islets and for encapsulated islets. FIGS. 12, 13, and 14, show light microscopy photographs of encapsulated islets, disclosing viability staining (1000 μm bar) (FIG. 12), photo with no bar (FIG. 13), and photo with 1000 μm bar (FIG. 14).

FIG. 15 shows GSIR results at week 1, where the results are in terms of average insulin ng/ngDNA/hour. FIG. 16 shows GSIR Stimulation Index results, at week 1.

Example 3

Third Human Islet Preparation

The experimental results acquired with use of the third human islet preparation were similar to those from the first and second preparations. The encapsulated islets were well-centered. The third islet preparation had smaller islets than the other two preparations. Photographs of the encapsulated islets reveal that the larger islets are well centered in the capsules. But, if there are no larger islets, then the small islets do not center as well, most likely due to the fact that their density is much lower than the larger islets and closer to that of the fluid. This would tend to reduce their locating in the center. Where desired, the present disclosure encompasses the optional step of removing small islets from the islet preparation prior to encapsulation. Regarding the GSIR results, there was a larger insulin output for the first 3 mM glucose period than the last 3 mM period, that can be attributed to the much smaller islets. The first and the last 3 mM glucose concentrations stimulated insulin values should be very close together. Keeping that the first value in the calculation of the results does reduce the Stimulation Indices values in this run. It is interesting that the first and last 3 mM glucose stimulated insulin values for the encapsulated islets are very similar, reducing this effect observed in the unencapsulated islets. The stimulating glucose concentrations going forward were 3 mM-15 mM-28 mM-28 mM plus IBMX 3 mM.

FIG. 25 shows the combination of all three islet preparations, with and without encapsulation. By plotting all three donors on one chart, it can be seen that the stimulated insulin release from the encapsulated islets is above the levels for the naked islets. The Stimulation Indices tend to reduce the donor to donor variations as seen in the Stimulation Index Summary. By plotting all three donors on one chart, it can be seen that there are some donor to donor variations that affect GSIR results as noted above with higher IBMX values for donor 13001 and lower responses in donor 13011. There is a difference of insulin release as well as in Stimulation Indices with the last donor, 13011 with small islets, between unencapsulated islets and those that were encapsulated with the higher responses after encapsulation. The present disclosure establishes that significant advantages result from using the transient emulsion technique, as compared to use of the alginate encapsulation technique, for encapsulating islets and cells.

Introduction to Experimental Results

Macro- and micro-capsules, conformal coatings, and minimal volume capsules (MVC) have been developed for islet encapsulation but result in limitations and disadvantages for clinical application. The present disclosure provides a novel, improved Minimal Volume Capsule (MVC), for use in encapsulating clusters of cells, such as islets of Langerhans, for encapsulating a plurality of non-clustered cells, or for encapsulating individual cells. The present disclosure provides MVCs from 100 to 300 micrometers (μm) diameter with centralization of the encapsulated islet, uniform wall thickness, and smooth outer wall. Three human islet preparations had islets encapsulated and tested by glucose stimulated insulin release (GSIR). The average GSIR values for Control, unencapsulated human islets were for 3 mM Glucose (G)=0.063 Insulin (Ins) {ng/ngDNA/Hr}, for 15 mM G=0.144 Ins, for 28 mM G=0.216 Ins, for 28 mM G+10 mM IBMX=0.749 Ins, and 3 mM G=0.082 Ins. For MVCs, the average GSIR values were for 3 mM G=0.041 Ins, for 15 mM G=0.166 Ins, for 28 mM G=0.343 Ins, for 28 mM G+IBMX=0.966 Ins, and 3 mM G=0.058 Ins. The average Stimulation Indices (StimInd) for insulin release of these were Control StimInd #1 (G15 mM/3 mM)=2.74, for StimInd #2 (G28/G3)=4.73, and for StimInd #3 (G28+ IBMX/G3)=13.12. The Stimind for the encapsulated human islets were StimInd #1=4.29, StimInd #2=9.79, and StimInd #3=22.96. DTZ and FDA/EB viability staining of control and encapsulated islets confirmed these findings. Previous mouse implants of empty capsules show excellent rodent biocompatibility. This novel polymer can be additionally cross-linked to change permeability without adding new layers. The new polymer MVC's provides clinically relevant small size, centralization of human islets, uniform wall thickness, and excellent in vitro encapsulated human islet function in response to glucose. FDA/EB staining refers to staining with fluorescein diacetate (FDA) and ethidium bromide (EB) (see, e.g., Gray and Morris (1987) Stain Technol. 62:373-381).

Introduction to Polymers of the Present Disclosure

Preferred polymers for the present disclosure include those of US 2012/00464354 of Gorkovenko and US 2012/0087891 of Gorkovenko, each of which is incorporated herein in its entirety. FIG. 33 identifies, without implying any limitation, various R groups that can be covalently bound to poly(2-3)-D-pyranoses.

As indicated in FIG. 33, these R groups can include a methyl group (abbreviated as "O"), butyl ("Bu"), pentyl ("P"), hexane group ("H"), octyl group ("Oc"), decane group ("Dc"), allyl group ("A"), isopentane group ("Ib"), and so on.

Table 4 discloses relative hydrophilicity and hydrophobicity of TRGel homopolymers of the present disclosure, when the homopolymer contains the indicated R group. The R groups are indicated by the abbreviations, T, D, M, O, A, Bu, P, H, Oc, Dc, Ib, Ia, B, Ip, and Np. Table 5 provides some exemplary non-limiting cell encapsulating polymers, where four examples are given.

TABLE 4

TRGel homopolymers containing the indicated R group

| more hydrophilic | | | | | | | | | more hydrophobic |
|---|---|---|---|---|---|---|---|---|---|
| 1 | 2 | 3 | 4 | 5 | 6 | 7 | 8 | 9 | 10 |
| T | D | M | O | A | Bu | P | H | Oc | Dc |
|   |   |   |   |   | Ib | Ia | B |   |   |
|   |   |   |   |   | Ip | Np |   |   |   |

TABLE 5

Exemplary polymers suitable for encapsulating cells

| Polymer | Polymer composition | | | Tgel | Tgel |
| | O mol % | M mol % | D mol % | 15% in PBS degrees C. | 10% in water degrees C. |
|---|---|---|---|---|---|
| 1 | 55 | 25 | 20 | 25 | 30 |
| 2 | 50 | 25 | 25 | 28 | 35 |
| 3 | 57.5 | 5 | 37.5 | 32 | 38 |
| 4 | 45 | 27.5 | 27.5 | 32 | 38 |

Background Information on Emulsions

The present disclosure provides water-in-oil emulsion. The water is the "dispersing phase" and the oil is the "continuous phase." "Continuous phase" refers to bulk phase. The oil that is used is preferably mineral oil or silicone oil. Olive oil can also be used, but the result with olive oil is that beads of olive oil coat the outside of the capsule, as well as the cells that are located within the capsule. When viewed with a microscope, the beads present themselves as a rough surface. With mineral, the appearance under the microscope takes the form of a smooth surface.

Emulsion Technique with Spinning Droplet

The following describes an embodiment of the "emulsion technique with spinning droplet." The emulsion is a "water in oil" emulsion, made by spinning a propeller in a spherical glass container. First, create droplets. Use 1,500 rpm with propeller. Silicone oil or mineral oil is preferred.

Use 180 g as maximal g force. Using above 180 g is avoided, in order to prevent damage to islets. The propeller is 5 cm in diameter, and there is a 10 mm space from the tip of the propeller to the glass wall of the spherical glass container.

After making the emulsion, add a lower layer of cells, for example, a lower layer of islets. Then, spin with a propeller for one minute more. Then stop the propeller. The size of the encapsulated islets is 100-300 micrometers (μm).

A water bath at 60 degrees C. is used to initiate heating, and to continue with heating. Immerse the spherical glass container in the 60 degree C. water bath. Inside, the initial temperature of the emulsion is relatively low, that is, 20 degrees C. Allow the temperature to rise inside, and spin the propeller until the temperature inside is about 34 degrees C. (do not allow temperature inside to rise about 37 degrees C., or else islets will be damaged). The temperature will rise to about 34 degrees in about 20 seconds. Keep the propeller going, but remove from water bath, and spin the propeller for ten more seconds to draw off heat from the glass wall of the spherical glass container, that is, in order to prevent the emulsion inside from being exposed to glass that is at 60 degrees C. The result is that the islets are encapsulated, when the entire emulsion is at about 34 degrees. The next step is to purify the encapsulated islets. This can be done by allowing the encapsulated islets settle. The density of the polymer is 1.20 to 1.25. The density of the oil phase is 0.8 or lower. The density of the capsules is about 1.1. Thus, after the capsules sink to the bottom (due to their greater density than the oil phase), decant the oil to get rid of the oil.

The present disclosure encompasses various methods for collecting encapsulated islets, encapsulated individual cells, encapsulated clumps of cells, encapsulated tissues, and the like. These can be collected, enriched, separated, or purified, by way of settling in gravity, by centrifugation, by filtering, by antibody-mediated capture where the antibody recognizes an epitope on the capsule, by way of a substrate-based ligand that reacts non-covalently, covalently, or in a reversible covalent manner, with a functional group on the capsule, and the like, without implying any limitation.

Islet Encapsulation Techniques that do not Involve Spinning Drops

Spinning drop technique, which involves islet droplets formed using an emulsion, is distinguished from the "drop technique" of encapsulation where islet droplet is not spinning. Where islet droplet is not spinning, islets accumulate to side of droplet, and fail to be centered at the middle of the droplet. In exclusionary embodiments, the present disclosure can exclude any technique for cell encapsulation, or islet encapsulation, that does not involve spinning drops.

Embodiments of Emulsion Technique with Spinning Droplet

As mentioned above, initial temperature of emulsion is relatively low. Initial temperature can be, without implying any limitation, 2-4° C., 4-6° C., 6-8° C., 8-10° C., 10-12° C., 12-14° C., 14-16° C., 16-18° C., 18-20° C., 20-22° C., 22-24° C., 24-26° C., 26-28° C., and the like. Also, initial temperature can be, for example, 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 26° C., 27° C., 28° C., and the like. The present disclosure also provides step-wise increases in temperature, for example, where for a first interval, temperature is held at 18° C. during spinning of the propeller, and for a second interval, temperature is held at 22° C. during spinning of the propeller, and then the temperature is finally allowed to rise to 34° C. The number of steps can be one step, two steps, three steps, four steps, five steps, and so on, where each step takes the form of holding at a specific temperature. Also, the present disclosure provides a continuous increase in temperature, where there is not any distinguished holding time at a given temperature. Transition time from one temperature to a pre-determined higher temperature (or to a pre-determined higher temperature range), can be 5 seconds, 10 sec, 15 sec, 20 sec, 25 sec, 30 sec, 40 sec, 45 sec, 50 sec, 60 sec, 70 sec, 80 sec, 90 sec, 100 sec, 110 sec, 120 sec (2 min), 3 min, 4 min, 5 min, 10 min, or any combination of the above. Dwelling time at any given temperature, or at any given temperature range such as 20-22° C., can be 10 sec, 20 sec, 30 sec, 40 sec, 50 sec, 60 sec, 70 sec, 80 sec, 90 sec, 100 sec, 110 sec, 120 sec (2 min), 3 min, 4 min, 5 min, 10 min, or any combination of the above.

The present disclosure, in some embodiments, includes mixing the islets with the emulsion at a low temperature, such as at 2-4° C., 3-5° C., 4-6° C., 5-7° C., 6-8° C., 7-9° C., 8-10° C., and the like, and then bringing up to 20° C., followed by bringing up to 34° C.

Rotation Embodiments

Propeller can be rotated, for example, at 1,500 rpm for 5 minutes, 10 min, 15 min, 20 min, 25 min, 30 min, and the like. Also propeller can be rotated at 1,000 rpm for 5 minutes, 10 min, 15 min, 20 min, 25 min, 30 min, and the like. Also propeller can be rotated at 2,000 rpm for 5 minutes, 10 min, 15 min, 20 min, 25 min, 30 min, and the like. Rotation can be at, for example, 500 rpm, 600 rpm, 700 rpm, 800 rpm, 900 rpm, 1000 rpm, 1100 rpm, 1200 rpm, 1300 rpm, 1400 rpm, 1500 rpm, 1600 rpm, 1700 rpm, 1800 rpm, 1900 rpm, 2000 rpm, 2100 rpm, 2200 rpm, 2300 rpm, 2400 rpm, 2500 rpm, or any combination defining a range, such as 1200-1300 rpm, and so on. Propeller can have diameter of 0.1 cm, 0.2 cm, 0.5 cm, 1 cm, 1.5 cm, 2.0 cm, 2.5 cm, 3.0 cm, 3.5 cm, 4.0 cm, 5.0 cm, 5.5 cm, 6.0 cm, 7.0 cm, 8.0 cm, 8.5 cm, 9.0 cm, 9.5 cm, 10 cm, 15 cm, 20 cm, or any additive combination thereof, such as 6.5 cm, or 9.2 cm. Rotation can be expressed in terms of gravity minutes.

The following examples are of encapsulation solutions and procedures for emulsification and encapsulation.

Example 4

Encapsulation Solution

TRGel polymer t-OMD-91 was dissolved in distilled water at 5% (weight %), filtered through 0.2 μm Surfactant Free Cellulose Filters (SFCA) filter, frozen at minus 20° C., lyophilized and reconstituted in sterile PBS as 15% w/v solution. Measured gel set temp was 26° C. This encapsulating solution can be processed as liquid up to 25° C. Recommended handling temp <=24° C. S-246 beads formed at 37° C. using procedure below are stable at room temperature after encapsulation run for at least 30 min. Beads cured at 37° C. for 24 hrs are stable at room temperature for at least 3-4 weeks, at 4° C. for 24 hrs. S-246 beads will dissolve in about 48-72 hrs exposure to 4° C.

This procedure used human pancreatic islets. Use of TRGel polymer encapsulating solution S-246, Ratio: 200 uL per 10,000 IEQ islets, silicon oil (cyclomethicone), 30 mL, 50 mL round shaped 3 neck flask, oval impeller, IKA RW20 digital mixer with PP stirring shaft guide. Inside (oil) temperature was controlled by immersed thermocouple. Islets were pelleted at 180 g for 2 min, from Prodo media. Media was removed by aspiration and polymer solution was added and islet suspension formed. Islet suspension was transferred to the encapsulating flask with oil (best if all islets are at the flask bottom). Starting oil temp was about 24° C. The emulsion was formed by stirring for 60 sec at 1460 rpm, then outside water bath (56° C.) was introduced for 15 sec (inside temp reached 34° C.) and stirred for 10 sec more (inside temp was 38.5° C. max). Bead suspension was allowed to settle for 2 min, oil was decanted form an encapsulating flask. 20 ml of 37° C. Prodo media was added and the flask content was manually agitated using pipette for 1 min. Beads were allowed to settle on the bottom for 1 min and collected from the bottom using pipette. This procedure was repeated to collect more beads from glass walls. The procedure yielded about 300 um size beads with empty/loaded islets content of about 50% mostly with centered islets position.

FIG. 35 shows the size distribution of the capsules, for an example where the procedure used an impeller speed of 1520 rpm.

One or more of the following techniques can be used for combining cells with oil, without implying any limitation:

Pellet can be resuspended and dispersed in oil with stifling to form an emulsion. In this embodiment, there is not any separate aqueous solution.

Alternatively, pellet can be mixed with oil plus an aqueous solution, with stirring to form an emulsion. The aqueous solution is in addition to any aqueous solution that is associated with the pellet.

The order of addition can be simultaneous combination of pellet, oil, and aqueous solution. Or the order can be initial combination of pellet and aqueous solution, with or without dispersal of cells, followed by addition of oil. Or the order can be initial combination of pellet with oil (with or without dispersal of cells), followed by addition of aqueous solution. Emulsion can be generated by stifling at the moment when oil and aqueous solution are initially combined (with pellet added subsequently). Alternatively, emulsion can be generated by stifling at the moment when oil and pellet are initially combined (with aqueous solution added subsequently). As mentioned above, procedure can be one where the emulsion is initially generated when pellet, aqueous solution, and oil, are simultaneously combined together.

Example 5

The following provides another example of the procedure for emulsification and encapsulation. Use TRGel polymer S-246, 180 uL per 8,000 IEQ islets, silicon oil (cyclomethicone), 30 mL, 50 mL pear shaped 1 neck flask, oval impeller, IKA mixer.

Keep room temp <=24° C. Fill flask with oil. Mix islets pellet with polymer solution, position polymer suspension to the flask bottom (under oil), centrifuge 1 min at 1500 rpm at room temperature, then use 55° C. outside water bath for 20 sec, remove water bath, centrifuge for 10 sec more, stop. Let beads settle, decant the oil, add 37° C. Prodo media (20 mL) suspend, settle, wash 3 times, transfer islets to the flat flask in Prodo Media for 37° C. incubation. This procedure should yield about 50% beads filled, size 100-400 μm beads, average about 300 μm, mostly with centered islets position.

Example 6

The following provides an additional example of the procedure for emulsification and encapsulation. Use TRGel polymer S-246, 50 μL per 2,500 IEQ islets, silicon oil (cyclomethicone), 30 mL in 50 mL pear shaped 1 neck flask, oval impeller IKA RW20 digital mixer with PP stirring shaft guide. Keep at room temperature. Fill flask with oil. Mix islets pellet with polymer solution, position polymer suspension to the flask bottom (under oil), centrifuge 1 min at 1500 rpm at room temperature, then used 53° C. outside water bath for 20 sec, remove water bath, centrifuge for 10 sec more, stop. No control of inside oil temp. Let beads settle, decant the oil, add 37° C. Prodo media (20 mL) suspend, settle, wash 3 times, transfer islets to the flat flask in Prodo Media for 37° C. incubation. This procedure should yield about 50% beads filled, size 100-400 μm beads, average about 150-200 um, mostly with centered islets position.

FIG. 27 shows a photograph of the encapsulated islets produced by the above example.

Encapsulation polymer t-OMD-130 was used for encapsulation solution S-146. The chemical known as "t-OMD-130" is: Poly (2-3)-1,6-anhydro-4-O-(methyl-co-(2-methoxyethyl)-co-(2-(2-methoxyethoxyethyl))-b-D-glucopyranose.

Example 7

Mesenchymal Stem Cells

This describes encapsulation solution S-146 and TRGel polymer t-OMD-130. TRGel polymer t-OMD-130, 15% w in PBS. Measured gel set temp was 31.5° C. This encapsulating solution can be processed as liquid up to 30° C. Recommended liquid handling temp <=30° C. S-146 beads formed at 37° C. using procedure below are stable at room temperature after encapsulation run for at least 10 min. Beads cured at 37° C. for 24 hrs are stable at room temperature for at least two weeks, at 4° C. for at least eight hours. S-146 beads will dissolve in 24 hours with exposure to 4° C.

This describes a procedure used for emulsification and encapsulation of human mesenchymal stem cells (hMSC). First run of new encapsulation procedure to encapsulate human mesenchymal stem cells (hMSC).

Human mesenchymal stem cells (hMSC) (Prodo Labs, Irvine, Calif.) about 1 M cells, P8 batch were trypsinized for 4 min, diluted, pelleted, resuspended in media, pelleted at 2000 rpm for 4 min, resuspended in 80 mg of S-146 encapsulating solution. Encapsulation. Silicone oil, (cyclomethicone), 27 g in 50 mL pear shaped 1 neck flask, oval impeller IKA RW20 digital mixer with PP stirring shaft guide. Fill flask with oil, position hMSC polymer suspension to the flask bottom (under oil), centrifuge 1 min at 1500 rpm at room temperature (actual conditions about 1550 rpm), then used 56° C. outside water bath for 20 sec, remove water bath, centrifuge for 10 sec more, stop. No control of inside oil temp. Let beads settle, decant the oil, added 37° C. Prodo media (20 mL) suspend, settle, washed one more time, transferred islets to the flat flask in Prodo Media for 37° C. incubation. Non sterile parts were used during encapsulation. Capsules sample dissolved after about 15 min handling at room temperature. All beads were filled with round hMSC, no empty capsules. Average size 150-200 μm. This procedure should yield ~50% beads filled, size 100-400 um beads, average about 150-200 um, mostly with centered cell clusters position. 24 hrs incubation at 37° C. in Prodo hMSC media: same cell morphology and bead size.

FIG. 30, FIG. 31, and FIG. 32, show results from the above procedure, for encapsulating hMSC.

Success in Reducing Number of Empty Capsules

The Transient Emulsion Encapsulation method of the present disclosure has resulted in in a low percentage of empty capsules. Encapsulated islets can be detected by way of staining with dithazone. Dithazone staining can use, for example, Pancreatic Cell DTZ Detection Assay, cat. No. SCR047, Millipore, Billerica, Mass.). In embodiments, less than 20% of the capsules are empty, less than 15%, less than 10%, less than 5%, less than 2%, less than 1%, less than 0.5%, less than 0.2%, less than 0.1%, less than 0.05%, less than 0.02%, less than 0.01%, less than 0.005%, less than 0.002%, less than 0.001% of the capsules are empty, and so on. Without implying any limitation, capsule occupancy can be determined with dithazone staining.

Removal of Cells from Capsules

Removal of islets from alginate capsules is very difficult to accomplish. However, use of polymer S-246 with the emulsion method of the present disclosure enables easy removal of cells from the capsules. Once removed, islets can be analyzed for growth and cell division, for ability to express insulin or other proteins, for metabolism, for oxidation products or for genetic damage, and so on.

Connection between t-OMD-91 and S-246 t-OMD-91 is an encapsulating polymer. S-246 is encapsulating solution based on t-OMD-91 polymer. In other words, t-OMD-91 is encapsulation polymer for S-246 solution. Monomers, solvents and initiators were prepared according to US 2012/0046435, US 2012/0087891, and U.S. Pat. No. 7,994,092. The chemical known as "t-OMD-91" is: Poly (2-3)-1,6-anhydro-4-O-(methyl-co-(2-methoxyethyl)-co-(2-(2-methoxyethoxyethyl))-beta-D-glucopyranose.

Encapsulating Polymer for S-246 Solution

Encapsulation polymer for S-246 solution. Monomers, solvents and initiators were prepared according to US 2012/0087891, US 2012/0046435, and U.S. Pat. No. 7,994,092, where are each incorporated by reference in their entirety.

Poly(2-3)-1,6-anhydro-4-O-(methyl-co-(2-methoxyethyl)-co-(2-(2-methoxyethoxyethyl))-beta-D-glucopyranose is described below.

0.483 g of 1,6:2,3-dianhydro-4-O-methyl-beta-D-mannopyranose, 0.283 g of 1,6:2,3-dianhydro-4-O-(2-methoxyethyl) -beta-D-mannopyranose, 0.276 g of 1,6:2,3-dianhydro-4-O-(2-(2-methoxyethoxyethyl)-beta-D-mannopyranose, 1 g of tetrahydrofuran (THF), 81 mg of 181 mM solution of potassium 3,3-Diethoxy-1-propanolate in THF were loaded into 10 mL reaction vessel, mixed at room temperature to obtain a clear solution, sealed and incubated at 55° C. for 12 hrs. Polymer was recovered by mixing the reaction mixture with 8 mL of DI water, precipitating polymer by heating the content to 60° C. and vacuum drying the polymer for 24 hrs. Yield=1.008 g, GPC analysis: Mw=44061, Mn=40072

0.470 g of 1,6:2,3-dianhydro-4-O-methyl-beta-D-mannopyranose, 0.212 g of 1,6:2,3-dianhydro-4-O-(2-methoxyethyl) -beta-D-mannopyranose, 0.397 g of 1,6:2,3-dianhydro-4-O-(2-(2-methoxyethoxyethyl)-beta-D-mannopyranose, 1 g of THF, 99 mg of 182 mM solution of potassium 3,3-Diethoxy-1-propanolate in THF were loaded into 10 mL reaction vessel, mixed at room temperature to obtain a clear solution, sealed and incubated at 55° C. for 12 hrs. Polymer was recovered by mixing the reaction mixture with 8 mL of DI water, precipitating polymer by heating the content to 70° C. and vacuum drying the polymer for 24 hrs. Yield=1.078 g (100%), encapsulation solution S-146 is a 15.0% solution of t-OMD-130 in PBS.

The polymer structure is shown below:

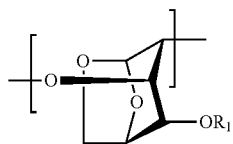

R1 in the ter-polymer example above is: —$CH_3$, —$CH_2CH_2$—$OCH_3$, and —$(CH_2CH_2O)_2CH_3$. In this example the side groups R1 are randomly distributed as all three monomers were mixed prior to polymerization. If these three monomers are added in steps they will form a triblock ter-polymer with different properties, but same chemical composition. Polymers with best properties relevant to specific encapsulation application are selected. Copolymerization with a monomer 1,6:2,3-dianhydro-4-O-allyl-beta-D-mannopyranose is used to introduce multiple functional side groups to enable crosslinking and functionalization. Termination of the polymer with agents such as succinic anhydride or epichlorohydrin is used to introduce a single functional group.

Composition and Tgel of Selected Polymers Used for Encapsulation

The composition and Tgel of selected polymers used in emulsification encapsulation is shown in the following tables (Table 1, Table 2).

TABLE 2

| monomer ID | | | Tgel | Tgel |
| O mol % | M mol % | D mol % | 15% in PBS ° C. | 10% in $H_2O$ ° C. |
| --- | --- | --- | --- | --- |
| 55 | 25 | 20 | 25 | 30 |
| 50 | 25 | 25 | 28 | 35 |
| 57.5 | 5 | 37.5 | 32 | 38 |
| 45 | 27.5 | 27.5 | 32 | 38 |

Properties of Homopolymers of Monomers Used in Gel Forming Polymers Synthesis

The following table discloses properties of homopolymers of monomers used in gel forming polymers synthesis. Side group, R1 is —$(CH_2CH_2)$n-$OCH_3$

TABLE 3

| Polymer ID | Side Group, n = | Tg | LCST, ° C. |
| --- | --- | --- | --- |
| t-O | 0 | 163.6 | n/a |
| t-M | 1 | 89.9 | 30 |
| t-D | 2 | 17.5 | 54 |
| t-T | 3 | −27 | 74 |

Polymers and Crosslinkers

A 1,6:2,3-dianhydrohexopyranose monomer useful for the synthesis of polymers of the present invention is shown in general structural formula (I) wherein R represents any moiety that does not interfere with anionic living polymerization, i.e., R should be a moiety that is weakly reactive or unreactive toward anions and other strong nucleophiles. In general, R is chosen to be a moiety that is neither nucleophilic nor electrophilic. In certain embodiments of the present invention R=straight-chain or branched alkyl, straight-chain or branched alkenyl, aryl, alkyl substituted aryl, aryl substituted alkyl, oxyalkyl, oxyethyl, poly(oxyalkylene), and poly(oxyethyene). In certain preferred embodiments R=straight-chain or branched alkyl with chain lengths from 1 to 18 carbon atoms and straight-chain or branched alkenyl with chain lengths from 1 to 18 carbon atoms. In certain other preferred embodiments R=straight-chain or branched alkyl with chain lengths from 1 to 12 carbon atoms and straight-chain or branched alkenyl with chain lengths from 1 to 12 carbon atoms. Particularly useful monomers for the synthesis of polymers of the present invention are 1,6:2,3-dianhydrohexopyranose monomers of structural formula (I) wherein R=allyl or benzyl.

Monomer units of the C2-C3 linked carbohydrate polyethers produced directly by the anionic, ring-opening, living polymerization of a monomer of formula (I) are represented by the general structural formula (II), wherein n=the average number of monomer units in a polymer chain.

The overall synthesis of a poly(2-3)-1,6-anhydro-4-O-beta-D-glucopyranose of formula (II) by the anionic, ring-opening polymerization of a 1,6:2,3-dianhydrohexopyranose of formula (I) is illustrated in Reaction Scheme A (see, US 2012/0087891). In this reaction sequence, the anionic initiator $A^-$ attacks the 1,6:2,3-dianhydrohexopyranose (I) at C-2 opening the 2-3 epoxy ring to afford the alkoxyl anion of formula (III) which subsequently the attacks a second molecule of (I) in a like manner to open the 2-3 epoxy ring forming an ether linkage and a new alkoxyl anion of formula (IV) to begin the living polymerizing chain. This sequence of steps continues until all monomer is consumed and a high polymer is produced. It is important to note that such a living polymerization can be stopped at any time by starving the reaction mixture of monomer at which time the growing polymer chain has a 'living end' and that the polymerization resumes when new monomer is introduced. The new monomer may be the same as the initial monomer or may be any other suitable monomer. Furthermore, two or more suitable monomers may be present in the initial reaction mixture, wherein the structure of the resulting copolymer is controlled by the concentrations and relative reactivity of the monomers. Since such a living polymerization adds monomers to a growing chain in serial fashion, molecular weight and copolymer composition are precisely controlled. Also, initiation of such living polymerizations can occur heterogeneously, i.e. from suitably reactive surfaces or in networks with suitable reactive sites such as anions.

In certain embodiments the carbohydrate polyethers of the present invention are designed to be water-soluble, while in certain other embodiments the polymers are designed to be water-insoluble. Additionally, in certain other embodiments the carbohydrate polyethers of the present invention are designed to produce aqueous emulsions, dispersions or suspensions. In essence the relative hydrophilicity/hydrophobicity of the carbohydrate polyethers of the present invention is controlled via selection of the functionality at one or more of the C-1, C-4 and C-6 positions on the glucopyranose rings and the number of rings so functionalized, i.e. the concentration of the functionality. By such selection techniques compositions can be prepared to provide aqueous solutions, aqueous emulsions or aqueous suspensions.

Non-limiting examples of embodiments wherein the carbohydrate polyethers of the present invention are water-soluble are presented by structural formula (IX), where p is an integer from 1 to 10, preferably from 1 to 4.

In general, functional groups may be introduced at the chain-ends of the carbohydrate polyethers of the present invention by the use of specific initiation or termination agents, while functionality along the polymer chain may be introduced or modified by post-polymerization reactions. This ability to introduce selective functionality into the polymers allows for the preparation of carbohydrate polyethers useful in the preparation of protein, peptide and drug conjugates. Polymers with non-reactive moieties such as alkyl at one terminus of the polymer chain are particularly useful for the homogeneous preparation of conjugates in the absence of cross-linking reactions. In certain embodiments, polymers of the present invention can be prepared with distinct reactive functional groups at the chain ends, wherein such heterobifunctional polymers are useful for applications such as targeted drug delivery and biosensors.

Examples of functional initiators for the anionic ring-opening polymerizations herein described included, but are not limited to, potassium 3,3-diethoxypropanolate, potassium 2-buthoxy ethanolate, dipotassium 3-thiolate-1-propionate and potassium allyl alkoxide. Allyl alkoxide is a particularly useful initiator since the resulting allyl ether end-group is easily converted a variety of other functionalities.

Examples of functional termination agents for the anionic ring-opening polymerizations herein described include, but are not limited to, alkyl halides, acylhalides, acid anhydrides, aldehydes, ethylene sulfide, ethylene oxide, 1,3-dibromoethane and 3-bromomethylpropyonate.

The 1,6:2,3-dianhydrohexopyranoses (Cerny epoxides) suitable as monomers for production of polymers of the present invention were prepared according to known methods starting from 1,6-anhydro-beta-D-glucopyranose of general formula (X) also commonly known as levoglucosan. In a typical procedure, the levoglucosan hydroxyl moieties at C-2 and C-4 were converted to p-toluenesulfonate esters by treatment with p-toluenesulfonyl chloride in pyridine TsCl/Py). Subsequent treatment of the reaction mixture with a strong base, such as sodium methoxide in methanol (MeONa/MeOH), effected the regioselective formation of the 3,4-epoxide resulting in formation of 1,6:3,4-dianhydro-2-O-p-toluenesulfonyl-beta-D-galactopyranose (XII) (also referred to as TDG) without recovery of the di-p-toluenesulfonate intermediate (XI).

The TDG thus produced was conveniently purified via conventional crystallization processes. The overall synthetic scheme is illustrated in Reaction Scheme G (see, US 2012/0087891).

In a subsequent reaction a dianhydromannopyranose (XIV), also referred to herein as a DM monomer, was produced via the acid-catalyzed alcoholysis of 1,6:3,4-dianhydro-2-O-p-toluenesulfonyl-beta-D-galactopyranose (XII) via treatment with an alcohol (ROH) in the presence of a suitable acid catalyst; wherein the 3,4-epoxide moiety was selectively cleaved to introduce the alcohol-derived R moiety at C-4 as depicted by formula (XIII) The subsequent treatment of the reaction mixture with a suitable base, such as sodium methoxide in methanol (MeONa/MeOH), effected the formation of a 2,3-epoxy moiety with concurrent with loss of the tosylate at C-2 to afford a dianhydromannopyranose (XIV). The overall process is illustrated below in Reaction Scheme H (see, US 2012/0087891).

In certain preferred embodiments, C2-C3 linked carbohydrate polyethers compositions and derivatives thereof the present invention are covalently coupled or crosslinked to from a self-supporting macroreticular network. The required covalent coupling or crosslinking can be effected by any known method. For example, free-radical crosslinking can be effected by suitable chemical processes, suitable irradiation processes or combinations thereof. Suitable chemical free-radical initiators include azobisisobutyronitrile (AIBN), benzoyl peroxide and the like. Suitable high-energy irradiation sources include electron beam, ultra-violet (UV) and gamma irradiation. Additionally, crosslinking promoters such as bifunctional, trifunctional or tetrafunctional acrylates or methacrylate monomers and oligomers may be added to increase crosslinking efficiency and crosslink density. In other embodiments, self-supporting macroreticular networks are be produced by the covalent coupling or crosslinking blends of carbohydrate polyethers of the present invention with suitable active oligomers or polymers.

The water soluble RTG polymers of poly(2-3)-1,6-anhydro-beta-D-glucopyranose (II) are often referred in text as DM polymers. Applications of reverse thermal gelation (RTG) polymers (DM polymers) of present invention include compositions for the treatment of constipation, encapsulation of sensitive mammalian cells, specifically for cell immobilization or encapsulation. Example of useful polymers for such applications include pMDM/DGDM copolymers, MW .about.33 k (30 mol % DGDM) wherein a solution (100 mg/L $H_2O$) remained a free flowing liquid at room temperature for at least 1 hr, whereupon heating the solution to .about 30-40° C. resulted in a non-flowing gel that remained non-flowing and transparent for at least 4 hrs at 26° C. After 8 hrs, at 19° C. gel reverted to a viscous liquid, and wherein heating the solution to about 60° C. effected precipitation of the polymer.

Certain preferred RTG polymers of the present invention are random copolymers, terpolymers and the like or block polymers of MDM wherein p=0. The MDM homopolymers are not soluble in water and this component is used to modify LCST and Tgel temperature of MEDM, DGDM and 3GDM polymers resulting in a family of thermosensitive polymers with gel transition temperature of 17° C. to 57° C.

Certain other preferred RTG polymers of the present invention block copolymers of MDM or alkyl-DM with MEDM, DGDM and 3GDM having hydrophobic ("A") block segments and hydrophilic ("B") block segments. Such block copolymers are triblock copolymers (e.g., ABA or BAB) that exhibit reverse thermal gelation properties and are biodegradable as well as biocompatible. Importantly, such triblock copolymers of the present invention provide instant gelation and possess the necessary rate of degradation to be commercially useful. Certain other preferred RTG polymers comprising biodegradable hydrophobic A block segments include p-MDM, p-ethyl-DM, p-propyl-DM and higher analogs.

The preferred range of molecular weights for certain preferred polymers useful in the present invention can be readily determined by a person skilled in the art based upon such factors as the desired polymer degradation rate, viscosity, polymer concentration in the solution. Typically, the preferred range of molecular weight will be 1000 to 150,000 Daltons, although there is no actual limitation.

The process used to mix the TRG polymers with a biologically active agent and/or other materials involves dissolving the polymers in an aqueous solution, followed by addition of the biologically active agent (in solution, suspension or powder), followed by thorough mixing to assure a homogeneous mixing of the biologically active agent throughout the polymer. Alternatively, the process can involve the dissolving of the TRG polymer in a biologically active agent-containing solution. In either case, the process is conducted at a temperature lower than the gelation temperature of the copolymer and the material is implanted into the body as a solution, which then gels or solidifies into a depot in the body. The biologically active agent will generally have a concentration in the range of 0 to 200 mg/mL.

Useful buffers in the preparation of the biologically active agent-containing hydrogels of the present invention are buffers which are all well known by those buffers known in the art and include, but are not limited to, sodium acetate, Tris, sodium phosphate, MOPS, PIPES, MES and potassium phosphate, in the range of 25 mM to 500 mM and in the pH range of 4.0 to 8.5.

The DM monomers as prepared by the methods exemplified in Examples 1-5 of US 2012/0087891 were converted to polymers by the anionic polymerization reaction as illustrated in Reaction Scheme A (see, US 2012/0087891) and the physical properties of homopolymers of differing monomers are presented in Table 1 of US 2012/0087891, which is incorporated herein by reference. With reference to Table 1 (see, US 2012/0087891) it should be noted that all of the resulting polymers have very low poly dispersity (Mw/Mn). The polymers wherein R=2-methoxyethyl and R=ethoxy-2-methoxyethyl are water-soluble.

Synthesis of TRG Polymers

Synthesis of random copolymer of MDM and DGDM (60/70 mol %) (pM/DGDM-8, with Tgel=30° C. is used here as an example. Reaction mixture containing MDM, 0.422 g; DGDM 0.310 g, THF, 0.7 g and 0.164 g of 57 mM solution of potassium 2-butoxyethoxylate in THF was crimped in a vial and incubated at 60° C. for 12 hrs. All polymerization experiments are performed in an argon-filled glove box. The polymerization mix was diluted with 2 mL of THF and polymer precipitated into 50 mL of ether, centrifuged and dried in vacuum. Polymer recovery was 0.730 g (99.7%). No residual monomer was found by GPC in the polymerization mix. Mn=32,613, Mw=33,945, Mw/Mn=1.041. 100% Stereo and regio-specificity of the polymer is established by $.^{13}C$ and $.^{1}H$ NMR spectroscopy. Full peak assignments in NMR spectra is accomplished by running $.^{1}H$-$.^{1}H$ COSY and $.^{1}H$-$.^{13}C$ HMQC experiments. Polymer is soluble in cold water and will form non-flowing gel at and above 30° C. for concentrations 5 and 10% and above.

Random Copolymer: pDGDM-pADM

In a sealed vial 0.5 g of DGDM (1,6:2,3-dianhydro-4-O-ethoxy-2-methoxyethyl-b-D mannopyranose), 0.03 g of ADM (1,6:2,3-dianhydro-4-O-allyl-b-D mannopyranose), 0.5 mL of THF and 0.193 g of 210 mmolar dipotassium 3-thiolate-1-propionate in THF are mixed and incubated at 60° C. for 48 hrs. The resulting polymer is precipitated into methanol collected and dried.

A pMDM/DGDM copolymer (27.8 mg), MW about 33 k (30 mol % DGDM), was dissolved in 278 uL $H_2O$ at 5° C. The solution remained a free-flowing liquid at ambient temperature for at least 1 hr, whereupon heating the solution to about 30-40° C. converted the solution to a non-flowing gel. The gel remained non-flowing and transparent at ambient temperature for more than 4 hrs. and at 26° C. for 8 hrs. At 19° C. the gel became a slow flowing viscous liquid. Upon heating the solution to .about.60° C. the gel separated and the polymer precipitated from the solution.

Synthesis of a poly(2-3)-1,6-anhydro-4-O-methyl/co-2-(2-Methoxyethoxy)ethoxy-beta-D-glucopyranose Copolymer A reaction mixture containing, 0.422 g MDM; 0.310 g DGDM, 0.7 g THF, and 0.164 g of a 57 mM solution of potassium 2-butoxyethoxylate in THF was sealed in a vial and incubated at 60'C for 12 hrs. in an argon-filled glove box. The polymerization mixture was then diluted with 2 mL of THF and polymer was precipitated into 50 mL of ether, centrifuged and dried in vacuo. Product recovery was 0.730 g (99.7%). No residual monomer was found in the polymerization mix by GPC. Mn=32,613, Mw=33,945, Mw/Mn=1.041. A 100% stereospecificity and regiospecificity of the polymer was established by $.^{13}C$ and $.^{1}H$ NMR spectroscopy. Full peak assignments in NMR spectra were accomplished by $.^{1}H$-$.^{1}H$ COSY and $.^{1}H$-$.^{13}C$ HMQC. Polymer product was soluble in cold water and formed a non-flowing gel at and above 30° C. at concentrations of 5% and 10% or greater. Other copolymers of MDM and DGDM may be readily synthesized by the same or similar procedures.

Gelation Temperatures of Water-soluble Carbohydrate Polyethers

To determine gelation temperature, water-soluble polymers of the present invention were dissolved in water at 10% w/v and solution temperature was increases at approximately 2° C./min as the viscosity of the solution was monitored with rheometer (TA Instruments, model number AR-62). The lowest temperature at which the solution ceased to flow was recorded as the gelation temperature. Gelation temperatures of representative water-soluble carbohydrate polyethers of the present invention as determined by the procedure described herein are presented in Table 5 and a graph showing the gelation temperature (Gel Point) vs. Mol % DGDM in MDM/DGDM copolymers is presented in FIG. 3 of US 2012/0087891, which is incorporated herein by reference.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A polymeric capsule that is capable of encapsulating at least one mammalian cell, the polymeric capsule comprising a polymer that comprises a plurality of monomer units, wherein the polymer comprises a C2-C3 linked polyether of a 1,6:2,3-dianhydrohexopyranose, wherein the plurality of monomer units comprises;

a monomeric unit represented by formula (1):

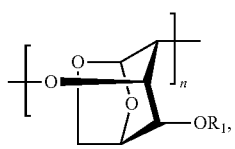

Formula (1)

a monomeric unit represented by formula (2):

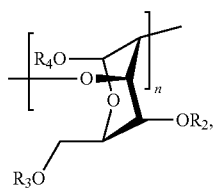

Formula (2)

or a monomeric unit represented by formula (3):

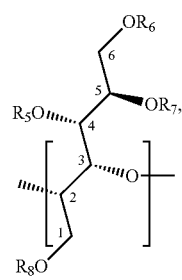

Formula (3)

or any combination of said monomeric units, wherein the capsule exhibits reverse thermal gelation properties in aqueous media.

2. The polymeric capsule of claim 1, wherein the polymer comprises one or both of the polymers: (a) poly(2-3)-1,6-anhydro-4-O-(methyl-co-(2-methoxyethyl)-co-(2-(2-methoxyethoxyethyl))-beta-D-glucopyranose (t-OMD-91); and (b) poly(2-3)-1,6-anhydro-4-O-(methyl-co-(2-methoxyethyl)-co-(2-(2-methoxyethoxyethyl))-b-D-glucopyranose (t-OMD-130).

3. The polymeric capsule of claim 1, wherein the at least one mammalian cell comprises a pancreatic beta cell, an islet of Langerhans, a stem cell, or a chondrocyte.

4. The polymeric capsule of claim 1 that comprises at least one mammalian islet that is in a centered position in the capsule.

5. The polymeric capsule of claim 1 that comprises less than 10% alginate by weight or less than 10% polyethylene glycol by weight.

6. A population of the polymeric capsule of claim 1, wherein at least 90% of the capsules in the population comprise at least one encapsulated mammalian islet, and wherein at least 50% of the capsules that comprise at least one encapsulated mammalian islet comprise at least one encapsulated mammalian islet that is centered in the capsule.

7. A population of the polymeric capsule of claim 1, wherein at least 90% of the capsules in the population comprise at least one encapsulated mammalian islet, and wherein at least 75% of the capsules that comprise the at least one encapsulated mammalian islet are capable of excluding a globular protein of a molecular weight of at least 100 kilodaltons.

8. A population of the polymeric capsule of claim 1, wherein at least 50% of the capsules in the population comprise at least one encapsulated mammalian islet (encapsulated islets), and wherein the encapsulated islets are capable of responding to glucose that is administered to the encapsulated islets, wherein said capable of responding to glucose comprises increased expression of insulin.

9. The population of the polymeric capsule of claim 8, wherein the increased expression of insulin is characterized by a one or more of: a Stimulation Index-1 (SI-1) that is at least 10% greater than a SI-1 of naked islets; a Stimulation Index-2 (SI-2) that is at least 10% greater than a SI-2 of naked islets; and a Stimulation Index-3 (SI-3) that is at least 10% greater than a SI-3 of naked islets.

10. A population of capsules comprising encapsulated mammalian cells that are encapsulated by a polymeric capsule, wherein the population of capsules comprising encapsulated cells is made by a method that comprises the steps of:
   (a) preparing a suspension, slurry, or pellet of mammalian cells;
   (b) providing an available (existing) polymer that comprises a plurality of monomer units that are a C2-C3 linked polyether of a 1,6:2,3-dianhydrohexopyranose, wherein the plurality of monomer units comprises;
   a monomeric unit represented by formula (1):

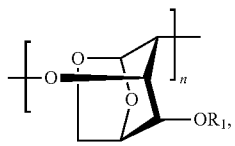

Formula (1)

a monomeric unit represented by formula (2):

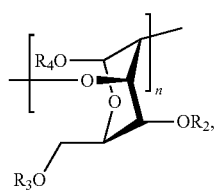

Formula (2)

or a monomeric unit represented by formula (3):

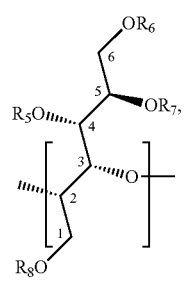

Formula (3)

or any combination of said monomeric units;
   (c) combining the suspension, slurry, or pellet of mammalian cells with the available polymer to produce an aqueous suspension of mammalian cells in said polymer, optionally with also combining an additional aqueous solution that does not comprise mammalian cells in order to ensure enough aqueous solution to provide an aqueous suspension of mammalian cells;
   (d) combining the aqueous suspension of mammalian cells in said polymer with an oil, to produce a combination, wherein the combination is at a first temperature that is a relatively low temperature, and stirring or agitating the combination to produce an emulsion; and
   (e) raising the temperature of the emulsion to a second temperature that is a relatively high temperature, wherein the relatively high temperature is capable of supporting encapsulation of the mammalian cells, wherein a plurality of encapsulated mammalian cells is formed, and wherein the first relatively low temperature is a temperature that is not capable of supporting encapsulation of the mammalian cells.

11. The population of capsules of claim 10, wherein the method further comprises the step of separating the encapsulated mammalian cells from the emulsion.

12. The population of capsules of claim 10, wherein the polymer comprises one or both of the polymers: (a) poly(2-3)-1,6-anhydro-4-O-(methyl-co-(2-methoxyethyl)-co-(2-(2-methoxyethoxyethyl))-beta-D-glucopyranose (t-OMD-91); and (b) poly(2-3)-1,6-anhydro-4-O-(methyl-co-(2-methoxyethyl)-co-(2-(2-methoxyethoxyethyl))-b-D-glucopyranose (t-OMD-130).

13. The population of capsules of claim 10, wherein the mammalian cells comprise at least one of a pancreatic beta-cell or an islet of Langerhans.

14. The population of capsules of claim 10, wherein the mammalian cells do not comprise any pancreatic beta-cells.

15. The population of capsules of claim 10, wherein the population comprises at least one empty capsule.

16. The population of capsules comprising encapsulated mammalian cells of claim 10, that further comprises empty capsules, wherein the ratio of (capsules comprising encapsulated mammalian cells)/(capsules that are empty capsules) is greater than 80/20.

17. A method for synthesizing a population of capsules comprising encapsulated mammalian cells, wherein the method comprises the steps of:
   (a) preparing a suspension, slurry, or pellet of mammalian cells;
   (b) preparing an available (existing) polymer that comprises a plurality of monomer units that are a C2-C3 linked polyether of a 1,6:2,3-dianhydrohexopyranose, wherein the plurality of monomer units comprises;
   a monomeric unit represented by formula (1):

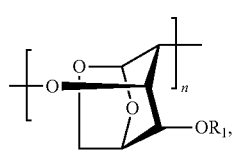

Formula (1)

a monomeric unit represented by formula (2):

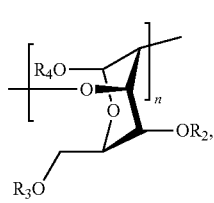

Formula (2)

or a monomeric unit represented by formula (3):

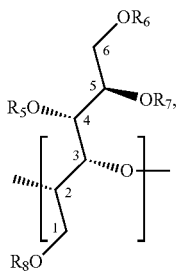

Formula (3)

or any combination of said monomeric units;

(c) combining the suspension, slurry, or pellet of mammalian cells with the available polymer to produce an aqueous suspension of mammalian islets in the available polymer, optionally with also combining an additional aqueous solution that does not comprise mammalian cells in order to ensure enough aqueous solution to provide an aqueous suspension of mammalian cells;

(d) combining the aqueous suspension of mammalian cells in said polymer with an oil, to produce a combination, wherein the combination is at a first temperature that is a relatively low temperature, and stirring or agitating the combination to produce an emulsion;

(e) raising the temperature of the emulsion to a second temperature that is a relatively high temperature, wherein the relatively high temperature is capable of supporting encapsulation of the mammalian cells, wherein a plurality of encapsulated mammalian cells is formed, and wherein the first relatively low temperature is defined as one that is not capable of supporting encapsulation of the mammalian cells; and (f) reducing the temperature to a third temperature that is not capable of supporting further encapsulation of mammalian cells.

18. The method of claim 17, wherein the polymer comprises one or both of the polymers: (a) poly(2-3)-1,6-anhydro-4-O-(methyl-co-(2-methoxyethyl)-co-(2-(2-methoxyethoxyethyl))-beta-D-glucopyranose (t-OMD-91); and (b) poly(2-3)-1,6-anhydro-4-O-(methyl-co-(2-methoxyethyl)-co-(2-(2-methoxyethoxyethyl))-b-D-glucopyranose (t-OMD-130).

* * * * *